US012590316B2

(12) United States Patent
Liu et al.

(10) Patent No.: US 12,590,316 B2
(45) Date of Patent: Mar. 31, 2026

(54) USE OF β-1,3-GLUCAN SYNTHASE LIKE 5 IN IMPROVING CLUBROOT DISEASE RESISTANCE AND RELATED PRODUCT DEVELOPMENT IN CRUCIFEROUS CROPS

(71) Applicant: Institute of Oil Crops Chinese Academy of Agricultural Sciences, Wuhan City (CN)

(72) Inventors: Lijiang Liu, Wuhan City (CN); Shengyi Liu, Wuhan City (CN); Yi Zhang, Wuhan City (CN); Yupo Wu, Wuhan City (CN); Chuanji Zhao, Wuhan City (CN); Xiaohui Cheng, Wuhan City (CN); Fan Liu, Wuhan City (CN); Li Ren, Wuhan City (CN); Junyan Huang, Wuhan City (CN); Xiaoling Dun, Wuhan City (CN)

(73) Assignee: Institute of Oil Crops Chinese Academy of Agricultural Sciences, Wuhan City (CN)

( * ) Notice: Subject to any disclaimer, the term of this patent is extended or adjusted under 35 U.S.C. 154(b) by 7 days.

(21) Appl. No.: 18/814,578

(22) Filed: Aug. 25, 2024

(65) Prior Publication Data

US 2025/0171799 A1      May 29, 2025

(30) Foreign Application Priority Data

Nov. 23, 2023    (CN) ......................... 202311580841.X

(51) Int. Cl.
*C12N 15/82*        (2006.01)
*C12N 9/10*        (2006.01)
(52) U.S. Cl.
CPC ....... *C12N 15/8279* (2013.01); *C12N 9/1051* (2013.01); *C12Y 204/01034* (2013.01)
(58) Field of Classification Search
None
See application file for complete search history.

(56) References Cited

U.S. PATENT DOCUMENTS

2019/0241904 A1     8/2019 Engelen et al.

FOREIGN PATENT DOCUMENTS

CN        115948419 A      4/2023

OTHER PUBLICATIONS

GenBank Accession No. XM_013755540 (Year: 2015).*
Huibers et al. PLoS One. 8(6):e67467. (Year: 2013).*
Gene ID: 825650. Ncbi. GSL05 glucan synthase-like 5. https://www.ncbi.nlm.nih.gov/gene/825650. Accessed 2024.*
Gunasinghe et al. Disease Notes. 97(9):1256-1256. (Year: 2013).*
Miguel et al., CRISPI/ Cas9-targeted mutagenesis of the tomato susceptibility gene PMR4 for resistance against powdery mildew. Jun. 19, 2020. BMC Plant Biology, vol. 20. pp 1-13.
Jing Wang et al, Research Progress in Clubroot of Crucifers. Plant protection. Dec. 31, 2011. vol. 37, issue 6. 153-158 (full document).

* cited by examiner

*Primary Examiner* — Mykola V. Kovalenko
*Assistant Examiner* — David R Byrnes
(74) *Attorney, Agent, or Firm* — Tutunjian & Bitetto, P.C.

(57) ABSTRACT

The present disclosure provides the use of β-1,3-glucan synthase like 5 (GSL5) for the improvement of the clubroot resistance in cruciferous crops as well as related products development, belonging to the area of molecular engineering for plant breeding. GSL5 gene is highly conserved in cruciferous plants and mutation of GSL5 can confer a broad-spectrum and high clubroot resistance to the cruciferous crops, demonstrating that molecular engineering of GSL5 can achieve the improvement of the clubroot resistance in cruciferous crops. The present disclosure provides a key gene and techniques for the improvement of the clubroot disease resistance and durable prevention and control of the clubroot disease in cruciferous crops.

4 Claims, 4 Drawing Sheets

Specification includes a Sequence Listing.

USE OF β-1,3-GLUCAN SYNTHASE LIKE 5 IN IMPROVING CLUBROOT DISEASE RESISTANCE AND RELATED PRODUCT DEVELOPMENT IN CRUCIFEROUS CROPS

SEQUENCE LISTING INCORPORATION BY REFERENCE

The instant application contains a Sequence Listing which has been submitted electronically in XML format and is hereby incorporated by reference in its entirety. The name of the text file containing the sequence listing is LOTUT_PRIORITY_TO_202311580841X.xml, has a file size of 108,492 bytes, and was created on Aug. 25, 2024.

TECHNICAL FIELD

The present disclosure belongs to the technical field of plant breeding, and in particular, to a use of the gene β-1,3-glucan synthase like 5 (GSL5) gene in the improvement of the clubroot disease resistance and the development of related products in the cruciferous crops.

BACKGROUND

Cruciferous crops include *Brassica napus, Brassica rapa, Brassica oleracea, Brassica juncea, Raphanus sativus*, etc., which are important sources of human edible oils, vegetables, feed and industrial oils, and one of the most important economic crops in the world.

The cruciferous clubroot disease is a devastating soil-borne disease caused by the protozoan *Plasmodiophora brassicae*, and can jeopardize almost all the cruciferous crops, resulting in root swelling, rot and plant death. The average yield loss is about 25-50% annually, and in some severe diseased fields, the yield loss is up to 100%. The *P. brassicae* can survive in the soil for more than 10 years in the infested fields and thus, these fields would be unsuitable for the cultivation of any susceptible cruciferous crop.

Exploiting the clubroot resistance genes for clubroot resistance breeding is the most economical and effective measure to prevent and control the clubroot disease. *P. brassicae* specialize in the virulence and could be divided into different physiological races. The presently used clubroot-resistant loci are mainly from the European fodder turnips (*B. rapa* ssp. *rapifera*), and all of them are dominant and race-specific. Consequently, the clubroot resistance of the developed resistant varieties are usually lost after 3-year plantation in the disease fields. Meantime, the breeding of clubroot-resistant varieties always takes a long time but are always in great demand. However, the resistance of broad-spectrum clubroot-resistant gene cannot be easily overcome by the diverse physiological races and thereby, is an ideal gene for clubroot resistance breeding to durably control this disease. Presently, the broad-spectrum clubroot resistance gene has not yet been discovered.

SUMMARY

In the present disclosure, we provide a use of the cruciferous crop GSL5 gene in improving clubroot disease resistance and products development in the cruciferous crops. By molecular engineering of GSL5, we can achieve the improvement of broad-spectrum clubroot resistance in the cruciferous crops, thereby providing a key gene and associated techniques to durably and efficiently control the cruciferous clubroot disease.

To achieve the above-mentioned objective of the present disclosure, the present disclosure provides the following technical solutions:

Decrease or termination in GSL5 transcription or expression level or mutation or modification of the protein sequence to terminate or change GSL5 function by molecular engineering of GSL5 promoter regions, coding regions, and non-coding regions in the cruciferous crops.

Preferably, the molecular engineering includes the gene editing, EMS mutagenesis, radiation mutagenesis, homologous recombination, and T-DNA insertion.

Preferably, the cruciferous crops include but not are limited to *Arabidopsis thaliana, Brassica napus, Brassica rapa, Brassica oleracea, Brassica juncea*, and *Raphanus sativus*.

Preferably, the nucleotide sequence of the GSL5 genes include SEQ ID NO. 1, SEQ ID NO. 2, SEQ ID NO. 3, SEQ ID NO. 4, SEQ ID NO. 5, SEQ ID NO. 6, SEQ ID NO. 7 and SEQ ID NO. 8.

The present disclosure further provides a nucleotide sequence for gene editing of GSL5 which is shown in SEQ ID NO. 9 or SEQ ID NO. 10 and the cruciferous crops include *Brassica napus, Brassica rapa* and *Brassica oleracea*.

The present disclosure further provides a recombinant vector and strain for gene editing of cruciferous crop GSL5 genes.

Compared to the current techniques, the present disclosure has the following advantages:

(1) GSL5 is highly conserved in the cruciferous crops and knocking out of it can achieve the improvement of broad-spectrum clubroot resistance in the cruciferous crops, providing the first gene in improving the broad-spectrum clubroot resistance in cruciferous crops. Therefore, the gene GSL5 is expected to have huge economic and social benefits worldwide.

(2) Gene editing of GSL5 can significantly shorten the period of clubroot resistance breeding cycle, providing a new way to achieve the improvement of clubroot resistance breeding in cruciferous crops.

(3) The new germplasm of *Arabidopsis thaliana, Brassica napus, Brassica rapa, Brassica oleracea* with a broad-spectrum clubroot resistance have been generated, providing key germplasm resources for efficient and durable prevention and control of the clubroot disease in cruciferous crops.

(4) GSL5 has been identified as a key susceptible gene for *P. brassicae* infection and pathogenesis and knocking out of GSL5 is expected to block a key step during *P. brassicae* infection process, thereby conferring a broad-spectrum clubroot resistance. The present disclosure provides a new theoretic and technical support to achieve the improvement of the clubroot resistance in cruciferous crops.

(5) GSL5 is widely spread and highly conserved in cruciferous crops. Molecular engineering of only one GSL5 is expected to achieve the improvement of broad-spectrum clubroot resistance in cruciferous crops, thereby being of great significance to cruciferous crop breeding.

DETAILED DESCRIPTION OF EMBODIMENTS

Figure 1:
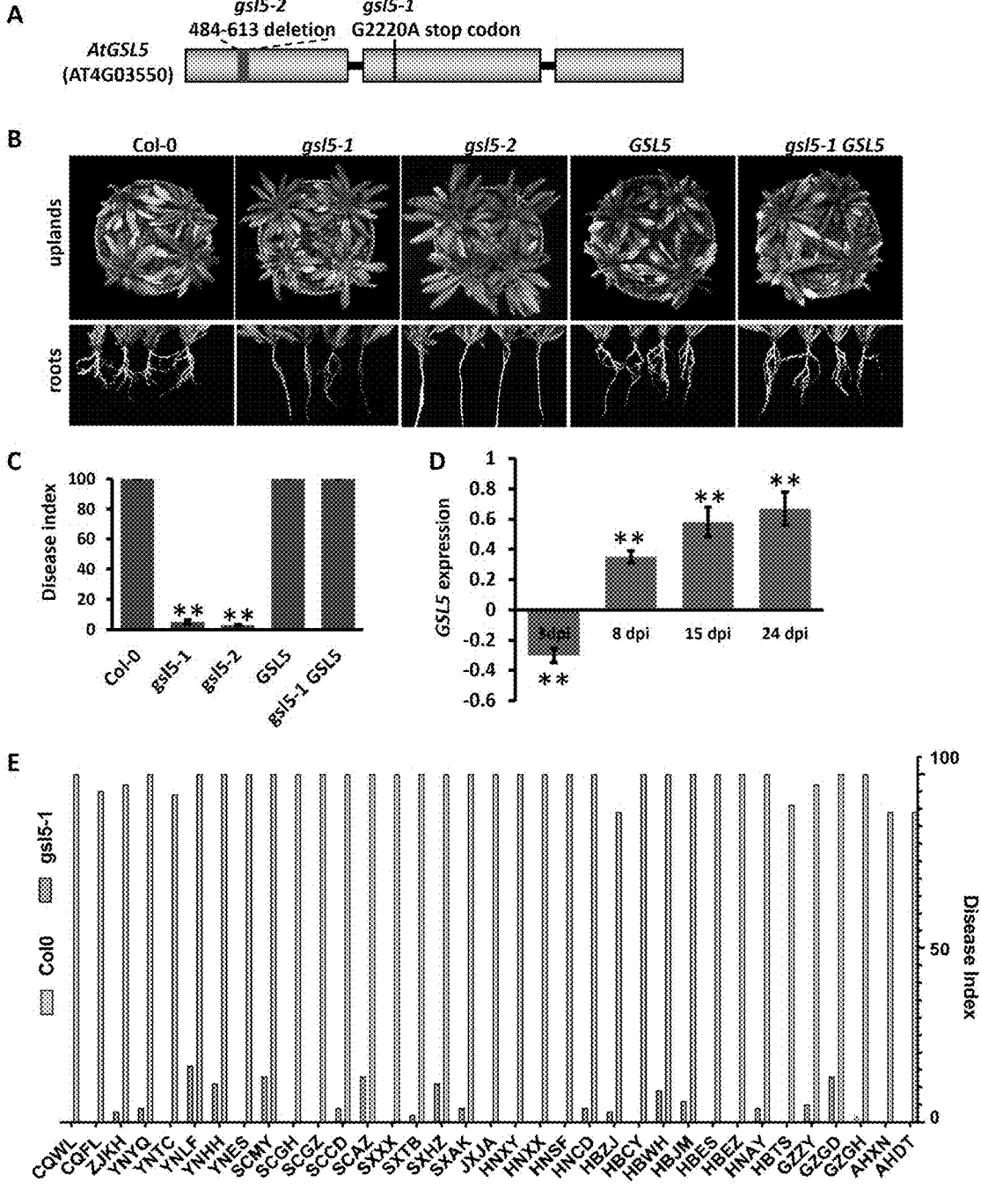
FIG. 1 shows that loss-of-function mutation of GSL5 confers a broad-spectrum resistance to the clubroot resistance in *A. thaliana*. A. the gene structure of GSL5 genetic structure. The mutation gsl5-1, also known as pmr4-1 results in the presence of a stop condon at the position 2220 while the mutation gsl5-2 results in a deletion of sequence at position 484-613; B and C. the mutants gls5-1 and gsl5-2 are highly resistant to the clubroot disease and have no significant impact on plant growth and development; D. GSL5 expression is significantly up-regulated during the secondary infection of *P. brassicae* in the root cortex; E. GSL5 mutation confers a broad-spectrum clubroot resistance.

The present disclosure provides a use of the GSL5 (Glucan Synthase-Like 5 or Callose synthase 12, CalS12) in improving clubroot disease resistance of the cruciferous crop. Decrease or termination in GSL5 transcription or expression level or mutation or modification of the protein sequence to terminate or change GSL5 function by molecular engineering of GSL5 promoter regions, coding regions, and non-coding regions in the cruciferous crops could confer a broad-spectrum clubroot resistance in cruciferous crops.

The preferred molecular engineering includes but is not limited to the gene editing, EMS mutagenesis, radiation mutagenesis, homologous recombination, and T-DNA insertion.

Preferably, the cruciferous crops include but not are limited to *Arabidopsis thaliana, Brassica napus, Brassica rapa, Brassica oleracea, Brassica juncea*, and *Raphanus sativus*. Preferably, the nucleotide sequence of the GSL5 genes include SEQ ID NO. 1, SEQ ID NO. 2, SEQ ID NO. 3, SEQ ID NO. 4, SEQ ID NO. 5, SEQ ID NO. 6, SEQ ID NO. 7 and SEQ ID NO. 8. The detailed descriptions are in the following: SEQ ID NO. 1 is the genomic sequence of *A. thaliana* GSL5; SEQ ID NO. 2 is the genomic sequence of the subgenome A GSL5 of the *B. napus*; SEQ ID NO. 3 is the genomic sequence of the subgenome C GSL5 of the *B. napus*; SEQ ID NO. 4 is the genomic sequence of *B. rapa* GSL5; SEQ ID NO. 5 is the genomic sequence of *B. oleracea* GSL5; SEQ ID NO. 6 is the genomic sequence of the subgenome A GSL5 of the *B. juncea*; SEQ ID NO. 7 is the genomic sequence of the subgenome BGSL5 of the *B. juncea*; and SEQ ID NO. 8 is the genomic sequence of *R. sativus* GSL5. In view of the highly conserved characteristics of GSL5 in the cruciferous plants, the GSL5 genes of other cruciferous plants that were not mentioned should also be listed into the protective scope of the present disclosure.

The present disclosure further provides a nucleotide sequence for gene editing of the cruciferous crop GSL5 which is shown in SEQ ID NO. 9 or SEQ ID NO. 10. The cruciferous crop includes *B. napus, B. rapa* and *B. oleracea* crops. The GSL5 target sequences of *B. napus, B. rapa* and *B. oleracea* are completely identical and contain a length of 20 bases with the 3' end containing an NGG motif, where N represents any one of the bases A, G, C, and T. In view of the highly conserved characteristics of GSL5 in the cruciferous plants, the consensus sequences of the GSL5 genes of all cruciferous crops containing above characteristics should be listed into the protective scope of the present disclosure.

The present disclosure further provides a recombinant vector containing the above nucleotide sequence. This recombinant vector can be transfected into the cruciferous crop to obtain clubroot resistant materials. The gene editing of GSL5 can result in insertion, deletion or mutation in the exon regions.

The present disclosure further provides a recombinant strain containing the recombinant vector.

The technical solutions provided by the present disclosure will be described in detail in several examples below that, however, should not be viewed to limit the protective scope of the present disclosure.

Example 1: Mutation of *A. thaliana* GSL5 and Test of the Broad-Spectrum Clubroot Resistance The *A. thaliana* mutant gsl5-1, also known as pmr4-1 (Stock No. CS3858), was ordered from the *Arabidopsis thaliana* Biological Resource Center, containing a mutation from G to A at the position 2220 (gene No. AT4G03550), resulting in the presence of stop codon and loss-of-function mutation of GSL5 protein. The *A. thaliana* mutant gsl5-2 was obtained by gene editing, and this mutant had a deletion in the first exon at the position 484-613, resulting in a frameshift mutation of the coding region and loss-of-function of GSL5.

FIG. 1 shows that loss-of-function mutation of GSL5 confers a broad-spectrum resistance to the clubroot resistance in *A. thaliana*. Four target sites for gene editing were designed in the first exon of GSL5 with the target site sequences as follows:

sgRNA1: 5'-ACGAAACCGACGAACAACCGCGG-3', shown in SEQ ID NO. 11;

sgRNA2: 5'-TATTGATTCTCTCGATTCCGCGG-3', shown in SEQ ID NO. 12;

sgRNA3: 5'-GAACGCCATTGAACATACGGCGG-3', shown in SEQ ID NO. 13;

sgRNA4: 5'-GATTGCCTCGATGAGAACACCGG-3', shown in SEQ ID NO. 14;

Primers used for PCR identification of gene-edited progeny plants were:

GSL5-F1: 5'-CGCCGTCTCAGAGCTACAA-3', shown in SEQ ID NO. 15;

GSL5-R1: 5'-GGCGGCTTGAAGGAACAAAG-3', shown in SEQ ID NO. 16.

The GSL5 gene used to complement gsl5-1 was the full length of the genomic region with its native promoter (2500 bp upstream of the start codon). The genomic region of GSL5 was cloned from *A. thaliana* ecotype Col-0, the primers and sequencing were completed by Tsingke Biotechnology Co., Ltd. (Beijing). The primers used to clone the *A. thaliana* GSL5 promoter and gene fragment were:

```
AtGSL5F:
GTCGACCTGCAGGCATGCCTGTCTTAAATGGACATTTGTAGTAACAAA;

AtGSL5R:
AAGTTCTCTCCTTTACTGACATCGCCTTTTTGATTTCTTC;
```

As shown in SEQ ID NO. 17 and SEQ ID NO. 18, the targeted sequence is incorporated into the expression vector PBI121 by double enzyme digestion (enzyme cutting sites were HindIII and Kpn I) and homologous recombination. After verification by sequencing, the recombinant vector was transformed into the agrobacterium strain GV3101 subjected to transformation following the agrobacterium-mediated flower dipping method. The progeny plants were screened by using kanamycin resistance and positive plants were further identified by PCR to amplify a fragment of the kanamycin gene. The primers were in the follows:

```
KanR-jcF:
CCTGTTCCAAAGGTCCTGCA;

kanR-jcR:
TGTCATACCACTTGTCCGCC;
```

As shown in SEQ ID NO. 19 and SEQ ID NO. 20, the obtaining of the 500 bp PCR product demonstrated the transgenic plants overexpressing GSL5. By crossing the gsl5-1 plants with GSL5 overexpression plants, the progeny plants were identified with PCR to amplify the kanamycin gene (the primers were the same as the aforementioned) to screen the complemented gsl5-1 GSL5 plants. Clubroot resistance test of Col-0, gsl5-1, GSL5 and gsl5-1 GSL5 plants was carried out in a plant greenhouse. *P. brassicae* strains were collected from the diseased plants across China. Two-week-old seedlings were used for inoculation of different *P. brassicae* isolates with the resting spore suspension

*Oilseed Rape* (NY/T 3621-2020)》. The material with a disease index ≤10 is considered to be highly resistant.

Example 2: The Highly Conserved Characteristics of GSL5 in Cruciferous Plants The homologs of *Arabidopsis* GSL5 were identified with the online collinearity analysis tool of the BRAD database (www.brassicadb.cn/#/syntenic-gene/) in the genomes of *B. napus, B. rapa, B. oleracea, B. juncea, R. sativus*. The genome of the allotetraploid crops *B. napus* and *B. juncea* contained two GSL5 homologs while the diploid crops *B. rapa, B. oleracea* and *R. sativus* contain only one GSL5 homolog. Multiple sequence alignment of the GSL5 from different cruciferous plants was carried out with an online tool COBALT (www.ncbi.nlm.nih.gov/tools/cobal-t/re_cobalt.cgi) and was virtualized with the software Jalview. The genomic region of GSL5 from different cruciferous crops including its native promoter (2500 bp upstream of the start codon) was respectively cloned and connected to PBI121 expression vector. The *agrobacterium* containing the constructed vector was transfected into *Arabidopsis* gsl5-1 mutant and the progeny plants were identified using PCR. The resultant complemented plants were used for clubroot resistance test as the methods mentioned in Example 1. The primer sequences used to clone the genomic region of GSL5 from different cruciferous crops were shown in Table 1.

TABLE 1

| The primer sequences used to amplify the genomic region of GSL5 from different cruciferous crops. | | | | |
|---|---|---|---|---|
| Species | Amplified gene | Primer | Primer sequence | Serial number SEQ ID |
| *Brassica napus* | BnaA09.GSL5 | Forward | TATGACCATGATTACGCCCAATTTGCGGCCAAGTTC CA | NO. 21 |
| | | Reverse | ACTAGTCAGATCTACCATTCAAGACCTTCTTTTTTC AACTTCGAC | NO. 22 |
| | BnaC09.GSL5 | Forward | TATGACCATGATTACGCCGCTTGTCTTGCTTGTTTT TGCTC | NO. 23 |
| | | Reverse | ACTAGTCAGATCTACCATTTAAGACCTTCTTTTTTC AACTTCGACA | NO. 24 |
| *Brassica rapa* | BraGSL5 | Forward | TATGACCATGATTACGCCCGATAAGGAAACGAGA GAGGTTG | NO. 25 |
| | | Reverse | ACTAGTCAGATCTACCATGCTGTAACGTTTCAGAC AATAACC | NO. 26 |
| *Brassica oleracea* | BolGSL5 | Forward | TATGACCATGATTACGCCGTGTGTTTCGGAAAGCA GCAAAC | NO. 27 |
| | | Reverse | ACTAGTCAGATCTACCATACTGAAACCCAGGCATC CACG | NO. 28 |
| *Brassica juncea* | BjuA09.GSL5 | Forward | TATGACCATGATTACGCCGTTAGGTGACGACTATA TCAGCAT | NO. 29 |
| | | Reverse | ACTAGTCAGATCTACCATGAGAGAAAGATATCAAAT CTTGCAC | NO. 30 |
| | BjuB08.GSL5 | Forward | TATGACCATGATTACGCCGCTAATCTTGAACAAGT CCTGGAT | NO. 31 |
| | | Reverse | ACTAGTCAGATCTACCATGGAAGACGTGAGATAT GAATGCAA | NO. 32 |
| *Raphanus sativus* | RsGSL5 | Forward | TATGACCATGATTACGCCGTACCTGTAATTAGTCA ACTGTTC | NO. 33 |
| | | Reverse | ACTAGTCAGATCTACCATCACCATCTCCAAGATCC ACCAC | NO. 34 |

(108/plant) and the disease severity was investigated 30 days after inoculation according to the disease scale specified by the national industry standard of China 《 *Technical Code of Practice for Evaluation of Clubroot Disease Resistance in*

Figure 2:
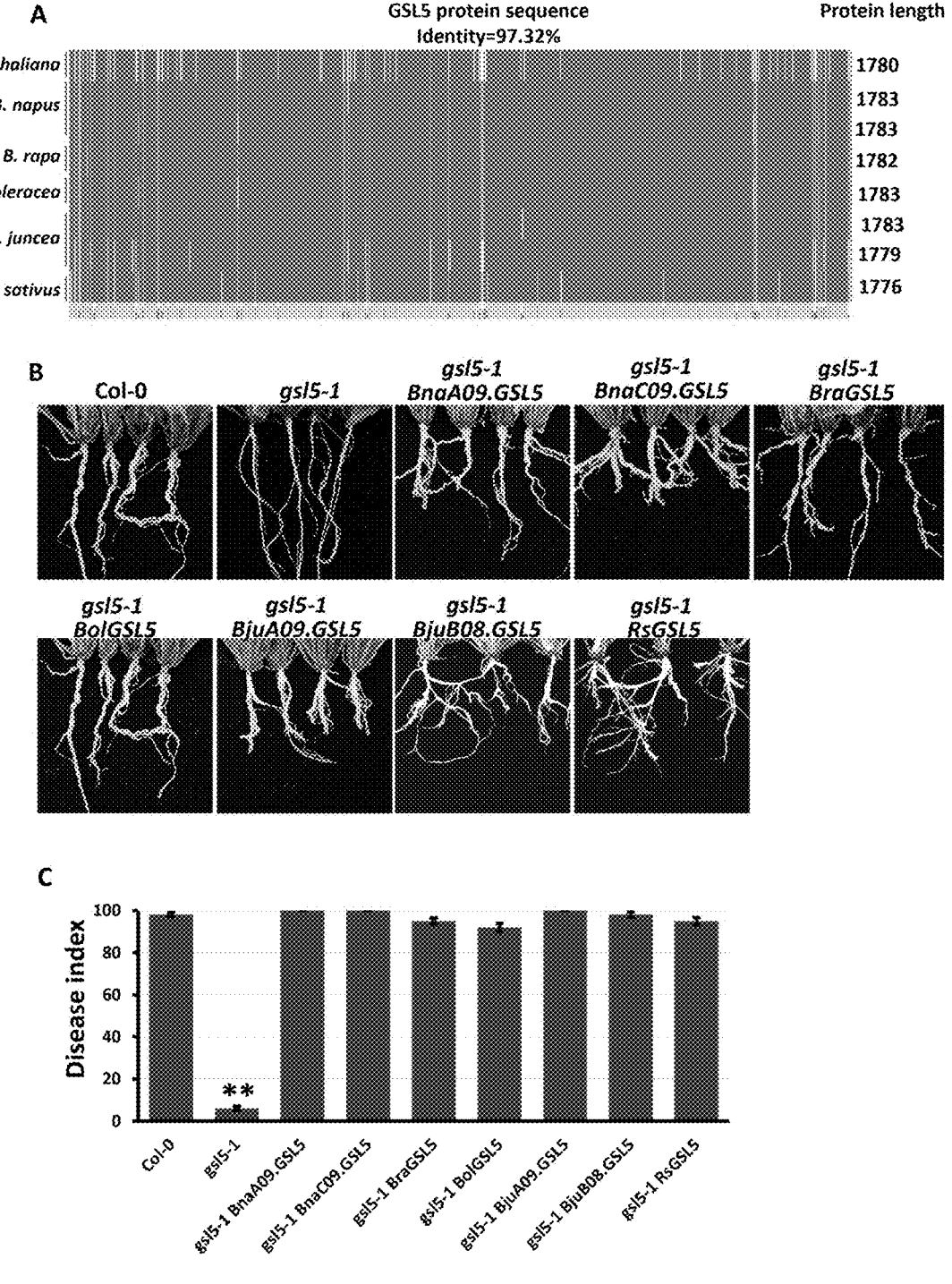
FIG. 2 shows the highly conserved characteristic of GSL5 in cruciferous plants; A. the highly conserved protein sequence of GSL5 in the representative cruciferous plants. B and C. the GSL5 from five representatives of cruciferous crops can functionally complement the *Arabidopsis* gsl5 mutant to restore its susceptibility.

The results were shown in FIG. 2. A. the highly conserved protein sequence of GSL5 in the representative cruciferous plants. B and C. the GSL5 from five representatives of cruciferous crops can functionally complement the *Arabidopsis* gsl5 mutant to restore its susceptibility. *B. napus* (BnaA09.GSL5, BnaC09.GSL5), *B. rapa* (BraGSL5), *B. oleracea* (BolGSL5), *B. juncea* (BjuA09.GSL5, BjuB08.GSL5) and *R. sativus* (RsGSL5).

Example 3: Knocking Out of GSL5 Genes of *B. napus, B. Rapa* and *B. oleracea* Achieved the Improvement of the Broad-Spectrum Clubroot Resistance Breeding The cruciferous crops for gene editing of GSL5 include the *B. napus* spring variety Westar and hemi-winter variety Zhongshuang 11, the *B. rapa* ssp. *chinensis* variety Chinese cabbage F554, and the *B. oleracea* ssp. *capitata* variety HXF. The gene editing vector pYLCRISPR/Cas9 was used to knock out the GSL5 gene from above crops. Two target sites for gene editing were designed in the first exon of GSL5, and the target sequences were in the following:

sgRNA1: 5'-ACACGAACATCTGGAAGCAGAGG, shown in SEQ ID NO. 9;
    sgRNA2: 5'-GAAAGCCACCACAGCGTAAAGG, shown in SEQ ID NO. 10;
    The *agrobacterium* containing the constructed vectors were used to transfect the hypocotyl of above crops. The T1-generation transgenic plants were self-polli-nated to generate the T2 population for screening the homozygous mutant gsl5. The primer sequences used to amplify the targeted editing sites of GSL5 from above crops were listed in the following:
*B. napus* A Subgenome GSL5:
    BnGSL5A-F: GACGCTGGCTCGCAACGGT, shown in SEQ ID NO. 35;
    BnGSL5A-R: CGGCCGCCCCAATCCATACC, shown in SEQ ID NO. 36;
*B. napus* C Subgenome GSL5:
    BnGSL5C-F: ACGCTGCCTCGCAACGGC, shown in SEQ ID NO. 37;
    BnGSL5C-R: TGGCCGCCCAAGTCCATACCT, shown in SEQ ID NO. 38;
    The primers used to amplify the target site of GSL5 from *B. rapa* were the same as that used for amplification of the targeted sites from *B. napus* A subgenome.
*B. oleracea* GSL5:
    BoGLS5-F: ACGCCTGGCTCGCAACGGC, shown in SEQ ID NO. 39;
    BoGSL5-R: CGGCCGCCCCAATCCATACC, shown in SEQ ID NO. 40;
    Clubroot resistance test of the gsl5 mutant of above crops was performed as the methods mentioned in Example 1.

Figure 3:
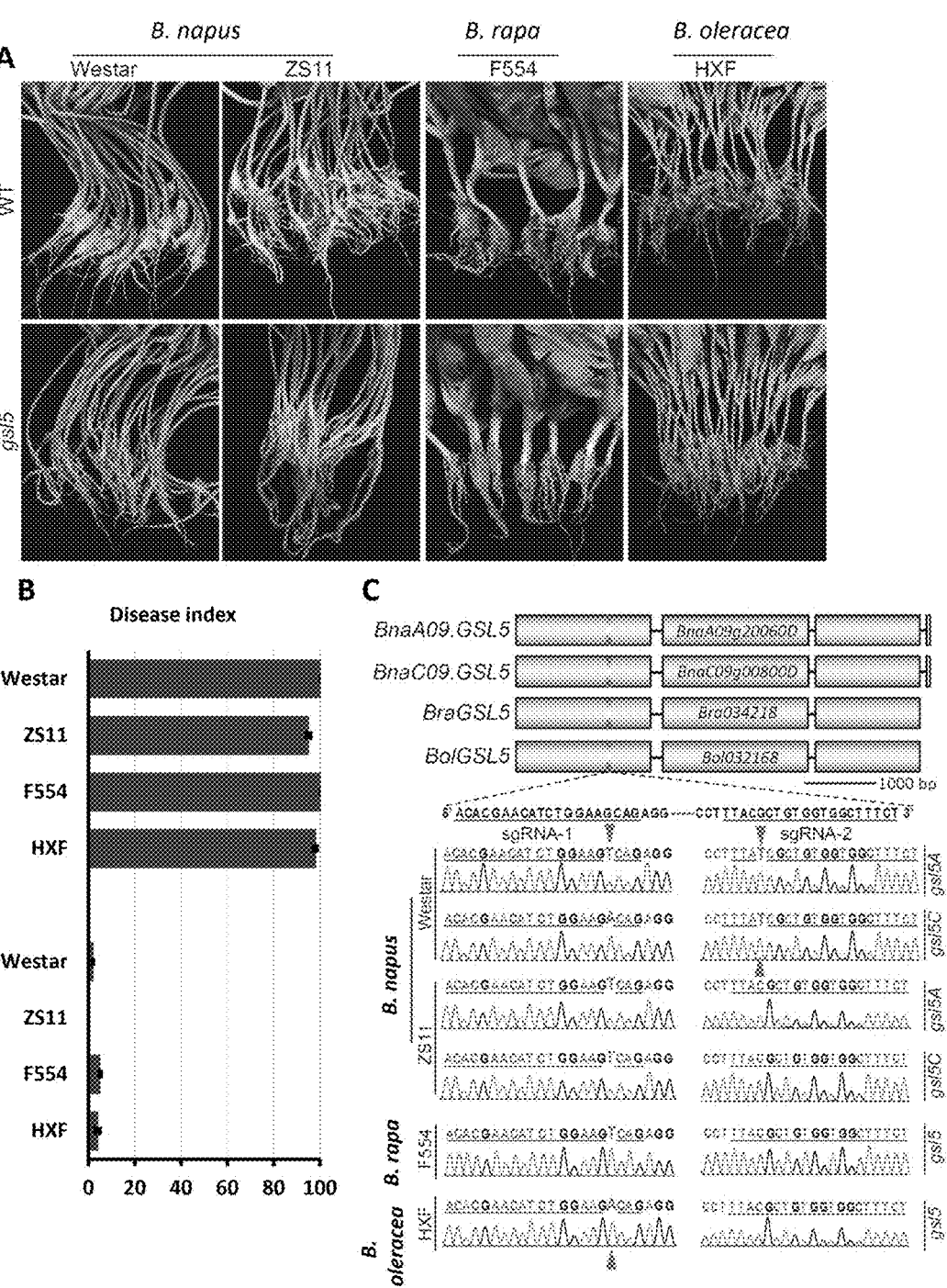
FIG. 3 shows that gene editing of GSL5 in susceptible *B. napus, B. rapa* and *B. oleracea* can significantly improve the clubroot resistance; A and B. clubroot resistance test of the homozygous gsl5 mutant plants of the *B. napus, B. rapa* and *B. oleracea*; C. the edited target sequence of GSL5 the *B. napus, B. rapa* and *B. oleracea.*

FIG. 3 shows that gene editing of GSL5 in susceptible *B. napus, B. rapa* and *B. oleracea* can significantly improve the clubroot resistance; A and B. clubroot resistance test of the homozygous gsl5 mutant plants of the *B. napus, B. rapa* and *B. oleracea*; C. the edited target sequence of GSL5 the *B. napus, B. rapa* and *B. oleracea*.

Figure 4:
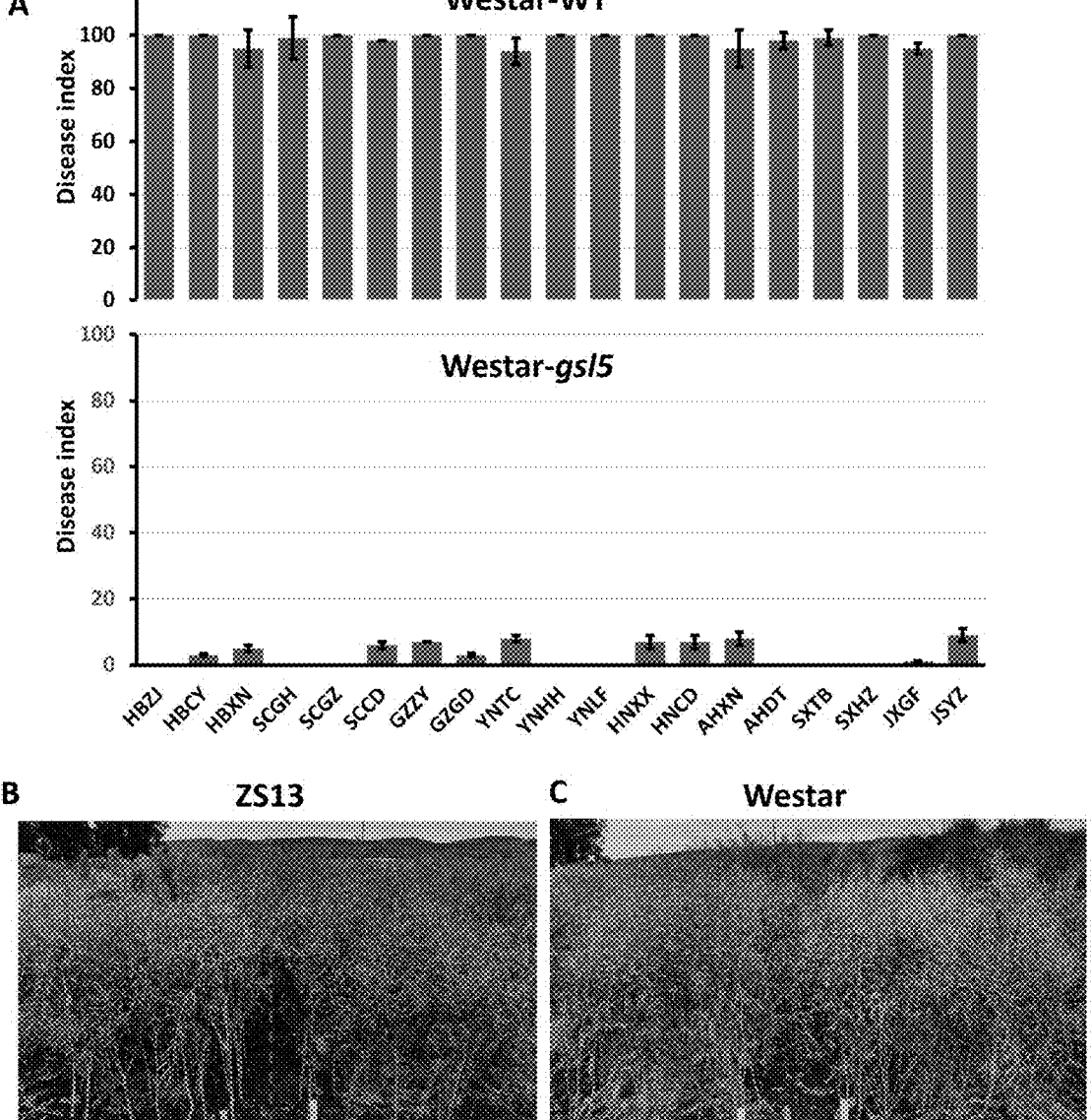
FIG. 4 shows that *B. napus* mutant gsl5 has a broad-spectrum clubroot resistance without growth and development penalties. A: *B. napus* gsl5 homozygous mutant plants have a broad-spectrum high resistance to different *P. brassicae* isolates. B: the mutation of gsl5 has no obvious effect on plant growth and development of *B. napus*.

The gsl5 mutant of *B. napus* variety Westar were inocu-lated with different isolates of *P. brassicae* for clubroot resistance test. The results show that the gsl5 mutant plants have a broad-spectrum and high resistance to different isolates of *P. brassicae* (FIG. 4A). The gsl5 mutation had no obvious effect on the growth and development of the *B. napus* plants (FIGS. 4B and C).

The above clauses are only the preferable embodiments of the present disclosure. It should be noted that for those who possess the basic skills of the molecular engineering, further improvements and modifications of GSL5 in order to improve the clubroot resistance in cruciferous crops should be regarded as the protective scope of the present disclosure.

SEQ ID NO. 1

CTGTCTTAAATGGACATTTGTAGTAACAAAACCGACCATCAGCAAATTAA

CGTTAACGTTGCTCTAATCGTGTGTATTTTTCTAATGCTTGGTGAAGCAC

ATGCGACCATTTGTTGTGTCAGAACAAAAGGAAGATTCCACATTTAGAAT

TTAGATTATAATCCCACATGCCTATTATTTAAACATATGTATACTGTAAT

AAATTAGTCCCAGAAGAGCATTTCATCATACTGTATAATTAATCAAATTT

AAAAAACATTTGTGTTGAAGAGAAGATGACTAGATTCACTTGATTTTTTT

TAATACTGATTGGTCGTTTGACCAGTCAGGATCCAGACTGAAATATTCTC

AAAAGGTATGAACTATTTTAATGAAATATTTGAGCTGAGAATTTGCTTAT

GGGACATTCTATCCTTCTAAAGAAATCATTAGAAAATGGAGAAAAGTTA

CTAGAAAAAGAGAGGGAAATGGGGCGAGAGTATGAAGAAAGGGTCCCATG

TGAATCTAATAATTGAAAAGCAAATATGAGATTTATTTTAGGGTTCTTGT

TTTAGCGTCCAAAGCGGTCGCAGTTGCCGTTCAGCGACTTTTCTCTGTTT

ATGAAATAAAAACGCTCCACTTGTTCTTTTCTTCTTTCAACCCACTTTGT

TATAACTATTAACAAATATTGCTTGGTCCAAATTTTATTATACTGAATTA

TTTTAGTTTTTTTGTATCATCATCCTCAATGTTAGTTTTGAAATCCTAGG

TCAGTAAGTCAATAACGAAAATGACAAGTTTAATTTTGTAATTGGAACTT

ACATGTCACGGTCTTTGTTTACGATCATTGCCACGAATTGTTTAGATACG

GGCTTTTTTTTTCTTTCCGTGTTGATGATTATCGTTTCTTCTTACATATC

TTGATCAATCACTAACATTTACATAACCTACAATTTTGTAATATAATTGC

AATACTCGAGATCTTCAAATGGTGATACTGTTAATAAAATTACGAACTTT

TAATCATCATCAAAATCTATAGAAAAAGATACATAGGACCAAAACAAGCC

TAAAACAAAGAGTTATAATTTACAAATAAATGCATGTATTTTGTTACTTT

TGTTAAGGATTTTCATATCAATGCATGCATAATGCATTCTCTTTTTATTT

TATTTATAATGCATTCTTTTATAATATTCGGATCCAAAATTATGAATTAA

TTCCAGATTGCCATAAATGTCTTTCTTTGTTTATGCTGACTTTTTTCTTT

TCTTAACTTATATAGTAAGTAAACCAGAAAGGTGGAAGATACAAAGCAAT

TTCATTGCATTAATAAACTTCAAATGTATTATCCAATAATCAAAATTTAT

CTAGTAATTCACAAAAAAAAAAAAAATCTGTCTATCATTCAAAATTTCACC

AATTTGGATAAATATCTAGAAAATTTTAAAATACAATTCAATAACACTAT

TAACATATCAATCAATATATAACATTGCAAAAGTTTACTTGATCATTAGT

ATATTCATTTTAAGGTTAAAAGATCTTTAAGAAAAGGAAATTCAAATTAT

ATTGTTGGAAAAAAATACAAATCAAAGACAGCAAAAAAAGTAACAAAAAA

AAAAGGTAGAAGAAACTGAAACGCGGAAAGGAGGCAAAATCTTCTCGTCG

TCGTTGTCGCCGTCTTCAGAGCTACAAACGAAAAAACTCGCTTCCGTTTC

GATTTCTCCATTGTTATTGTTTCTTCAGTGAAGCTTTTTTCTTCGAGAAA

TTTCTAAGATCTACCACATGCTACTATGAGCCTCCGCCACCGCACCGTCC

CGCCGCAAACCGGACGGCCGTTGGCGGCGGAAGCTGTCGGAATCGAAGAG

GAGCCGTACAATATCATTCCCGTTAACAATCTCCTCGCCGACCATCCTTC

-continued

ACTCCGTTTTCCCGAGGTTCGTGCCGCCGCTGCTGCTCTTAAAACCGTTG

GAGACCTTCGTCGTCCGCCGTATGTTCAATGGCGTTCTCACTACGATCTC

CTCGACTGGCTCGCCTTGTTCTTCGGTTTCCAGAAAGATAACGTTCGTAA

CCAGCGTGAGCATATGGTGCTTCATCTCGCAAATGCTCAGATGCGTCTCT

CTCCGCCGCCGGATAATATTGATTCTCTCGATTCCGCGGTTGTTCGTCGG

TTTCGTCGGAAACTTCTCGCTAACTACTCTAGCTGGTGTTCGTATTTGGG

GAAAAAATCAAATATCTGGATCTCAGATCGGAACCCTGATTCGAGACGAG

AGCTTCTCTATGTTGGACTCTATCTTCTCATTTGGGGAGAGGCTGCGAAT

CTTCGGTTCATGCCTGAATGTATCTGTTACATCTTCCATAACATGGCCTC

TGAGCTCAACAAAATCTTAGAGGATTGCCTCGATGAGAACACCGGCCAAC

CTTACTTGCCTTCTCTCTCAGGCGAAAACGCTTTCTTAACCGGCGTCGTT

AAACCTATTTACGATACTATCCAAGCTGAGATTGATGAGAGCAAGAACGG

TACAGTTGCGCATTGTAAGTGGAGGAACTACGACGATATCAATGAGTACT

TCTGGACTGATCGGTGTTTCAGCAAATTGAAATGGCCGCTTGATTTGGGA

AGCAATTTCTTTAAGAGTAGAGGCAAAAGTGTAGGGAAAACTGGTTTCGT

GGAGCGCAGGACGTTCTTCTACCTTTACAGGAGTTTTGATCGACTTTGGG

TGATGCTAGCTTTGTTCCTTCAAGCCGCCATTATAGTAGCTTGGGAGGAA

AAGCCAGATACCTCGTCGGTAACAAGGCAGCTGTGGAATGCTCTGAAGGC

AAGAGATGTTCAGGTGAGACTATTGACCGTGTTCTTGACATGGAGTGGTA

TGCGACTCTTGCAGGCTGTGCTGGACGCGGCTTCACAATATCCCCTCGTT

TCCAGAGAGACCAAAAGGCATTTTTTCAGAATGCTGATGAAGGTTATAGC

TGCCGCAGTTTGGATTGTAGCTTTCACTGTCCTCTACACTAACATCTGGA

AGCAGAAGAGGCAAGACAGGCAGTGGTCCAATGCCGCGACGACTAAGATA

TACCAATTCCTTTACGCTGTGGGGGCCTTCTTGGTGCCCGAAATCCTGGC

TTTGGCTTTGTTTATTATCCCATGGATGAGAAACTTCCTGGAAGAGACCA

ATTGGAAAATATTCTTTGCTCTAACTTGGTGGTTTCAAGGCAAAAGCTTT

GTGGGTCGAGGTTTGAGAGAGGGTTTAGTGGACAACATCAAGTACTCGAC

TTTCTGGATCTTTGTCCTAGCTACAAAGTTTACATTTAGTTACTTCCTGC

AGGTTAAGCCAATGATTAAACCCTCAAAGCTGCTATGGAACTTAAAGGAT

GTCGATTATGAGTGGCATCAGTTTTATGGAGACAGCAATAGGTTTTCTGT

CGCATTGTTATGGTTGCCAGTTGTGTTGATATATCTGATGGATATCCAAA

TTTGGTACGCAATCTATTCTTCGATTGTTGGTGCTGTTGTTGGGCTGTTT

GATCATCTGGGGGAGATCAGGGACATGGGACAGCTGAGGCTAAGGTTTCA

ATTCTTTGCTAGTGCTATTCAATTCAACCTAATGCCTGAGGAACAACTCC

TGAATGCTAGAGGCTTTGGTAACAAGTTCAAGGACGGCATTCATAGGTAG

TCCGTGGAAGCATGCTACTAATATTCCTAAATAATTTTCTGTACAACGCT

TGACTTGACTGTACAAGCTGTGAAATTTTACTTTTGTTAACGCAGATGCT

GCATATAATTAAATTTTTCAATATTGTAATAACTTGAGGTTGTGTACTGT

ATGCAGATTGAAGCTAAGGTATGGATTTGGGAGGCCGTTTAAGAAACTTG

AGTCGAATCAGGTCGAGGCCAACAAGTTTGCGTTGATCTGGAACGAAATC

ATCTTAGCTTTCAGAGAAGAGGATATAGTTTCTGATCGTGAAGTAGAGCT

-continued

ACTGGAGCTGCCAAAGAATTCCTGGGATGTGACGGTTATTCGCTGGCCGT

GTTTCTTGTTGTGCAATGAGCTTTTGCTTGCACTGAGCCAGGCCAGAGAG

CTGATAGACGCACCTGATAAATGGCTGTGGCACAAAATATGCAAGAATGA

ATACAGGCGTTGTGCTGTAGTTGAGGCATATGACAGCATCAAACATCTAT

TGCTCTCAATCATCAAAGTTGACACTGAAGAACATTCGATAATTACGGTC

TTCTTTCAGATAATTAATCAGTCCATTCAGTCAGAGCAGTTCACCAAGAC

CTTTAGAGTGGACCTGCTGCCAAAAATTTATGAAACACTGCAGAAATTGG

TTGGGCTGGTAAATGATGAGGAAACAGATAGTGGGCGGGTGGTGAATGTT

CTGCAGTCTCTTTATGAGATTGCAACTCGACAGTTCTTTATAGAGAAGAA

GACAACTGAACAGCTATCTAATGAAGGTTTAACTCCTCGAGACCCAGCCT

CAAAGTTGCTGTTTCAAAATGCTATTAGGCTTCCTGATGCAAGCAATGAA

GACTTCTACCGGCAGGTTAGGCGTTTACACACGATTCTCACCTCTAGGGA

CTCTATGCACAGCGTCCCTGTGAATCTAGAGGCGAGACGGCGGATTGCTT

TCTTCAGTAATTCGCTTTTCATGAACATGCCTCATGCCCCTCAGGTTGAG

AAAATGATGGCGTTCAGTGTTCTGACTCCATATTACAGTGAGGAAGTTGT

ATACAGCAAAGAACAGCTCCGAAATGAGACTGAGGATGGGATTTCCACCC

TATACTACCTGCAGACAATTTATGCTGATGAATGGAAAAATTTCAAGGAA

CGGATGCATAGGGAAGGAATCAAGACAGATAGTGAGTTGTGGACAACCAA

GCTGAGAGACCTCAGGCTTTGGGCTTCCTACAGAGGTCAGACATTGGCAC

GTACAGTTCGTGGGATGATGTACTACTACCGGGCTCTTAAGATGCTCGCT

TTTCTTGACTCTGCGTCTGAAATGGACATTCGGGAGGGTGCTCAGGAGCT

TGGTTCAGTGAGGAATTTGCAGGGAGAACTGGGTGGTCAATCTGATGGGT

TTGTCTCTGAAAACGACCGATCTTCCTTAAGCAGAGCAAGTAGTTCCGTG

AGTACGCTGTATAAAGGCCATGAGTATGGGACTGCATTGATGAAATTCAC

ATATGTTGTGGCGTGTCAGATCTACGGGTCTCAAAAAGCAAAGAAAGAGC

CTCAGGCAGAGGAAATTCTGTATCTGATGAAGCAGAACGAAGCTCTCCGT

ATTGCATATGTGGATGAGGTGCCTGCGGGAAGAGGAGAGACTGATTATTA

CTCCGTTCTGGTGAAATACGATCACCAGTTGGAGAAGGAAGTGGAAATAT

TCCGTGTGAAGCTACCTGGTCCAGTGAAGCTGGGCGAGGGAAAGCCAGAG

AACCAGAATCATGCAATGATCTTTACCCGTGGTGATGCTGTTCAGACCAT

TGATATGAACCAAGACAGTTATTTTGAGGAAGCTCTCAAGATGAGAAATT

TGCTCCAGGAGTACAACCATTATCATGGTATCAGAAAACCAACTATTCTT

GGTGTCAGGGAGCATATCTTCACGGGATCAGTCTCGTCACTGGCGTGGTT

CATGTCTGCTCAGGAGACAAGTTTTGTCACTCTTGGTCAGCGTGTTCTTG

CAAACCCACTGAAGGTCAGAATGCATTATGGCCACCCTGATGTATTTGAC

AGATTCTGGTTCTTGAGTCGAGGCGGCATCAGTAAGGCTTCCAGAGTTAT

AAATATCAGTGAGGACATCTTTGCCGGGTTTAACTGCACGTTAAGGGGGG

GAAACGTCACCCACCACGAGTACATTCAGGTTGGGAAGGGTCCACAATTT

GGATTATTTCTAACTAACTATACTGCTACAACGTTTTTTTAACGTTTTTA

ACGTTTATTAATTATGCAATCTACTTTTGTTATAATTATGTAATTTAACG

-continued
```
TTTTTTAATCTTCTAAATTCAAAAAATTTGAGTAACCTTTGTCTTTATGC

ATTTTTCAGGTCGGGAAGGGACGGGATGTTGGATTGAATCAGATATCAAT

GTTTGAGGCTAAGGTAGCCAGTGGGAACGGAGAGCAGGTTCTCAGCCGAG

ATGTGTACCGGCTCGGGCACAGGCTTGATTTCTTCAGAATGTTATCATTT

TTCTACACAACTGTAGGGTTTTTCTTCAACACAATGATGGTCATTCTTAC

TGTTTACGCTTTCCTCTGGGGACGGGTTTATCTGGCTCTCAGCGGGGTTG

AGAAGTCCGCTCTAGCAGACAGTACGGACACCAACGCCGCGCTTGGGGTG

ATCCTGAACCAGCAGTTCATCATTCAGCTCGGTCTGTTCACTGCCCTGCC

AATGATTGTTGAATGGTCTCTCGAGGAGGGTTTCCTTCTAGCGATATGGA

ATTTCATTCGAATGCAGATTCAGCTTTCAGCTGTCTTCTACACATTCTCA

ATGGGGACCAGAGCTCACTATTTCGGTCGAACTATTCTCCATGGTGGGGC

CAAGTATAGAGCCACTGGACGTGGATTTGTTGTCGAGCACAAGGGATTCA

CTGAGAACTACCGACTGTATGCACGCAGTCACTTTGTGAAGGCCATCGAG

CTTGGGCTGATCCTCATAGTCTACGCTTCGCACAGTCCGATTGCCAAAGA

CTCGTTGATTTACATAGCCATGACTATCACCAGCTGGTTTCTTGTGATTT

CATGGATAATGGCCCCATTTGTGTTTAACCCATCAGGATTCGACTGGCTT

AAGACAGTCTATGACTTTGAAGACTTCATGAACTGGATCTGGTACCAAGG

CAGAATCTCAACGAAATCTGAACAAAGCTGGGAAAAATGGTGGTACGAGG

AACAGGACCACCTGAGAAACACCGGGAAGGCAGGATTATTGTGTGGAGATC

ATCTTGGTCCTCCGGTTTTTCTTCTTCCAGTATGGGATTGTATACCAGCT

TAAAAATTGCAAACGGATCCACCAGCCTTTTTGTCTACTTGTTCTCATGGA

TATACATCTTTGCTATATTTGTGCTCTTCCTAGTCATCCAATACGCCCGT

GACAAGTACTCGGCAAAAGCTCACATACGGTACAGGCTTGTCCAATTCCT

CCTGATCGTGCTTGCTATACTGGTGATTGTTGCTTTGCTCGAGTTCACGC

ATTTCAGCTTCATCGATATCTTCACAAGCCTTCTTGCATTCATCCCAACT

GGCTGGGGAATTCTGCTGATCGCACAGACTCAAAGGAAGTGGCTGAAGAA

TTACACTATTTTCTGGAATGCTGTTGTCTCTGTTGCTCGCATGTATGACA

TATTGTTTGGGATACTCATAATGGTTCCAGTAGCGTTCTTGTCATGGATG

CCTGGATTCCAGTCAATGCAAACGAGGATATTATTCAATGAAGCTTTTAG

CAGAGGACTTCGCATCATGCAGATTGTCACTGGGAAGAAATCAAAAGGCG

ATGTCTAAGTTTAAAAAACGGTAAAGCTCCTTGTTCTCAACACCTTATGT

TATGATCGTTTAAATCCTGGATTTCACACCAATGCGGGCTTTAAATTTGT

GTAGGTCTTAAGAAGTAAATGGTAGTTCAAATCCTATTGGTATGTGGCGA

AGGAATCAGTTGGAGGTTAGTTTTCCCGAAACAACCGAATTCGAAGTTTT

GTTTCGTCTAAAGAAAAACTCAGATGCTGATGATTTATCTTTGTATTTTA

AACAGGTTTTTGGAGAGTTTGGTTGGATGAGGAATCGGGAAGTTGGTTTG

ATTCGGTTAGATGGGTTTAGGGAGATATTTGATTGTCAGTGTGTGTGGAG

GGAACTCTGATTCTTGTATGGTTTTTGTTCTAAAGGTACAGCAATTTGTG

TAGTGAGGCTTTGTGTATTTGTTCTCCTTCTCTCATTATAGAGCTTTAGA

GCATTTTTAGTTTATATTCAGATTGTTATCTAATGTCATCTCGCAGAGCT

TTTGTTCACATTTCACATCTTTTCTTCTCCTTCTTAGTAGAGATCAGTTT
```

-continued
```
CAGATTAGATACTTGTCCATATTCCACTACTCTCGTCTATTATCGGTTTC

TGCTTGTCAATTTCTGGGTCCAAAATTGAAATA
```

SEQ ID NO. 2
```
CTTCCTTCTTTGCCGTCTCTCTTGAAGCTAAGTACACCGATATGGCCGCC

TTTAAGTATGTTAAATGCAAACACAAATCGATTATGTTCATCTCATAAGT

TATGTGAATATTTTTAGCTAGTAATTGGGTATAACATGTTTTGTAGGTAT

TTTGTGATCGCAAACGCTGTCGTGAGTGTTTACAGCTTTCTAGTTCTGTT

TCTTCCTAAGGAGAGTTTACTGTGGAAGTTCGTCGTCGTCTTGGATTTGG

TAATAATTGTTATTTGGTTTAGTACTTCTCTTCGTTCATTAATTCATTTG

CATTCTATCTCTAAGCATAGTTTTTTTCTAAAGGTAATATTATTGTTGAT

ATCTAGTAGTTTGATGTGTTCAGAGGAATAAAAGCATTTTTATTGGTGAA

ATACTGAAAAATAATAAAATGTTGATTATTATAGTTCAAATAAACAATTG

TTTTCTAGAAGAACATAAAGTAATCACAATATTATATTTTGCATGAGAGT

TTTTTCACGAAATTCTCATATTTCCTCTTATTATCATTTATCGTTGAGAT

ACTTTCTAAGAACTCTTTAATGGAGATGTTCTAGTAAATTAATCTTTGAA

CGAAAAGTTAAAACATACACTTTCAAAAAAAAAAAGTTAAAACAAATAAA

CTTGAATGTAATGTGTCTTAGTCACACGCTTATTATAGGTTGTTAGGTGA

CGACTATATCAGCATACATACGAATTGTCATTAACTTTTGACATTTTTGG

TGAATGTATTGGAGGTGATGACAATGCTACTAACGTCAAGCATATCAGCG

GCGTTAGCGGTGGCGCAAGTGGGAAAGAAAGGAAACGCAAACGCAGGTTG

GCTTCCAATTTGCGGCCAAGTTCCAAAGTTTTGCGATCAGGTCACCGGAG

CTCTCATTGCCGGCTTCGTCGCACTCGTCCTCTACGTCTTGTTACTCTTA

TACTCTCTTCACTCCGTCGTCGATCCTTTTCTTCTCCAGAAATCTTGAAT

CTAACTTCTTTTTTCACTTTCAGTATCGGTTAATATACGTTTTAATATCT

ATACTATAACGTCGTTTGTGTATTGTATTTATATGTTTTCTGTTTTAGGT

GTCGAGATTGTCATAGTATTTCATTTTTATGGACTAATTAACATTATAGA

CTGAACCACCTCTCATAAACTCTTACTCATAATTAAAAAAAAAAAATCAAT

GCTTCATATATACATCTCTGTCAATCATTGGATTCGTATTTATTATAGTA

TCAACAAATTTGTGATACAAACCTAAACATGTGCAATATCTTTAGCTAAC

GAAATGGATATAGATACATCTTCCCTAGCTATGGAAATGAGTATTTGATC

AAAACGTAATTGCACTTGTTAGTTAGTCATTTCTCTCAGTGTAACAAAAC

ACCATTTATGAAAAAACACTGAGCATGGGCAAGTTTCGTCTTCACCTCCG

TTAATCTTTTGCATCGTAAAAACAATCGATGTTACAAAACATGTTTTGTT

TTAACGTTGTAAAAATATCAGGCTTGATTTGAATGTCATGTTATGCCGAC

TTTACTAGTTTGTGTAACCAACTAAGCTATTAAAATATGCGTAATTACAA

AACTGTCAGATTTAGTTTCACAAAATCTTTGTAACTTCGCGGTTTTTGAT

ATGGAAGTTGCTACAAAAACTGACTTGTGATATTATAATCTTTCGGCAAG

AAAAATATATAATACTAATTTCAGAAAGTATTCTGTTGAATTGTTGATCA

CCAAATACACATAAACCGGCAGATGTTGACATGTTTACGTGGGATCACTG

GGATAGAAGTTTTGCTTCTGTATTAGTATCGCGAACCGGTTTGTAGTAGC

GAAAATAACATTATTATTTTCAGATTTCATCATCGTCAAATTCAACGTTA
```

-continued

```
CATTTGAACAGGCTTGTAAAAAGTGGACATGTGGCATGAGTAAAAGATAA

AGAAAATTGTGAGCCTTTTTGTTAATACGAAAAAGCCGAAAACGTTATTA

TTTCTATCATCGGCAAATTTAATGTTAAATTTGCTCCACATCATTCAGAG

GGTATATGTATATTTTTCTAATGCTTCGGTGAAGCACATGCGACCATTTG

TTGCGTCAGAAGTCAGAACAAAAGGAAGATTCCATCTAATGGATTATAAT

CCCACATGCCCATTTTTAAAACTAGACAAAATAACTTATAATAGTCCCAT

AAGAGCATTAAGACAAACTGAACCAAAAAGAATCTTAAATGCTGGTGAAT

CTAGTCTCGAATGCTGCTGAACACTCCTGATATTAGAATTTGGCAGAAAA

TATTCATACTAATAACAGTAAATACATTTCAAAACAAGAAAATAGTAGTA

GTAAATAAAAACAATTAATATGTTATTATTGTTTCTCTTAGCTGTTACCA

TTACATTAACAATTTACATTCAATCCTTTTAATGAAAAATATTATAAAAT

ATTAAAAGAAGTTATTAGAAAAGGAGAGGGATATGGGGGGGGGGGGGGGA

GAGCATGGAGGGGTCCCATGTGTGTTTCGAAAAGCAGCAAACATGACTTT

GTAAAGTCTTGTTTTAGCTAGAGTTCCAAAAAAAAAAAGAGTTCAAAAAAA

AAGAAAAAAAAAGTCTTGTTTTAGCGTCCAAAGCGGTCTCACTCGCCGT

TCAGCTGTTAAATTTTCTTGAAATAAATCGCTCCACTTGTTTTTTATTTT

TGTTTCTTTCAACCCACTTGTATTAATAACAATAATGATATTGCTAATCT

TGAACAAATCGTGGATTGTCTTTTCTTCCAGTGATATCATCCTTAGTCAA

AACATCTCAAATTAAATAAATATATAGTTGTGAATTAAAAAAAAAGGTAT

AGAGTTTATAAAATTAGCATTTGCGAATGTTTTTAAAAGTTTGGCGTTTG

TATAGATCACTGTCAGTGTCATGAATCATTCGGTGACAGCAAATTTGTAT

ATGCCAAAAAAGAGAGTTGATACTTGCCATTCTCGATATTTTGAATTTTT

TTTCGTCGACATACAAACTCAACATTTTCGAAATCTTAGATTAAAAACAA

AATGGACAAACGATACTTATTAATGAATTATGTACTAGCGTCTAAACAT

TAGTAACATAGATATAATTATAAGAACAAGAAACATATATGCACAAAGCC

TCAAACCAAATTTAAATAGTGTTACGAAACAAGGGATGTACTTGTTATGA

AAAATTAATGTATAACCATTCTTAGCATTTTTTACCTAACCCTTAAACTT

TATAAAGAAAAATATGTAACATTTCGGTGTGTGGTATATAAAAGTATTTT

GAAAATCGATTTGATTATTTCTATTATTAAAATGTACTTACTTTTTTTAT

CACACATTTATTTACAATTTCAGAGTTAAACATGATTAAGACAAAGTAGT

GAAAATATAGATGATCTACCAGAAAATCATTTGCTTTCTGAGTGAGATCA

AAATAAAGGCAAAATAATGTGATGATTGTATATTAAACAATTATTTTGA

ATTTGAAAAGAATAACTCATCGAATGAAGCCTATGAACCGAGTAAGCGGT

GAAGCGGTTGGACCGTCACAAAAATTATGACCAACAAGAAAATAAAATTG

ATATTAGTGAATGATATATTTTGGAAAGTAATAAATTGGTTCCAGATTTC

AATACATCAATGTTTTTCTAATGCTGACTTGCTTTTCCTCTTTTTCTTAC

ATGATAAGGAAACGAGAGAGGTCGAAGAAACAAAGAAACTTCCTAAGCAT

TTAGCAACGCATCTTCAAAAAATCTAGTATTTACCAAGTAAAATCATACA

AAATAAGGAAAAAAAGAAGAATATATTTCCCAATTTGGTTTTCACCCGAA

AAAAAAACTGTCTTAACAAAATCTTAATGCACCAAATCATATAAGAACTT
```

-continued

```
TATTTGACCATTGTCATTAGTTTTTTTCCTTATGGTAATGGATCTTCAAAT

AATTTAAATTAAATTAAAAAAAAAAAGAAAAGAGAAACAAAAACGCGGAAA

GGAGAGCCCAAATCGTCTCCGTCTGTCATTGTCGCAGTCTCTAAAAGAGA

AAAACAAATCGCAACGCTTCTCTCTCTCTCCCTATCGTTTGAATCAGTCT

CTCAAGATCCACCACCACCACACATGCTACTATGAGCCTCCGCCACCGCA

CCGTCCCCTCTCAACCCGGACGGCCCCCGGCGGCGGGCGCAATCGAGGAC

GAGCCCTACAACATCATCCCCGTCAACAACCTCCTCGCCGACCACCCCTC

CCTCCGCTACCCCGAGGTCCGCGCCGCCGCCGCCGCCCTCAAAACCGTCG

GCGACCTCCGCCGCCCCACCTACGTCCAATGGCGCCCCCACTACGACCTC

CTCGACTGGCTCGCCCTCTTCTTCGGCTTCCAGAAGGACAACGTCCGCAA

CCAGCGCGAGCACCTCGTCCTCCACCTCGCCAACGCCCAGATGCGCCTCA

CCCCGCCGCCGGACAACATCGATTCCCTCGATCCCGCCGTCGTCCGCCGC

TTCCGCCGCAAGCTCCTCGGTAACTACTCCAGCTGGTGCTCCTACCTCGG

GAGGAAGTCCAACATCTGGATCTCGGATCGGAGCCCCGATTCGCGGCGGG

AGCTTCTCTACGTCGGCCTCTACCTCCTCGTCTGGGGCGAGGCGGCCAAT

CTTAGGTTTATGCCTGAGTGTATCTGTTACATCTTCCACAATATGGCCTC

GGAGCTTAACAAGATCTTAGAGGATTGCCTCGACGAGAGCACGGGGCAGC

CGTATTCTCCTAAGATCACGGGGGAGAATAGTTTCCTAAACGGCGTCGTT

AAGCCTATCTACGACACGATCAGAGCTGAGATTAATGAGAGCAAGAACGG

GACGGAGCCGCATTGTAAGTGGAGGAACTACGATGATATTAATGAGTACT

TCTGGACGGATAGGTGTTTTAGTAAATTGAAATGGCCGATTGATTTGGGG

AGCAGTTTCTTCAAGAACAGCAGAGGTAGCGGAGTTGGGAAGACAGGTTT

TGTGGAGAGGAGGACGTTTTTCTACCTCTACAGGAGCTTTGATAGGCTTT

GGGTGATGCTTGCTTTGTTTCTTCAAGCTGCTATTATAGTTGCTTGGGAG

GAGAAGCCGGGTGGAGGGTCGGTGACGAGTCAGCTCTGGAATGCGTTGAA

GTCGACGGATGTTCAGGTGAGGCTTTTGACTGTGTTCTTGACGTGGAGTG

GGATGAGGTTGTTGCAGGCTGTGTTGGACGCTGGCTCGCAACGGTCTCTT

ATTTCTAGAGAGACCAAACGGCTGTTTTTCAGAATGTTGATGAAGGTTGT

GGCTGCTACGGTTTGGATAGTAGCGTTTATTGTTCTCTACACGAACATCT

GGAAGCAGAGGAAGCAAGATAGGCAGTGGTCCAGAGCCGCGAATGATAAG

ATCTATCAGTTCCTTTACGCTGTGGTGGCTTTCTTGGTTCCTGAGATCCT

GGCTTTGGCTCTGTTTATAGTCCCGTGGATAAGGAACTTTCTGGAAGAGA

CGAATTGGAAGATATTCTTTGCTTTGACTTGGTGGTTCCAGGGGAAAAGC

TTTGTGGGTCGAGGTTTGAGAGAGGGGTTGGTGGACAACATCAAGTACTC

GACTTTCTGGATCTTTGTCCTTGCAACGAAGTTCACGTTCAGCTACTTCC

TGCAGGTTAAGCCAATGATTAAACCCTCGAAGCTGCTATGGAATTTGAAG

GAGGTGGATTATGAGTGGCATCAGTTCTTTGGCGAGAGCAATAGGTTTTC

TGTCTTGTTATTGTGGCTGCCAGTGGTGTTGATATACCTGATGGATATCC

AAATTTGGTACGCGATCTATTCTTCGATTGTTGGTGCTGTTGTTGGGCTG

TTTGATCATCTGGGGGAGATCAGGGACATGGGACAGCTTAGGCTGAGGTT

TCAGTTCTTTGCTAGCGCTATTCAGTTCAACCTAATGCCTGAGGAACAAC
```

-continued

TCCTGAATGCTAGAGGATTTGGTAACAAGCTTAAGGACGCCATTCATAGG

TAAGTCTATTGAAGCATGTTACTGATATTTCTATATAATTTACTATATAG

AGTTTGTCTTTAAAGTACAAGCTATAGTATTTTAGTTTTGTTAAAGCAGA

TTCTCCGCAATGAACTCGACTTTTTCACATTGTAATAACATTGAGTTTGT

GTACTTTATGCAGATTGAAGCTGAGGTATGGATTGGGGCGGCCGTTTAAG

AAACTCGAGTCCAATCAGGTTGAGGCTAACAAGTTTGCGCTGATCTGGAA

TGAGATAATCTTAGCTTTCAGAGAGGAGGATATAGTCTCTGATCGAGAAG

TAGAGCTGCTGGAGCTGCCAAAGAATTCCTGGAATGTGACAGTTATCCGC

TGGCCGTGTGTTCCTGTTGTGCAACGAACTTTTGCTTGCACTGAGCCAGGC

GAAAGAGCTGGTTGACGCACCTGATAAATGGCGTGGCACAAGATATGCA

AGAATGAGTACAGGCGGTGTGCTGTGGTTGAGGCATATGAAAGCATCAAA

CATCTGTTGCTCTCAATCATCAAAATTGACACTGAAGAACATAAAATTGT

TACAATTTTCTTTCAGATGATTGAGGTGTCTATTCAGGGTGAGCAGTTCA

CCAAGACCTTCAAAGTGGACCTTTTGCCAAAGATTTATGAGACACTGCAG

AAGTTGGTTGGGCTGTTGAATGATGAGAAAGTGGATGTTGGGCGAGTGGT

GAATGGTCTGCAGTCTATTTATGAGATTGCAACACGACAGTTCTTCCTAG

AAAAGAAGACGACTGAACAGCTATCTACTGAGGGGTTAACTCCTCATGAT

CCAGCCTCAAAGTTACTGTTTCAGAATGCTGTTAGGCTTCCCGATGCAAG

CAATGAAGACTTCTTCCGGCAGGTTAGGCGGTTACACACAATTCTCACTT

CTAGGGACTCTATGCACAGCGTCCCTGTGAATCTAGAGGCGAGACGGCGG

ATTGCCTTCTTCAGCAATTCGCTCTTCATGAACTTGCCTCATGCACCTCA

GGTGGAGAAAATGTTGGCGTTCAGTGTTATGACTCCATACTACAGCGAGG

AAGTTGTATACAGCAAAGAACAGCTCCGAAATGAGACTGAGGATGGGATT

TCAACCTTGTATTACCTGCAGACGATTTATGCCGACGAATGGAAAAATTT

TAAGGAACGGATGCGTAGGGAAGGTATAAAGACAGATGTTGAGTTGTGGA

CAACCAAGCTGAGAGAGCTCAGGCTTTGGGCTTCCTACAGAGGTCAGACT

TTGGCACGTACAATTCGAGGAATGATGTACTATTACAGGGCTCTTAAGAT

GCTTGCTTTTCTTGACTCTGCGTCTGAAATGGACATTCGGGAGGATGCTC

AGGAGCTTGGTTCAATGAGGAGTTCGCAGGGAAATCGATTGGATGGGGTG

GACGATGTAAATGACGGATCTTCTCTAAGCAGAGCAACTAGCTCTGTGAG

CATGCTGTATAAAGGCCATGAGCATGGGACTGCATTGATGAAATTCACAT

ATGTCGTGGCGTGCCAGATCTATGGGTCTCAAAAAGCGAAGAAGGAGCCT

CAGGCAGAGGAAATTCTGTATCTTATGAAGCAAAACGAAGCCCTCCGTAT

TGCATATGTGGATGAGGTGCATGCGGGCAGGGAAGAGACTGAGTATTACT

CCGTTCTGGTGAAATACGATCACACGTTGGAGAAGGAAGTGGAGATATTC

CGTGTGAAGCTACCTGGTCCGGTGAAGCTGGGTGAGGGAAAGCCAGAGAA

CCAGAATCATGCAATGATCTTTACCCGCGGTGATGCTGTTCAGACCATAG

ATATGAACCAGGATAATTATTTTGAGGAGGCTCTCAAAATGAGAAATTTA

CTCCAGGAGTTTAGGCATTATCATGGGATCAGAAAACCAACTATTCTTGG

TGTCAGAGAGCACATCTTCACGGGTTCTGTCTCGTCTCTGGCTTGGTTCA

-continued

TGTCTGCTCAGGAAACAAGTTTCGTCACTCTGGGTCAGCGTGTTCTAGCC

AACCCGCTGAAGGTCAGAATGCATTATGGTCACCCTGATGTATTTGACAG

ATTCTGGTTCTTGAGTCGAGGTGGCATCAGCAAAGCTTCTAGAGTTATAA

ATATCAGTGAGGACATCTTCGCCGGGTTTAATTGCACATTGCGGGGCGGT

AACGTCACCCACCACGAGTATATTCAGGTAGGGAAATGTTCATCATTTGG

ATATTCTAACTAATTTTATACATCGACAACAATACTATAATTCCACTTTT

TTTGTTATAACCTTTTTGTGTGTGCATATGTATTCAGGTTGGGAAGGGTC

GAGATGTTGGATTGAATCAAATATCAATGTTTGAGGCTAAGGTAGCCAGT

GGGAATGGAGAGCAGGTTCTTAGCCGAGATGTGTACAGGTTGGGTCATAG

GCTCGATTTCTTCAGAATGTTATCATTTTTCTACACAACGGTGGGGTTTT

TCTTCAACACGATGATGGTCATTCTCACTGTCTACGCTTTCCTCTGGGGC

CGGGTTTATCTTGCTCTGAGCGGTGTTGAGAAGTCCGCTCTAGCAGACAG

CACAGACACCAACGCAGCGCTTGCTGTGATATTGAACCAGCAATTCATCA

TTCAGCTTGGTCTCTTCACAGCTCTGCCAATGATTGTGGAATGGTCTCTC

GAGGAGGGTTTCCTTCTCGCGATATGGAACTTCATTCGGATGCAGATTCA

GCTTTCCTCTGTCTTCTACACATTCTCAATGGGGACCAGAGCTCACTATT

TTGGCCGAACCATTCTCCATGGTGGAGCAAAGTACAGAGCCACTGGGCGT

GGATTTGTTGTCGAGCACAAGAGCTTCACTGAGAATTACCGTCTATACGC

ACGCAGTCACTTTGTGAAGGCCATCGAGCTTGGGCTGATCCTCATAGTCT

ACGCTACGCACAGTCCCATCGCCAAAGACTCATTGATCTATATAGCTATG

ACTCTCACCAGCTGGTTCCTCGTGATATCATGGATACTGGCCCCTTTTGT

GTTCAACCCGTCAGGATTCGACTGGCTTAAGACGGTCTACGACTTCGAAG

GCTTCATGAACTGGATCTGGTATCAAGGCAGGATCTCAACGAAGTCCGAA

CAGAGCTGGGAGATATGGTGGTATGAGGAACAGGACCACCTGAGAACCAC

CGGTATACCAGGAAGAATCGTGGAGATAATCTTGGACCTTCGGTTTTTCT

TCTTCCAGTACGGGATTGTATACCAGCTCAAAATCGCAAACGGATCAACC

AGCATTCTCGTCTACTTACTCTCATGGATATACATCTTCGCAGTGTTTGT

GTTCTTCCTAGTAATCCAATACGCCCGTGACAAGTACTCTGCGAGAAACC

ACATACGGTACAGGCTCGTTCAGTTCCTCCTGATCGTGTTTGGTACACTG

GTGATTGTTGCTCTCCTCGAGTTCACGCATTTCAGCTTCGTGGATATCTT

CACGAGTCTTCTTGCGTTCGTCCCAACCGGCTGGGGGATCTTGCTGATCG

CACAGGCGTTGAGGCCTGCGCTGCAGAAGATCGGGCTTATCTGGAACGCG

GTTATCTCCCTTGCTCGGTTATATGACATACTGTTCGGGATAGTCATCAT

GGTTCCCGTAGCGTTCATGTCGTGGATGCCTGGGTTTCAGTCGATGCAAA

CGAGGATCTTATTCAATGAAGCTTTTAGCAGAGGGCTTCGTATCATGCAG

ATTGTCACTGGGAAGAAATCAAAAGGCGATGTCGAAGTTGAAAAAAGAAG

GTAAAGCTTCTTATTTACCCAAACATCTTTTTATGTTCTGTTTGTTTGGA

ATCTTAAATTACAACAACACTAATGCAAAGCTTTTACAACTTGTGTAGGT

CTTGAGGTATATGGTAATTTAAAAGTTGCTGGTTTGCGGCGATGTGACCT

GTTGGAGGTTAGTTTTGTATTCTTACAAGTTATGCTTCTTGTCTGAATAG

GAACTCAGACACCCGTGTTTTGTCTTCTTCTTATTAAACCAGGTTTTTGG

AGAGCTTTGGTTGAGGAAGCTATTCGATTAGATAAATCTTTTAGTGGGGG

AGACATATATATATACATTTGTCAGTACTTTGTTAGTGTGTGGAAGTGGG

GACGACTCTGATTCTGATTCCTTATGTGGTTATTGTCTGAAACGTTACAG

CATTTTGTGAAGTAGGCTTTTGTGCAAGATTTGATCTCTTTCTCTCATTG

TAGAGCTTTAGAGCATTTTTTAGTATATGTTTAATCTTTGATTTTCTAAT

GTCATTTGCATTCATATTCACATCTTCTTCGTTGGTCTTAAACCAGTTTT

CAGATGCTTATCCATTGTCCACTTCTCTATGTATCTGTTTCTTCTGTTTG

TTTTCAGTATTGTCTTTTATTCTTTAATCAGTTTTATTTGGACC

SEQ ID NO. 3
AGTGAGTTTGTTCTCCAGCGAGCCGGAGAAGGCATCAACGCAAACCTGGA

GGAACAGATTGACCGGTATGTTCATTAACGCTGCAAGCCAGCTTTGATGT

TAGCTGCGTAAAGATCCCTGCGTTTACATCAAAACATTACATTGTTTGCT

GTGACTAAGGTAACAGAGTAAACGTGTAAAATACTCTGGTGTTTTGGAGA

AAACAAACTTACATGGAGCCCTTAATTGCATCTATGGCAGCTTGTGCTGA

GAGGAAACCTTCAACGTCCACTTTTCCTTGTAGGTTACTAATATATGCAT

ATTTTATTTAAATCAATCCAAATATATGGGTAAAAAACTTTATTTGAGGA

TGTACTATATATGAATGCCTAAGAGTATAATGTACAAAGGTGAAACTT

GCCTTGACATTGAAGGAGTAGAGGACTGTTTGCTCCATGGTAGTCATGTA

AGTGTGAAGAATAGAGAGATGAAGATCCTCCAAAAAAGCAATAGTCTTAA

TAAGTTGTCCTGGTCTTCTTCTTGAAAGTTTCTTGATCATGGCATCAAAC

TCTAGCAGCTTCACCTCCACATCAGCCAAGCACGACTCGTTCTCAGCTGT

TTCTTCCCGGAGCCCTCCTCCTCCTCCTATACGACTCATGTGACTCTAGG

CATTGTAGAAGTTGCTCAAGCTCTCTTACAAACTCTATTCCACCTATGAT

CGACGCTTGATCTCTCTGTTATATACATGCATATTAAAAAATATTTTAAA

ATAATGAATACAATCACGAAATGAAGATGTATATGTGTTATCATGATACC

CATTGAACGTAGGATCCAGACAAAAGAGACTTGAGGTTACGAAGATGCTC

GTTCATTTGCTTCCTATTCCTAGCGACCGCAATATGTCTCATTCGTTAGT

TTTCTACTTCTTCGCTTGTCTTGCTTGTTTTTGCTCTTCACCTCCTTTGT

CATATCATTCTTGTTCTCACTATCTCCTTCTTCTCCTCCAGTAAACCGAC

TTGTTATTGTCGTTAACGTCTAAGGATTCACCTAAAAAATTTGGTGCCTG

AAAGAAAATAAAGGTGAAGAAATAATTATTAAGATAATATAGGTCAATTG

ACTTGGAATCAAAATTTTCACCCTGCAAGTTGACATGGTTTCATACTAAT

GTGATACATTAAGACATAGTTTATGGTTTTAATGATTGTTACCTGATCCA

TCAGGCATTATACCAAAAGGACAGGCACGGAGGAACTATTCAGTTAGCCC

ATGCTCCTGCACAAATTTATCAATCAACTCATATCTAGAAGGATATATGA

GAAAAGAAGTTTCTGGTGTTATTAGGAGTTGTGAGGATGATGTTTATTAA

GAAATAAACTATATAAGCCTTTACATATAAATTACAAAATACCTTGATTC

TCATCCAAGATTCCGGTGTGGATCGATTTATCAATGACATATTTGCAAAA

AAAAATAATAGGGTTACCTGGAAGATGGGTGTTGGTGTTTGCTAGACCAA

GCAACTCATCTTTGCAGAACCTGAAACGTTCTTGAGGAATTGGTGAACCT

GGGTCAGTTAAGTCTTTCAAACCCGTCTCAATATTGAACCGGATCGACAC

AGGAGAGTCGGACAGCTTGAAGTCCGGACAGCTCAAAGCCGCTAACAGAG

TACACTTAACCAACAGTGAAAAGATGTCTGAATGTGTTTAAGCGGTAGAC

GTTCACGGTGGCTTAGGTGAGAGTGGCCTGCAAAGCATGAAAAATTGGAA

ACATAAACAAATGAAATAAATATTGCAATCATTAAAAATAAACTAAAGCG

CTTGTTAACTTTTTCATAATCAAAAGACATAAGCATATGGATGTCTCTAC

ACGGACTATTTGAATTTTAGGTATGAATAAAATATACGAAAAAAGTAAAA

AAGAATCAACAATCACAACAATGATCATATCCCAAATATTTGAAGATAAC

AAAAACTTATGGAGAATAACGAAGACATGAATGTATTGATCTCCGGTGAA

GAACTATTAGGTTTGAAAGTTTCATAACCAAAACACAACAACGCGAGAAA

GGATTAAAAAACAAAACAAAACTACATAGTCAAGCCGGATTTACCTTGGC

GTCCATGAAGAGAATGTTGACCCTCTCTGTCGCGCTTAACATTCCTATCT

TCCCAGAACCTAAGCAAACGGACCTGGGCGGTGGAGGTGCAGCGGCTAGC

TTTCAAATCGGCGAGAAAGACGGAGGAATTAGCCATTATCGACTTTGATT

TCTTAGAAAACAGTTTATGGGAATGTAGTAGGATTGTGAGAATGATGTTT

CTGGGAAGAGCACATACCTTTTTGTAGGAGGAGCTTCACCGCTTGTAAGA

GAGATGAGAGTATTGAGTGAGAAATCGTTGAGCTTCATCGTGGAGGATGG

ATTTAAAAAGGGCTTTAAGAGTAAGAATCTGTAACAGGTAGATTGCTGGA

TCCGTAGGAAGAAGATGAAGCATCTCGATCAAAACCCTAGGGTATGATAT

TGCAACGGCGGAGAAGAGAATGAGATGAAACCATAGAATTAAAAACTCTG

CGTTTCAGGCATACGTCTTACTCTGCTTTTTAAAGATTGGGCTTTATAAA

CCAAAACAATAACAAAGAATGTAGCCCAAACGGAAACAGAATAAATGAAA

CGCGGTAAAGTGAACAGATGTCACATAATGATTGGCTGATTTAATTGTCC

TACGTGGACAGCTTCTCTGATGCTCATATAACCCTTTTAGTATAGGTTAG

ATGATATCATCCTTAGTCAAAAGTCAAAACATCTCAAATTAAATAAGTAT

AGAGTTGTGAATTTTTAAAAAAGTATAGAGTATATAAAATTAGCATTTGC

GAATGTTTTTAAAAGTTTGGCGTTTGTATGGATCACTGTCAGTGTCATGA

ATCATTCGGTGACTGCAAAATTTTATATGACAAAAAAAAAAGAGAGTTGA

TACTTACCATTCTCGATATTTTGAAATTTTTTTCGTCGTTAATACAAACT

CAACATTTTCGAAATCTTGGATTAAAAAAAAAAAAATATGGACAAAACGGT

ACTTATTAATTAATTATGTACTAGCGTCTTGACATTATTAATATAGATAT

AATTATAAGAACAAGAAACGTATATGCACAAACCCTCAAACCAAATTTAA

ATAGTGTTAAAAAACAAGGGATGTACTTGTTATGAAAAATTAATATATAA

CCATTCTTAACATTTTTACCTAACCCTTAAACTTTATAAATAAAAATACG

TAATATCCCGATAGAAATATTTTAAAATTTTGATTTGATTATTTATGTTA

TCAAAGTGCATTTATTTTTTTTTGTCACGTATATATTTAAAATTTCAACA

TTAAAAGTGTGTAAGATGGAGTAGTGAAAATATAGACGACTTACCATAAA

ATTATTTGTGATATCATTTGAATAAGACTAAAACACGGACAAAATAATA

TAGTGATTGCATTGTTATTAAACAATTATTTGGATTTGAAAAGAAATAAC

TCATTGAATGAAGCCTATGAGCCGAGTAAACGGACGTGGATAGCTTAAGC

GGTTGGACCGTACAAAATTTATGACCAACAAGAAAATGAAATTGATTTTT

-continued

```
TTTTTGACGAAAAAATGAAATTGATTTTAGAAAGTAACAAAATGGTTCCA

GATTTCAATACTTCAACGTTTTTTTATGCCGACTTTCTTTTCCTCTTTTA

CTTACATGATAAGGAAACGAGAGAGGTTGAAGAAACAAAGAAACTTCCTA

AGCATTTAGAAATGTATCTTCAAAAAATCTAGTATTTACCAAGTAAAATC

ATTCAAAATAAGGAAAAAAAGAAGAATCTATTTCCCAATTTGGTTTTCAC

CGAAAAAAAAATTGTCTTAATAAAATCTTAATGCACCAAATCATATAAGA

ACTTTATATGACCATTGTCATTAGTTTTTTCTTTATGGTAATGGATCTTC

AAATAATTTAAATTAAATTAAAAAAAAAAAAGAGAAACAAAACGCGGAA

AGGAGAGCCCAAATCGTCTCCGTCTGTCATTGTCGCAGTCTCTCACAGCT

AAATAAAAGAGAAAACAAATCGCAACGCTTCAATATCTCTCTCCCAATC

GTTTGAATCAGTCTTCCTCATCACAATCCCCCAAAGATCCACCACACATG

CTACTATGAGCCTCCGCCACCGCACCGTCCCCTCTCAACCCGGACGGCCC

CCGGCGGCGGGCGCAATCGACGACGAGCCCTACAACATCATCCCCGTCAA

CAACCTCCTCGCCGACCACCCCTCCCTCCGCTACCCCGAGGTCCGCGCCG

CCGCCGCCGCCCTCAAAACCGTCGGAGACCTCCGCCGCCCCCACCTACGTC

CAATGGCGCCCCCACTACGACCTCCTCGACTGGCTCGCCCTCTTCTTCGG

CTTCCAGAAGGACAACGTCCGCAACCAGCGCGAGCACCTCGTCCTCCACC

TCGCCAACGCCCAGATGCGCCTCACGCCGCCGCCGGATAACATCGATTCC

CTCGATCCCGCCGTCGTCCGCCGTTTCCGCCGCAAGCTCCTCGGTAACTA

CTCGAGCTGGTGCTCGTACCTCGGGAGGAAGTCGAACATCTGGATCTCGG

ATCGGAACCCCGATTCGAGGCGGGAGCTTCTCTACGTCGGCCTCTACCTC

CTCGTGTGGGGGGAGGCGGCGAATCTTAGGTTTATGCCGGAGTGTGTCTG

TTACATCTTCCACAATATGGCCTCGGAGCTTAACAAGATCCTCGAGGATT

GCCTCGACGAGAGCACGGGGCAGCCGTACTCTCCTAGAATCACGGGGGAG

AATAGTTTCCTAAACGGCGTCGTTAAACCTATTTACGAGACGATCAAAGC

TGAGATTAACGAGAGCAAGAACGGGACGGAGCCGCATTGTAAGTGGAGGA

ACTATGATGATATTAATGAATACTTTTGGACGGATAGGTGTTTAGTAAA

TTGAAATGGCCGATTGATTTGGGGAGCAGTTTCTTCAAGAGTAGTAGAGG

GAGAGGCGTTGGGAAGACAGGTTTTGTGGAGAGGAGGACGTTCTTTTACC

TCTACAGGAGCTTTGATAGGCTTTGGGTGATGCTTGCTTTGTTTCTTCAA

GCTGCTATTATAGTCGCTTGGGAGGAGAAGCCGGGTGGAGGGTCGGTGAG

GAGTCAGCTCTGGAATGCGTTGAAGTCGAGGGATGTTCGGGTGAGGCTTT

TGACTGTGTTCTTGACGTGGAGTGGGATGAGATTACTGCAGGCTGTGCTG

GACGCTGCCTCGCAACGGCCGCTTATTTCTAGAGAGACCAAGCGGCTGTT

TTTCAGAATGTTGATGAAGGTTGTAGCTGCTACGGTTTGGATAATTGCTT

TTATTGTTCTCTACACGAACATCTGGAAGCAGAGGAAGCAAGACAGGCAG

TGGTCCAGAGCCGCGAATGACAAGATCTATCAGTTCCTTTACGCTGTGGT

GGCTTTCTTGGTCCCTGAGATCCTGGCTTTGGCTCTGTTTATAGTCCCGT

GGATAAGGAACTTTCTGGAAGAGACCAATTGGAAGATATTCTTTGCTTTG

ACTTGGTGGTTCCAGGGTAAAAAGCTTTGTGGGTCGAGGTTTGAGAGAGGG

GTTGGTGGACAACATCAAGTACTCGACTTTCTGGATCTTTGTCCTAGCAA
```

-continued

```
CGAAGTTCACGTTCAGCTACTTCCTTCAGGTTAAGCCAATGATTAAACCC

TCGAAGCTGCTATGGAATTTGAAGGAGGTGGATTATGAGTGGCATCAGTT

CTTTGGCAAGAGCAATAGGTTTTCTGTCTTGTTATTGTGGCTGCCAGTGG

TGTTGATATACCTGATGGATATCCAAATTTGGTACGCGATCTATTCTTCG

ATTGTTGGTGCTGTTGTTGGGCTGTTTGATCATCTGGGGGAGATCAGGGA

CATGGGACAGCTTAGGCTGAGGTTTCAGTTCTTTGCTAGCGCTATTCAGT

TCAACCTAATGCCTGAGGAACAACTCCTGAATGCTAGAGGATTTGGTAAC

AAGCTTAAGGACGCCATTCATAGGTAAGTCTATTGAAGCATGTTACTGAT

ATTCCTTTATAATTTACTGTACAGAGTTTGTCTTTACGGTACAAGTTATG

GAATTTTAGTTTTGTTAAAGCAGATTCTCTTAACTCGGCTTTTCAACATT

GTAATAACCTTGAGTTTGTGTACTTTATGCAGATTGAAGCTGAGGTATGG

ACTTGGGCGGCCATTTAAGAAACTCGAGTCTAATCAGGTTGAGGCTAACA

AGTTTGCGCTGATCTGGAATGAGATAATCTTAGCTTTCAGAGAAGAGGAT

ATAGTCTCTGATCGAGAAGTAGAGCTACTGGAGCTGCCAAAAAATTCCTG

GAATGTGACAGTTATCCGCTGGCCGTGTTTCCTGTTGTGCAACGAGCTTT

TGCTTGCACTGAGCCAGGCGAAAGAGCTGGTTGACGCACCTGATAAATGG

CTGTGGCACAAGATATGCAAGAACGAGTACAGGCGGTGTGCTGTGGTTGA

GGCATATGAAAGCATCAAACATCTGTTGCTCTCAATCATCAAAATTGACA

CCGAAGAACATAAAATTATTACAATTTTCTTTCAGATGATTGAGGTGTCT

ATTCAGGGTGAGCAGTTCACCAAGACCTTCAAAGTGGACCTATTGCCAAA

GATTTATGAGACGCTACAGAAGTTGGTTGGGCTGTTGAATGATGAGAAAG

TGGATGTTGGGCGAGTGGTGAATGGTCTGCAGTCTATTTATGAGATTGCA

ACACGACAGTTCTTCATAGAAAAGAAGACGACTGAACAGCTATCTACCGA

GGGGTTAACTCCTCATGATCCAGCCTCAAAGTTACTGTTTCAGAATGCTG

TTAGGCTTCCCGATGCAAGCAATGAAGACTTCTTCCGGCAGGTTAGGCGG

TTACACACAATTCTCACTTCTAGGGACTCTATGCACAGCGTCCCTGTGAA

TCTAGAGGCGAGACGGCGGATTGCCTTCTTCAGCAATTCGCTCTTCATGA

ACTTGCCTCATGCACCTCAGGTGGAGAAAATGTTGGCGTTCAGTGTTATG

ACTCCATACTACAGCGAGGAAGTTGTATACAGTAAAGAACAGCTCCGAAA

TGAGACTGAGGATGGGATTTCAACCTTGTATTACCTGCAGACGATTTATG

CCGACGAATGGAAAAATTTTAAGGAACGGATGCGTAGGGAAGGTATAAAG

ACAGATGTTGAGTTGTGGACAACCAAGCTGAGAGAGCTCAGGCTTTGGGC

TTCCTACGAGGTCAGACTTTGGCACGTACAGTTCGAGGAATGATGTACT

ATTACAGGGCTCTTAAGATGCTTGCTTTTCTCGACTCTGCGTCTGAAATG

GACATTCGGGAGGATGCTCAGGAGCTTGGTTCAATGAGGAGTTCGCAGGG

AAATCGATTGGATGGTGTTGACGATGTAAATGACCGATCTTCTCTAAGCA

GAGCAACTAGCTCTGTGAGCATGCTGTATAAAGGCCATGAGCATGGGACT

GCATTGATGAAATTCACATATGTCGTGGCGTGCCAAATCTATGGGTCTCA

AAAAGCGAAGAAAGAGCCTCAGGCAGAGGAAATTCTGTATCTTATGAAGC

AAAACGAAGCCCTTCGTATTGCATATGTGGATGAGGTACATGCGGGCAGG
```


-continued

```
GGAGAGACTGAGTATTACTCCGTTCTGGTGAAATACGATCACACGTTGGA

GAGGGAAGTGGAGATATTCCGTGTGAAGCTACCTGGTCCGGTGAAGCTGG

GTGAGGGAAAGCCAGAGAACCAGAATCATGCAATGATCTTTACCCGTGGT

GATGCTGTTCAGACCATAGATATGAACCAGGATAATTATTTTGAGGAGGC

TCTCAAGATGAGAAATTTGCTCCAGGAGTTTAGGCATTATCATGGGATCA

GAAAACCAACTATTCTTGGTGTCAGAGAGCACATCTTCACGGGTTCTGTC

TCGTCTCTGGCTTGGTTCATGTCTGCTCAGGAGACAAGTTTCGTCACTCT

TGGTCAGCGTGTTCTAGCCAACCCGCTGAAGGTCAGAATGCATTATGGTC

ACCCTGATGTATTTGACAGATTCTGGTTCTTGAGTCGAGGTGGCATCAGC

AAAGCTTCTAGAGTTATAAATATCAGTGAGGACATCTTCGCCGGGTTTAA

TTGCACATTGCGGGGCGGTAACGTCACCCACCACGAGTATATTCAGGTAG

GGAAATGTTCATCGTTTGGATATTCTAACTAATTTATACATCGACAACAA

TACTATAATTCCACTTTTTTGTTATAACCTTTTTGTGTGTGCATATGTAT

TCAGGTTGGGAAGGGTCGAGATGTTGGATTGAATCAAATATCAATGTTTG

AGGCTAAGGTAGCCAGTGGGAATGGAGAGCAGGTTCTTAGCCGAGATGTG

TACAGGTTGGGTCATAGGCTCGATTTCTTCAGAATGTTATCATTTTTCTA

CACAACGGTGGGGTTTTTCTTCAACACGATGATGGTCATTCTCACTGTCT

ACGCTTTCCTCTGGGGCCGGGTTTATCTTGCTCTGAGCGGTGTTGAGAAG

TCCGCTCTAGCAGACAGCACAGACACCAACGCAGCGCTTGCTGTGATATT

GAACCAGCAGTTCATCATTCAGCTTGGTCTCTTCACAGCTCTGCCAATGA

TTGTGGAATGGTCTCTCGAGGAGGGTTTCCTTCTCGCGTATGGAACTTC

ATTCGGATGCAGATTCAGCTTTCTTCTGTCTTCTACACATTCTCAATGGG

GACCAGAGCTCACTATTTTGGCCGAACCATTCTCCACGGTGGAGCAAGT

ACAGAGCCACTGGACGTGGATTTGTTGTCGAGCACAAGAGTTTCACTGAA

AACTACCGTCTATACGCGCGCAGTCACTTTGTGAAGGCCATCGAGCTTGG

GCTGATCCTCATAGTCTACGCTACGCACAGTCCCATCGCCAAAGACTCAT

TGATCTATATAGCCATGACTCTCACCAGCTGGTTCCTCGTGATTTCATGG

ATACTAGCCCCTTTTGTGTTCAACCCGTCAGGTTTCGACTGGCTTAAGAC

GGTCTACGACTTCGAAGGCTTCATGAACTGGATCTGGTATCAAGGCAGAA

TCTCAACGAAGTCCGAACAGAGCTGGGAGATATGGTGGTATGAGGAACAG

GACCACCTGAGAACCACCGGTCTACCAGGAAGAATCATGGAGATAATCTT

GGACCTTCGGTTTTTCTTCTTCCAGTACGGGATTGTATACCAGCTCAAAA

TCGCAAACGGATCAACCAGCATTCTCGTCTACTTACTCTCATGGATATAC

ATCTTCGCAGTGTTTGTGTTCTTCCTGGTAATCCAATACGCCCGTGACAA

GTACTCAGCGAGAAACCACATACGGTACAGGCTCGTTCAATTCCTCCTGA

TCGTGTTTGGTACACTGGTGATTGTTGCTCTCCTGGAGTTCACGCATTTC

AGCTTCGTGGATATCTTCACGAGTCTTCTTGCGTTCGTCCCAACCGGCTG

GGGAATCTTGCTGATCGCACAGGCTTTGAGGCCTGCGCTGCAGAAGATCG

GGCTTATCTGGAACGCGGTTATCTCCCTTGCTCGGTTATATGACATACTG

TTCGGGATAGTCATCATGGTCCCCGTAGCGTTCATGTCGTGGATGCCTGG

GTTTCAGTCGATGCAAACGAGGATCTTATTCAATGAAGCTTTTAGCAGAG
```

-continued

```
GGCTTCGTATCATGCAGATTGTCACTGGGAAGAAATCTAAAGGCGATGTC

GAAGTTGAAAAAAGAAGGTAAAGCTTTTATAACTTGTGTTCTGTTTATGT

TTGTTTGGAATCTTAAATTACAACAACACCAATGCAAAGCTTTTATAACT

TGTTTAGGTCTTAAGGTATATGGTAACTTAAAAGTCGTTGGTTTTGCGGC

GATGTGATCAGTTGGAGGTTAGTTTTCTCAAGACATGGAAGTTTTATAAG

TTATTGCTTCTTGTGTGAAGAAGAAGTCATATACATCCATGTTTTGTTTT

GTCTTCTTCTTAAAGCAGGTTTTTGGAGAGCTTTGGTTGAGGAATCCGGA

AGTTAGATAATCTTTTAGTGGGGGAGACATATATATACACATTTGTCAGT

ACTTTGTTAGAGTGTGTGGAAGTGGGGACGACTCTGATTCTGGTTCCTTA

TGTGGTTATTGTCTGAAACGTTACAGCATTTTGTGAAGTAGGCTTTTGTG

CAAGATTTGATCTCTTTCTCTCATTGTAGAGCTTTAGAGCATTTTTTAGT

ATATGTTTAATCTTTTGATTTTCTAATGTCATTTGCATTCATATTTCACA

TCTTCTTCGTTGGTCTTAAACCAGTTTTCAGATGCTTATCCATTGTCCAC

TTTTTCTATGTATCTGTTTCTTCTGTTTGTTTTCAGTATTGTCTTTTATTC

TTTAATCAGTTTTATTTGGACCACAACACCA

SEQ ID NO. 4
AAAGTAATAAAATGGTTCCAAATTTCAATACATCAATGGTTTTCTAATGC

TGACTTGCTTTTCCTCTTTTACTTAAACGATAAGGAAACGAGAGAGGTTG

AAGAAACAAAGAAACTTCCTAAGCATTTACAAATATATCTTCAAAAAATC

TAGTATTTACCAAGTAAAATCATACAAAATAAGAAAAAAAAAGAAGAATC

TATTTCCCAATTTGGTTTTCACCGGAAAAAAAAAACTGTCTTAACAAAAT

CTTAATGCACCAAATCATATAAGAACTTTATTTGACCATTGTCATTAGTT

TTTTTCCTTATGGTAATGGATCTTCAAATAATTTAAATTAAATTAAAAAA

AAAGAAAAAGAAACAAAAACGCGGAAAGGAGAGCCCAAATCGTCTCCGT

CTGTCATTGTCGCAGTCTCTAAAAGAGAAAAACAAATCGCAACGCTTCAA

TATCTCTCTCTCTCCCTATCGTTTGAATCAGTCTCCCAAGATCCACCA

CCACACATGCTACTATGAGCCTCCGCCACCGCACCGTCCCCTCACAACCC

GGACGGCCCCCGGCGGCGGGCGCAATCGACGAGGAGCCCTACAACATCAT

CCCCGTCAACAACCTCCTCGCCGACCACCCCTCCCTCCGCTACCCCGAGG

TCCGCGCCGCCGCCGCCGCCCTCAAAACCGTCGGCGACCTCCGCCGCCCC

ACCTACGTCCAATGGCGCCCCCACTACGACCTCCTCGACTGGCTCGCCCT

CTTCTTCGGCTTCCAGAAGGACAACGTCCGCAACCAGCGCGAGCACCTCG

TCCTCCACCTCGCCAACGCCCAGATGCGCCTCTCCCCGCCGCCGGACAAC

ATCGATTCCCTCGATCCCGCCGTCGTCCGCCGCTTCCGCCGCAAGCTCCT

CGGTAACTACTCCAGCTGGTGCTCCTACCTCGGGAGGAAGTCCAACATCT

GGATCTCGGATCGGACCCCCGATTCGCGGCGGGAGCTTCTCTACGTCGGC

CTCTACCTCCTCGTGTGGGGCGAGGCGGCGAATCTTAGGTTTATGCCTGA

GTGTATCTGTTACATCTTCCACAATATGGCCTCGGAGCTTAACAAGATCT

TAGAGGATTGCCTCGACGAGAGCACGGGGCAGCCGTATTCTCCTAAGATC

ACGGGGGAGAATAGTTTCCTAAACGGCGTCGTTAAGTCAGAACAAAAGGA

AGATTCCATCTAATGGATTATAATCCCACATGCCCATTTTTAAAACTAGA
```

-continued

CAAAATAACTTATAATAGTCCCATAAGAGCATTAAGACAAACTGAACCAA

AAAGAATCTTAAATGCTGGTGAATCTAGTCTCGAATGCTGCTGAACACTC

CTGATATTAGAATTTGGCAGAAAATATTCATACTAATAACAGTAAATACA

TTTCAAAACAAGAAAATAGTAGTAGTAAATAAAAACAATTAATATGTTAT

TATTGTTTCTCTTAGCTGTTACCATTACATTAACAATTTACATTCAATCC

TTTTAATGAAAAATATTATAAAATATTAAAAGAAGTTATTAGAAAAGGAG

AGGGATATGGGGGGGGGAGAGCATGGAGGGGTCCCATGTGTGTTTCGAA

AAGCAGCAAACATGACTTTGTAAAGTCTTGTTTTAGCTAGAGTTCCAAAA

AAAAAAGAGTTCAAAAAAAAGAAAAAAAAAAGTCTTGTTTTAGCGTCCA

AAGCGGTCTCACTCGCCGTTCAGCTGTTAAATTTTCTTGAAATAAATCGC

TCCACTTGTTTTTTATTTTTGTTTCTTTCAACCCACTTGTATTAATAACA

ATAATGATATTGCTAATCTTGAACAAATCGTGGATTGTCTTTTCTTCCAG

TGATATCATCCTTAGTCAAAACATCTCAAATTAAATAAATATATAGTTGT

GAATTAAAAAAAAAGGTATAGAGTTTATAAAATTAGCATTTGCGAATGTT

TTTAAAAGTTTGGCGTTTGTATAGATCACTGTCAGTGTCATGAATCATTC

GGTGACAGCAAATTTGTATATGCCAAAAAAGAGAGTTGATACTTGCCATT

CTCGATATTTTGAATTTTTTTTCGTCGACATACAAACTCAACATTTTCGA

AATCTTAGATTAAAAACAAAATGGACAAAACGATACTTATTAATGAATTA

TGTACTAGCGTCTAAACATTAGTAACATAGATATAATTATAAGAACAAGA

AACATATATGCACAAAGCCTCAAACCAAATTTAAATAGTGTTACGAAACA

AGGGATGTACTTGTTATGAAAAATTAATGTATAACCATTCTTAGCATTTT

TTACCTAACCCTTAAACTTTATAAAGAAAAATATGTAACATTTCGGTGTG

TGGTATATAAAAGTATTTTGAAAATCGATTTGATTATTTCTATTATTAAA

ATGTACTTACTTTTTTTATCACACATTTATTTACAATTTCAGAGTTAAAC

ATGATTAAGACAAAGTAGTGAAAATATAGATGATCTACCAGAAAATCATT

TGCTTTCTGAGTGAGATCAAAATAAAGGCAAAAATAATGTGATGATTGTA

TATTAAACAATTATTTTGAATTTGAAAAGAATAACTCATCGAATGAAGCC

TATGAACCGAGTAAGCGGTGAAGCGGTTGGACCGTCACAAAAATTATGAC

CAACAAGAAAATAAAATTGATATTAGTGAATGATATATTTTGGAAAGTAA

TAAATTGGTTCCAGATTTCAATACATCAATGTTTTTCTAATGCTGACTTG

CTTTTCCTCTTTTTCTTACATGATAAGGAAACGAGAGAGGTCGAAGAAAC

AAAGAAACTTCCTAAGCATTTAGCAACGCATCTTCAAAAAATCTAGTATT

TACCAAGTAAAATCATACAAAATAAGGAAAAAAAGAAGAATATATTTCCC

AATTTGGTTTTCACCGGAAAAAAAAAACTGTCTTAACAAAATCTTAATGC

ACCAAATCATATAAGAACTTTATTTGACCATTGTCATTAGTTTTTTCCTT

ATGGTAATGGATCTTCAAACAATTTAAATTAAATTAAAAAAAAAAAGAAA

AGAGAAACAAAAACGCGGAAAGGAGAGCCCAAATCGTCTCCGTCTGTCAT

TGTCGCAGTCTCTAAAAGAGAAAAACAAATCGCAACGCTTCAATATCTCT

CTCTCTCTCTCTCCCTATCGTTTGAATCAGTCTCTCAAGATCCACCACCA

CACATGCTACTATGAGCCTCCGCCACCGCACCGTCCCCTCTCAACCCGGA

-continued

CGGCCCCCGGCGGCGGGCGCAATCGAGGACGAGCCCTACAACATCATCCC

CGTCAACAACCTCCTCGCCGACCACCCCTCCCTCCGCTACCCCGAGGTCC

GCGCCGCCGCCGCCGCCCTCAAAACCGTCGGCGACCTCCGCCGCCCCACC

TACGTCCAATGGCGCCCCCACTACGACCTCCTCGACTGGCTCGCCCTCTT

CTTCGGCTTCCAGAAGGACAACGTCCGCAACCAGCGCGAGCACCTCGTCC

TCCACCTCGCCAACGCCCAGATGCGCCTCTCCCCGCCGCCGGACAACATC

GATTCCCTCGATCCCGCCGTCGTCCGCCGCTTCCGCCGCAAGCTCCTCGG

TAACTACTCCAGCTGGTGCTCCTACCTCGGGAGGAAGTCCAACATCTGGA

TCTCGGATCGGACCCCCGATTCGCGGCGGGAGCTTCTCTACGTCGGCCTC

TACCTCCTCGTGTGGGGCGAGGCGGCGAATCTTAGGTTTATGCCTGAGTG

TATCTGTTACATCTTCCACAATATGGCCTCGGAGCTTAACAAGATCTTAG

AGGATTGCCTCGACGAGAGCACGGGGCAGCCGTATTCTCCTAAGATCACG

GGGGAGAATAGTTTCCTAAACGGCGTCGTTAAGCCTATCTACGACACGAT

CAGAGCTGAGATTAATGAGAGCAAGAACGGGACGGAGCCGCATTGTAAGT

GGAGGAACTACGATGATATTAATGAGTACTTCTGGACGGATAGGTGTTTT

AGTAAATTGAAATGGCCGATTGATTTGGGGAGCAGTTTCTTCAAGAACAG

CAGAGGTAGCGGAGTTGGGAAGACAGGTTTTGTGGAGAGGAGGACGTTTT

TCTACCTCTACAGGAGCTTTGATAGGCTTTGGGTGATGCTTGCTTTGTTT

CTTCAAGCTGCTATTATAGTTGCTTGGGAGGAGAAGCCGGGTGGAGGGTC

GGTGACGAGTCAGCTCTGGAATGCGTTGAAGTCGACGGATGTTCAGGTGA

GGCTTTTGACTGTTTTCTTGACGTGGAGTGGGATGAGGTTGTTGCAGGCT

GTGCTGGACGCTGGCTCGCAACGGTCGCTTATTTCTAGAGAGACCAAACG

GCTGTTTTTCAGAATGTTGATGAAGGTTGTGGCTGCTACGGTTTGGATAA

TAGCGTTTATTGTTCTCTACACGAACATCTGGAAGCAGAGGAAGCAAGAT

AGGCAGTGGTCCAGAGCCGCGAATGATAAGATCTATCAGTTCCTTTACGC

TGTGGTGGCTTTCTTGGTCCCTGAGATCCTGGCTTTGGCTCTGTTTATAG

TCCCGTGGATAAGGAACTTTCTGGAAGAGACCAATTGGAAGATATTCTTT

GCTTTGACTTGGTGGTTCCAGGGGAAAAGCTTTGTGGGTCGAGGTTTGAG

AGAGGGGTTGGTGGACAACATCAAGTACTCGACTTTCTGGATCTTTGTCC

TCGCAACGAAGTTCACGTTCAGCTACTTCCTTCAGGTTAAGCCAATGATT

AAACCCTCGAAGCTGCTATGGAATTTGAAGGAGGTGGATTATGAGTGGCA

TCAGTTCTTTGGCGAGAGCAATAGGTTTTCTGTCTTGTTATTGTGGCTGC

CAGTGGTGTTGATATACCTGATGGATATCCAAATTTGGTACGCGATCTAT

TCTTCGATTGTCGGTGCTGTTGTTGGGCTGTTTGATCATCTGGGGGAGAT

CAGGGACATGGGACAGCTTAGGCTGAGGTTCCAGTTCTTTGCTAGCGCTA

TTCAGTTCAACCTAATGCCTGAGGAACAACTCCTGAATGCTAGAGGATTT

GGTAACAAGCTTAAGGACGCCATTCATAGGTAAGTCTATTGAAGCATGTT

ACTGATATTCCTCCTATATAATTTACTATACAGAGTTTGTCTTTACAGTA

CAAGCTATAGGATTTTAGTTTTGTTAAAGCAGATTCTCCGCAATGAACTA

GACTTTTTCACATTGTAATAACATTGAGTTTGTGTACTTTATGCAGATTG

AAGCTGAGGTATGGATTGGGGCGGCCGTTTAAGAAACTCGAGTCCAATCA

-continued

GGTTGAGGCTAACAAGTTTGCGCTGATCTGGAATGAGATAATCTTAGCTT

TCAGAGAGGAGGATATAGTCTCTGATCGAGAAGTAGAGCTGCTGGAGCTG

CCAAAGAATTCCTGGAATGTAACAGTTATCCGCTGGCCGTGTTCCTGTT

GTGCAATGAGCTTTTGCTTGCACTGAGCCAGGCGAAAGAGCTGGTTGACG

CACCTGATAAATGGCTGTGGCACAAGATATGCAAGAATGAGTACAGGCGG

TGTGCTGTGGTTGAGGCATATGAAAGCATCAAACATCTGTTGCTTTCAAT

CATCAAAATTGACACTGAAGAACATAAAATTGTTACAATTTTCTTTCAGA

TGATTGAGGTCTCTATTCAGGGTGAGCAGTTCACCAAGACCTTCAAAGTG

GACCTTTTGCCAAAGATTTATGAGACACTACAGAAGTTGGTTGGTCTGTT

GAATGATGAGAAAGTGGATGTTGGGCGAGTGGTGAATGGTCTGCAATCTA

TTTATGAGATTGCAACACGACAGTTCTTCATAGAAAAGAAGACGACTGAA

CAGCTATCTACTGAGGGGTTAACTCCTCATGATCCAGCCTCAAAGTTACT

GTTTCAGAATGCTGTTAGGCTTCCCGATGCAAGCAATGAAGACTTCTTCC

GGCAGGTTAGGCGGTTACACACAATTCTCACTTCTAGGGACTCTATGCAC

AGCGTCCCTGTGAATCTAGAGGCGAGACGGCGGATTGCCTTCTTCAGCAA

TTCGCTCTTCATGAACTTGCCTCATGCACCTCAGGTGGAGAAAATGTTGG

CGTTCAGTGTTATGACTCCATACTACAGCGAGGAAGTTGTATACAGCAAA

GAACAGCTCCGAAATGAGACTGAGGATGGAATTTCAACCTTGTATTACCT

GCAGACGATTTATGCCGACGAATGGAAAAATTTTAAGGAACGGATGCGTA

GGGAAGGTATAAAGACAGATGTTGAGTTGTGGACAACCAAGCTGAGAGAG

CTCAGGCTTTGGGCTTCCTACAGAGGTCAGACTTTGGCACGTACAGTTCG

AGGAATGATGTACTATTACAGGGCTCTTAAGATGCTTGCTTTTCTTGACT

CTGCGTCTGAAATGGACATTCGGGAGGATGCTCAGGAGCTTGGTTCAATG

AGGAGTTCGCAGGGAAATCGATTGGATGGGGTTGACGATGTAAATGACGG

ATCTTCTCTAAGCAGAGCAACTAGCTCTGTGAGCATGCTGTATAAAGGCC

ATGAGCATGGGACTGCATTGATGAAATTCACATATGTCGTGGCGTGCCAG

ATCTATGGGTCTCAAAAAGCGAAGAAGGAGCCTCAGGCAGAGGAAATTCT

GTATCTTATGAAGCAAAACGAAGCCCTCCGTATTGCATATGTGGATGAGG

TACATGCGGGCAGGGGAGAGACTGAGTATTACTCCGTTCGGTGAAATAC

GATCATACGTTGGAGAGGGAAGTGGAGATATTCCGTGTGAAGCTACCTGG

TCCGGTGAAGCTGGGTGAGGGAAAGCCAGAGAACCAGAATCATGCAATGA

TCTTTACCCGTGGTGATGCTGTTCAGACCATAGATATGAACCAGGATAAT

TATTTTGAGGAGGCTCTCAAGATGAGAAATTTGCTCCAGGAGTTTAGGCA

TTATCATGGGATCAGAAAACCAACTATTCTTGGTGTCCGGGAGCACATCT

TCACGGGATCTGTCTCGTCTCTGGCATGGTTCATGTCTGCTCAGGAGACT

AGTTTCGTCACTCTTGGTCAGCGTGTTCTCGCCAATCCGCTGAAGGTCAG

AATGCATTATGGTCATCCTGATGTTTTTGACAGATTCTGGTTCTTGAGTC

GAGGTGGCATCAGCAAAGCTTCTAGAGTTATAAATATCAGTGAGGACATC

TTCGCCGGGTTTAATTGCACATTGCGGGGCGGTAACGTCACCCACCACGA

GTATATTCAGGTAGGGAAATGTTCATCATTTGGATATTCTAACTAATTTA

-continued

TACATCGACAACAATACTATAATTCCACTTTTTTTGTTATAACCTTCGTG

TGTGTGCATATGTATTCAGGTTGGGAAGGGTCGAGATGTTGGATTGAATC

AAATATCAATGTTTGAGGCTAAGGTAGCCAGTGGGAATGGAGAGCAGGTT

CTTAGCCGAGATGTGTACAGGCTGGGTCATAGGCTCGATTTCTTCAGAAT

GTTATCATTTTTCTACACAACGGTGGGGTTTTTCTTCAACACGATGATGG

TCATTCTCACTGTCTACGCTTTCCTCTGGGGTCGGGTTTATCTTGCTCTG

AGCGGTGTTGAGAAGTCCGCTCTAGCAGACAGCACAGACACCAACGCAGC

GCTTGCTGTGATATTGAACCAGCAATTCATCATTCAGCTTGGTCTCTTCA

CAGCTCTGCCAATGATTGTGGAATGGTCTCTCGAGGAGGGTTTCCTTCTA

GCGATATGGAATTTCATTCGGATGCAGATTCAGCTTTCATCTGTCTTCTA

CACATTCTCAATGGGGACCAGAGCTCACTATTTTGGCCGAACCATTCTCC

ATGGTGGAGCAAAGTACAGAGCCACTGGGCGTGGATTTGTTGTCGAGCAC

AAGAGCTTCACTGAGAATTACCGTCTATACGCACGCAGTCACTTTGTGAA

GGCCATCGAGCTTGGGCTGATCCTCATAGTCTACGCTACGCACAGTCCCA

TCGCCAAAGACTCATTGATCTATATAGCTATGACTCTCACCAGCTGGTTC

CTCGTGATTTCATGGATACTGGCCCCTTTTGTGTTCAACCCGTCAGGATT

CGACTGGCTTAAGACGGTCTATGACTTCGAAGGCTTCATGAACTGGATCT

GGTATCAAGGCAGAATCTCAACGAAGTCCGAACAGAGCTGGGAGATATGG

TGGTATGAGGAACAGGACCACCTGAGAACCACCGGTATACCAGGAAGAAT

CGTGGAGATAATCTTGGACCTTCGGTTTTTCTTCTTCCAGTACGGGATTG

TATACCAGCTCAAAATCGCAAACGGATCAACCAGCATTCTCGTCTACTTA

CTCTCATGGATATACATCTTCGCAGTGTTTGTGTTCTTCCTAGTAATCCA

ATACGCCCGTGACAAGTACTCAGCGAGAAACCACATACGGTACAGGCTCG

TCCAGTTCCTCCTGATCGTGTTTGGTACACTGGTGATTGTTGCTCTCCTC

GAGTTCACGCATTTCAGCTTCGTGGATATCTTCACGAGTCTTCTTGCGTT

CGTCCCAACCGGCTGGGGAATCTTGCTGATCGCACAGGCTTTGAGGCCTG

CGCTGCAGAAGATCGGGCTTATCTGGAACGCGGTTGTCTCCCTTGCTCGG

TTGTATGACATACTGTTCGGGGATAGTCATCATGGTTCCCGTAGCGTTCAT

GTCGTGGATGCCTGGGTTTCAATCGATGCAAACGAGGATCTTATTCAATG

AAGCTTTTAGCAGAGGGCTTCGTATCATGCAGATTGTCACTGGGAAGAAA

TCAAAAGGCGATGTCGAAGTTGAAAAAAGAAGGTAAAGCTTCTTATTTAC

CCAAACATCTTTTATGTTCTGTTTGTTTGGAATCTTAAATTACAACAACA

CTAATGCAAAGCTTTTATAACTTGTGTAGGTCTTGAGGTATATGGTAATT

TAAAAGTTGCTGGTTTGCGGCGATGAGGTTAGTTTTGTATTCTTATAAGT

TATGCTTCTTGTCTGAATAAGAACTCAGACACCCGTGTTTTGTCTTCTTC

TTATTTTAAACCAGGTTTTTGGAGAGCTTTGGTTGAGGAAGCTATTTGAT

TAGTTCATCGGTTAGTGGGAGAAACATATATATACATTTGTCAGTACTTT

GTTAGAGTGTGTGAAATGGGGACGACTCTGATTCTGATTCCTTATGTGG

TTATTGTCTGAAACGTTACAGCATTTTGTGAAGTAGGCTTTTGTGCAAGA

TTTGATATCTTTCTCTCATTGTAGAGCTTTAGAGCATTTTTTAGTATATG

TTTAATCTTTGATTTTTCTAATGTCATTTGCATTCATATTTCAC

-continued

SEQ ID NO. 5
GTTTCTTTTTTTTTTTGGTCGAAATTATATTATTGTTTCTCTGAGCTGTT

ACCATTACATTAACAATTTACATTCTATCCTTTTGATGAAAAATATTATA

AAATGTTAAAAGAAGTTATTAGAAAAGGAGAGGAAAACAGGGGGAGAGCA

TGGAGGGGTCCCATGTGTGTTTCGGAAAGCAGCAAACATGACTTTGTAAA

GTCTTGTTTTAGCGTCCAAAGCGGTCTCACTCGCCGTTCAGCGAGCTTTA

GCTGTTAAATTTTCTTGAAATAAATCGCTCCACTTGTTAAAAAAAAAAAT

GATAACTGTGTCCATTTCGACTAATATCTATTTTGTGTCATTTTTGCATA

TAATATTTTTAATATTTTTGAAAATAAATTTAATAAATAGTTTTATAAA

CAAAAAAATTGAAAAATAGTAACTATTGATAAAATACCTATATGAACTT

AGTAGTATTTTTTTCAGTTCTAAAAATGTTTAAATCATAATTTTCAGAT

TATGTTATAAATAAAGCAGAAATGACATTCTACGAAGTAGAAAACGAAAT

CCATTTTTTTTCATTGAATCTACAATGTTTAGAATACGAAATCTTCGTAA

ATAAGAGTATTCTAAAAATATTTAGAATACACATTCCGCGCTTAACCTAC

CGATCTAAAATCTTTAGAAATCAAAATCTACAGATTAATATAAATCTAAA

ACACGTTGAAACCGACTTCTACAGATTTACTGTAAATCTAAAACATGTAG

AAATCAAAATTCTACACATTACTATAATTCTAAAAACCTATAGAAACCGA

TTTCTACATATTATCTGTATTCTACGGATAAGAAATCAGTTCTTAAAAAT

ATGGAAACAAAATATTTGAGAATATTCACTTTCATATTTTGAAAAAAATC

GATTTAAAAAAAACAAAAAAAACAAAAAACCTTCTTTTCACGCCGTCTTC

TATATTCCATTGATTGTTCACAAAATTTTCACATTATTTCCACCATATCA

GTGTGAAATTGAGTGAGTTAGGGTTTATGAACTTGAGACTTTGATTTTCT

CCCTTTTTGTTCGTGAAGGAGATGAGAAATTATGAGTTTCATCTCAAAGA

AATCGAGTTTAAAGAGTTGAAATCGTGTTTGGTCGGTTCAAATCAAGTGG

GAATTAAAACCGGATATAACCGAAGAAAACCAGGAAATCGATTTGGAATAC

TTACCTAGGCACAAGATCGATCGGTCTATAATTAGAGATCGGTTGATCTG

TATGAAATCGACTTTTGCCGATCGAGTGAAATGGACCAGGTCGATCAGCC

GCGTTTTTTTGTTCTGCATAATGATCAGAATCGGTCAATCCGTCCGACCT

TGTAATTTCGGATCGATCGATCCCGCTTGATCGAACCTATTATTTATTAT

ATTTAAGAATTACAATTTTAAGGATTTTATTGCCATTTTGAAAATAATTA

GTCTAATTGAACATAAAATATATAAGATTAGTCTAAAATGACATAGTTAT

CATTTTTTGTTCTAAAAAAACAATTTCCCTTTTTTATTTTTGTTTCTTTC

AACACACTTGTATTAATAACAATAATGATATTGCTAATCTTGAACAAATC

GTGGATTGTCTTTTCTTCCGGTGATATCATCCTTAGTCAAAACATCTCAA

ATTAAATAAGTATAGAGTTGTGAATGTTTTTAAAAGTTTGGCGTTTGTAT

AGATCACTGTCAGTGTCATGAATCATTAGGTGACTGCAAATTTTTATATG

ACAAAAAAGAGAGTTGATACTTGCCATTCTCGAGATTTTGAAGTTTTTTT

CGTCGTCAACATACAAACTCAACATTTTCGAAATCTTGGATTAAAAATAA

AAATATGGACAAAACGATACTTATTAATTAATTATGTACTAGCGTCTTAA

CATTATTAATATAGATATAATTATAAGAACAAGAAACATAAACATATATG

CACAAAGCCTCAAAGCAAATTTAAATAATGTTACAAAACAAGGGATGTAC

-continued

TTGTTATGAAAAATTAATATATAACCATTCTTAACATATTTTTACGTAAA

CCTTAAACTTTATAAAGAAAAATATGTAACATTCCGGTGCGTGGTATATA

GAAATATTTTTAAAAATTGATTTGACTATTTCCATTAGCAAAATGCATTT

ATTTTTTCGATCATACATTTATTTAAAATTTCAGGGTTAAACGTGATTAA

AATGGAGTAATAAGAATATGGATGATCTACCAGAAAATCATTTACGTTTT

AAGTGAGACCAAAATACGGATAAAAATCATGTGATGATTGTATGGTTATT

AAACAATTATTTTGAATTTGAAAATAATTAACTCATCAAATTAAACCTAA

GGACCGAGTAAGCGGACGCAGATAGCCGTAAGCGGTTGGGCCGTCACAAA

ATTTATGACCAACAAGAAAATGAAACTGATTTTAGTGGATGATATATTTT

AGAAAGTAATAAAATGGTTCCAGATTTCAATACTTCAATGGTTTTTTTAT

GCTGACTTTCTTTTCCTCTTTTACTTACATGATAAGGAAACGAGAGAGGT

TGAAGAAACAAAGAAAATTCCTAAGGATTTAGAAATGTATCTTCAAAAAA

TCTAAGTATTTACCAAGTAAAATCATACAAAATAAGGAAAAAAAAAGAAT

TTATTTCCCAATTTGGTTTTTACCGGAAAAAAAATTGTTTTAATAAAATC

TTATGCACCAAATCATATAAGAACGAACCATAACAAACTTTATTTGACCA

TTGTCATTAGTTTATTTTATTTATGGTAATGGATCTTCAAATAATTTGAA

TTAAATTAAAAAAAAGAATAAAAAAAGAGAAACAAAAACGCGGAAAGGAG

AGCCCAAATCGTCTCCGTCTGTCATTGTCGCAGTCTCTCACAGCTAAATA

AAAGAGAAAACAAATCGCAACGCTTCAATATCTCTCTCCCAATCGTTTG

AATTAGTCTTCCTCATCACAATACCCCTAAGATCCACCTCACATGCTACT

ATGAGCCTCCGCCACCGCACCACCGTCCCCTCTCAACCCGGACGGCCCCC

GGCGGCGGGCGCAATCGACGAGGAGCCCTACAACATCATCCCCGTCAACA

ACCTCCTCGCCGACCACCCCTCCCTCCGCTACCCCGAGGTCCGCGCCGCC

GCCGCCGCCCTCAAAACCGTCGGAGACCTCCGCCGCCCCACCTACGTCCA

ATGGCGCCCCCACTACGACCTCCTCGACTGGCTCGCCCTCTTCTTCGGCT

TCCAGAAGGACAACGTCCGCAACCAGCGCGAGCACCTCGTCCTACACCTC

GCCAACGCCCAGATGCGCCTCACGCCGCCGCCGGATAACATCGATTCCCT

CGATCCCGCCGTCGTCCGCCGTTTCCGCCGCAAGCTCCTCGGTAACTACT

CGAGCTGGTGCTCGTACCTCGGGAGGAAGTCGAACATCTGGATCTCGGAT

CGGAACCCCGATTCGAGGCGGGAGCTTCTCTACGTCGGCCTCTACCTCCT

CGTGTGGGGGGAGGCGGCGAATCTTAGGTTTATGCCGGAGTGTATCTGTT

ACATCTTCCACAATATGGCCTCGGAGCTTAACAAGATCCTCGAGGATTGC

CTCGACGAGAGCACGGGGCAGCCGTATTCTCCTAGAATCACGGGGGAGAA

TAGTTTCCTAAACGGCGTCGTTAAACCTATTTACGAGACGATCAAAGCTG

AGATTAACGAGAGCAAGAACGGGACGGAGCCGCATTGTAAGTGGAGGAAC

TATGATGATATTAACGAGTACTTTTGGACGGATAGGTGTTTCAGTAAATT

GAAATGGCCGATTGATTTGGGGAGCAGTTTCTTCAAGAGTAGTAGAGGGA

GCGGCGTTGGGAAGACAGGTTTTGTGGAGCGGAGGACGTTTTTTTACCTC

TACAGGAGCTTTGATAGGCTTTGGGTGATGCTTGCTTTGTTTCTTCAAGC

TGCTATTATAGTTGCTTGGGAGGAGAAGCCGGGTGGAGGGTCGGTGAGGA

-continued

```
GTCAGCTCTGGAATGCGTTGAAGTCGACGGATGTTCAGGTGAGGCTTTTG

ACTGTGTTTTTGACGTGGAGTGGGATGAGATTACTGCAGGCTGTGCTGGA

CGCTGGCTCGCAACGGCCGCTTATTTCTAGAGAGACCAAACGGCTGTTTT

TCAGAATGCTGATGAAGGTTGTAGCTGCTACGGTTTGGATCATTGCTTTT

ATTGTTCTCTACACGAACATCTGGAAGCAGAGGAAGCAAGACAGGCAGTG

GTCCAGAGCCGCGAATGACAAGATCTACCAGTTCCTTTACGCTGTGGTGG

CTTTCTTGGTCCCTGAGATCCTGGCTTTGGCTCTGTTTATAGTCCCGTGG

ATAAGGAACTTTCTGGAAGAGACCAATTGGAAGATATTCTTTGCTTTGAC

TTGGTGGTTCCAGGGTAAAAGCTTTGTGGGTCGAGGTTTGAGAGAGGGGT

TGGTGGACAACATCAAGTACTCGACTTTCTGGATCTTTGTCCTAGCAACG

AAGTTCACGTTCAGCTACTTCCTGCAGGTTAAGCCAATGATTAAACCCTC

GAAGCTGCTATGGAATTTGAAGGAGGTGGATTATGAGTGGCATCAGTTCT

TTGGCAAGAGCAATAGGTTTTCTGTCTTGTTATTGTGGCTGCCAGTGGTG

TTGATATACCTGATGGATATCCAAATTTGGTACGCGATCTATTCTTCGAT

TGTTGGTGCTGTTGTTGGGCTGTTTGATCATCTGGGGGAGATCAGGGACA

TGGGACAGCTTAGGCTGAGGTTTCAGTTCTTTGCTAGCGCTATTCAGTTC

AACCTAATGCCTGAGGAACAACTCCTGAATGCTAGAGGATTTGGTAACAA

GCTTAAGGACGCCATTCATAGGTAAGTCTATTGAAGCATGTTACTGATAT

TTCTATATAATTTATTATACAGAGTTTGTCTTTACAGTACAAGCTATAGG

ATTTTAGTTTTGTTAAAGAAGATTTCTCCGCAATGAACTCGACTTTTCAC

ATTGTAATAACATTGAGTTTGTGTACTTTATGCAGATTGAAGCTGAGGTA

TGGATTGGGGCGGCCGTTTAAGAAACTCGAGTCCAATCAGGTTGAGGCTA

ACAAGTTTGCGCTGATCTGGAATGAGATAATCTTAGCTTTCAGAGAGGAG

GATATAGTCTCTGATCGAGAAGTAGAGCTGCTGGAGCTGCCAAAGAATTC

CTGGAATGTGACAGTTATCCGCTGGCCGTGTGTTCCTGTTGTGCAACGAGC

TTTTGCTTGCACTGAGCCAGGCGAAAGAGCTGGTTGACGCACCTGATAAA

TGGCTGTGGCACAAGATATGCAAGAATGAGTACAGGCGGTGTGCTGTGGT

TGAGGCATATGAAAGCATCAAACATCTGTTGCTCTCAATCATCAAAATTG

ACACCGAAGAACATAAAATTGTTACAATTTTCTTTCAGATGATTGAGGTG

TCTATTCAGGGTGAGCAGTTCACCAAGACCTTCAAAGTGGACCTATTGCC

AAAGATTTATGAGACGCTACAGAAGTTGGTTGGGCTGTTGAATGATGAGA

AAGTGGATGTTGGGCGAGTGGTGAATGGTCTGCAGTCTATTTATGAGATT

GCAACACGACAGTTCTTCATAGAAAAGAAGACGACTGAACAGCTATCTAC

CGAGGGGTTAACTCCTCATGATCCAGCCTCAAAGTTACTGTTTCAGAATG

CTGTTAGGCTTCCCGATGCAAGCAATGAAGACTTCTTCCGGCAGGTTAGG

CGGTTACACACAATTCTCACTTCTAGGGACTCTATGCACAGCGTCCCTGT

GAATCTAGAGGCGAGACGGCGGATTGCCTTCTTCAGCAATTCGCTCTTCA

TGAACTTGCCTCATGCACCTCAGGTGGAGAAAATGTTGGCGTTCAGTGTT

ATGACTCCATACTACAGCGAGGAAGTTGTATACAGTAAAGAACAGCTCCG

AAATGAGACTGAGGATGGGATTTCAACCTTGTATTACCTGCAGACGATTT

ATGCCGACGAATGGAAAAATTTTAAGGAACGGATGCGTAGGGAAGGTATA
```

-continued

```
AAGACAGATGTTGAGTTGTGGACAACCAAGCTGAGAGAGCTCAGGCTTTG

GGCTTCCTACAGAGGTCAGACTTTGGCACGTACAGTTCGAGGAATGATGT

ACTATTACAGGGCTCTTAAGATGCTTGCTTTTCTCGACTCTGCGTCTGAA

ATGGACATTCGGGAGGATGCTCAGGAGCTTGGTTCAATGAGGAGTTCGCA

GGGAAATCGATTGGATGGTGTTGACGATGTAAATGACCGATCTTCTCTAA

GCAGAGCAACTAGCTCTGTGAGCATGCTGTATAAAGGCCATGAGTATGGG

ACTGCATTGATGAAATTCACATATGTCGTGGCGTGCCAAATCTATGGGTC

TCAAAAAGCGAAGAAAGAGCCTCAGGCAGAGGAAATTCTGTATCTTATGA

AGCAAAACGAAGCCCTTCGTATTGCATATGTGGATGAGGTACATGCGGGC

AGGGGAGAGACTGAGTATTACTCCGTTCTGGTGAAATACGATCACACGTT

GGAGAGGGAAGTGGAGATATTCCGTGTGAAGCTACCTGGTCCGGTGAAGC

TGGGTGAGGGAAAGCCAGAGAACCAGAATCATGCAATGATCTTTACCCGT

GGTGATGCTGTTCAGACCATAGATATGAACCAGGATAATTATTTTGAGGA

GGCTCTCAAGATGAGAAATTTGCTCCAGGAGTTTAGGCATTATCATGGGA

TCAGAAAACCAACTATTCTTGGTGTCAGAGAGCACATCTTCACGGGTTCT

GTCTCGTCTCTGGCTTGGTTCATGTCTGCTCAGGAGACAAGTTTCGTCAC

TCTTGGTCAGCGTGTTCTAGCCAACCCGCTGAAGGTCAGAATGCATTATG

GTCACCCTGATGTATTTGACAGATTCTGGTTCTTGAGTCGAGGTGGCATC

AGCAAAGCTTCTAGAGTTATAAATATCAGTGAGGACATCTTCGCCGGGTT

TAATTGCACATTGCGGGGCGGTAACGTCACCCACCACGAGTATATTCAGG

TAGGGAAATGTTCATCATTTGGATATTCTAACTAATTTATACATCGACAA

CAATACTATAATTCCACTTTTTTGTTATAACCTTTTTGTGTGTGCATATG

TATTCAGGTTGGGAAGGGTCGAGATGTTGGATTGAATCAAATATCAATGT

TTGAGGCTAAGGTAGCCAGTGGGAATGGAGAGCAGGTTCTTAGCCGAGAT

GTGTACAGGTTGGGTCATAGGCTCGATTTCTTCAGAATGTTATCATTTTT

CTACACAACGGTGGGGTTTTTCTTCAACACGATGATGGTCATTCTCACTG

TCTACGCTTTCCTCTGGGGCCGGGTTTATCTTGCTCTGAGCGGTGTTGAG

AAGTCCGCTCTAGCAGACAGCACAGACACCAACGCAGCGCTTGCTGTGAT

ATTGAACCAGCAGTTCATCATTCAGCTTGGTCTCTTCACAGCTCTGCCAA

TGATTGTGGAATGGTCTCTCGAGGAGGGTTTCCTTCTCGCGATATGGAAC

TTCATTCGGATGCAGATTCAGCTTTCTTCTGTCTTCTACACATTCTCAAT

GGGGACCAGAGCTCACTATTTTGGCCGAACCATTCTCCACGGTGGAGCAA

AGTACAGAGCCACTGGACGTGGATTTGTTGTCGAGCACAAGAGTTTCACT

GAAAACTACCGTCTATACGCGCGCAGTCACTTTGTGAAGGCCATCGAGCT

TGGGCTGATCCTCATAGTCTACGCTACGCACAGTCCCATCGCCAAAGACT

CATTGATCTATATAGCCATGACTCTCACCAGCTGGTTCCTCGTGATTTCA

TGGATACTAGCCCCTTTTGTGTTCAACCCGTCAGGTTTCGACTGGCTTAA

GACGGTCTACGACTTCGAAGGCTTCATGAACTGGATCTGGTATCAAGGCA

GAATCTCAACGAAGTCCGAACAGAGCTGGGAGATATGGTGGTATGAGGAA

CAGGACCACCTGAGAACCACCGGTCTACCAGGAAGAATCATGGAGATAAT
```

31

32

-continued

-continued

CTTGGACCTTCGGTTTTTCTTCTTCCAGTACGGGATTGTATACCAGCTCA

AAATCGCAAACGGATCAACCAGCGTTCTCGTCTACTTACTCTCATGGATA

TACATCTTCGCAGTGTTTGTGTTCTTCCTGGTAATCCAATACGCCCGTGA

CAAGTACTCAGCGAGAAACCACATACGGTACAGGCTCGTTCAGTTCCTCC

TGATCGTGTTTGGTACACTGGTGATTGTTGCTCTCCTGGAGTTCACGCAT

TTCAGCTTCGTGGATATCTTCACGAGTCTTCTTGCGTTCGTCCCAACCGG

CTGGGGAATCTTGCTGATCGCACAGGCTTTGAGGCCTGCGCTGCAGAAGA

TCGGGCTTATCTGGAACGCGGTTATCTCCCTTGCTCGGTTATATGACATA

CTGTTCGGGATAGTCATCATGGTCCCCGTAGCGTTCATGTCGTGGATGCC

TGGGTTTCAGTCGATGCAAACGAGGATCTTATTCAATGAAGCTTTTAGCA

GAGGGCTTCGTATCATGCAGATTGTCACTGGGAAGAAATCAAAAGGCGAT

GTCGAAGTTGAAAAAGAAGGTAA

SEQ ID NO. 6

CTGTCAGATTTAGTTTCACAAAATCTTTGTAACTTCGCGGTTTTTGATAT

GGAAGTTGCTACAAAAACTGACTTGTGATATTATAATCTTTCGGCAAGAA

AAATATATAATACTAATTTCAGAAAGTATTCTGTTGAATTGTTGATCACC

AAATACACATAAACCGGCAGATGTTGACATGTTTACGTGGGATCACTGGG

ATAGAAGTTTTGCTTCTGTATTAGTATCGCGAACCGGTTTGTAGTAGCGA

AAATAACATTATTATTTTCAGATTTCATCATCGTCAAATTCAACGTTACA

TTTGAACAGGCTTGTAAAAAGTGGACATGTGGCATGAGTAAAAGATAAAG

AAAATTGTGAGCCTTTTTGTTAATACGAAAAAGCCGAAAACGTTATTATT

TCTATCATCGGCAAATTTAATGTTAAATTTGCTCCACATCATTCAGAGGG

TATATGTATATTTTTCTAATGCTTCGGTGAAGCACATGCGACCATTTGTT

GCGTCAGAAGTCAGAACAAAAGGAAGATTCCATCTAATGGATTATAATCC

CACATGCCCATTTTTAAAACTAGACAAATAACTTATAATAGTCCCATAA

GAGCATTAAGACAAACTGAACCAAAAAGAATCTTAAATGCTGGTGAATCT

AGTCTCGAATGCTGCTGAACACTCCTGATATTAGAATTTGGCAGAAAATA

TTCATACTAATAACAGTAAATACATTTCAAAACAAGAAAATAGTAGTAGT

AAATAAAAACAATTAATATGTTATTATTGTTTCTCTTAGCTGTTACCATT

ACATTAACAATTTACATTCAATCCTTTTAATGAAAAATATTATAAAATAT

TAAAAGAAGTTATTAGAAAAGGAGAGGGATATGGGGGGGGGAGAGCATGG

AGGGGTCCCATGTGTGTTTCGAAAAGCAGCAAACATGACTTTGTAAAGTC

TTGTTTTAGCTAGAGTTCCAAAAAAAAAAGAGTTCAAAAAAAAAGAAAAA

AAAAAGTCTTGTTTTAGCGTCCAAAGCGGTCTCACTCGCCGTTCAGCTGT

TAAATTTTCTTGAAATAAATCGCTCCACTTGTTTTTTATTTTTGTTTCTT

TCAACCCACTTGTATTAATAACAATAATGATATTGCTAATCTTGAACAAA

TCGTGGATTGTCTTTTCTTCCAGTGATATCATCCTTAGTCAAAACATCTC

AAATTAAATAAATATATAGTTGTGAATTAAAAAAAAAGGTATAGAGTTTAT

AAAATTAGCATTTGCGAATGTTTTTAAAAGTTTGGCGTTTGTATAGATCA

CTGTCAGTGTCATGAATCATTCGGTGACAGCAAATTTGTATATGCCAAAA

AAGAGAGTTGATACTTGCCATTCTCGATATTTTGAATTTTTTTTCGTCGA

CATACAAACTCAACATTTTCGAAATCTTAGATTAAAAACAAAATGGACAA

AACGATACTTATTAATGAATTATGTACTAGCGTCTGAACATTAGTAACAT

AGATATAATTATAAGAACAAGAAACATATATGCACAAAGCCTCAAACCAA

ATTTAAATAGTGTTACGAAACAAGGGATGTACTTGTTATGAAAAATTAAT

GTATAACCATTCTTAGCATTTTTTACCTAACCCTTAAACTTTATAAAGAA

AAATATGTAACATTTCGGTGTGTGGTATATAAAAGTATTTTGAAAATCGA

TTTGATTATTTCTATTATTAAAATGTACTTACTTTTTTTATCACACATTT

ATTTACAATTTCAGAGTTAAACATGATTAAGACAAAGTAGTGAAAATATA

GATGATCTACCAGAAAATCATTTGCTTTCTGAGTGAGATCAAAATAAAGG

CAAAAATAATGTGATGATTGTATATTAAACAATTATTTTGAATTTGAAAA

GAATAACTCATCGAATGAAGCCTATGAACCGAGTAAGCGGTGAAGCGGTT

GGACCGTCACAAAAATTATGACCAACAAGAAAATAAAATTGATATTAGTG

AAGGGCAATTGTCAATAATAGCACCTTTTGAAGTTTATGTCTCAAAAATA

GCACTAGAAGGAGAAAGTCACAAAAATGACATTCATTAAAGGGTAAAATA

TCTATAATACCCTTGGTTTAAAATTAAATAAACAAACTAAAATAAATAAA

AATAAAAAAATAAAAAAAATAAAAATAAAAAAAATAAATTTTTTTTTATA

GTTTCAGATTATATGTTTTCAGATTCGAAATTTTTATAATTTTTTTTTAA

AAAAAAATTTTAAATCTTTTTTTTATTTTTTTTTCAGATTTTATTTTTAT

AATTTAAAAATACTTTTTGAAACTGTTTTTAAAATTTTTATTTTTTATTT

TATTATTTATTATTTATAAAATTTTAAATCCTAATTCCAAAACCCCACCC

CTTAACTCTAAACCCTAATGTTTGGATTAATTAACCCTAGGGGTATAAGT

GTACATTACCTCTTTAATGAAACCTATTTTTGTGACTTTGAACCTTGAGT

GCTACTTTGGGAACAAAAACTTGGTTTGGTGCTATTCTAGTATTTTTCTC

ATTAGTGAATGATATATTTTAGAAAGTAATAAATTGGTTCCAGATTTCAA

TACATCAATGTTTTTCTAATGCTGACTTGCTTTTCCTCTTTTTTCTTACAT

GATAAGGAAACGAGAGAGGTCGAAGAAACAAAGAAACTTCCTAAGCATTT

AGCAACGCATCTTCAAAAAATCTAGTATTTACCAAGTAAAATCATACAAA

ATAAGGAAAAAAGAAGAATATATTTCCCAATTTGGTTTTCACCGGAAAA

AAAAAACTGTCTTAACAAAATCTTAATGCACCAAATCATATAAGAACTTT

ATTTGACCATTGTCATTAGTTTTTTTCCTTATGGTAATGGATCTTCAAATA

ATTTAAATTAAATTAAAAAAAAAAAGAAAAGAGAAACAAAAACGCGGAAA

GGAGAGCCCAAATCGTCTCCGTCTGTCATTGTCGCAGTCTCTAAAAGAGA

AAAACAAATCGCAACGCTTCTCTCTCTCTCCCTATCGTTTGAATCAGTCT

CTCAAGATCCACCACCACCACACATGCTACTATGAGCCTCCGCCACCGCA

CCGTCCCCTCTCAACCCGGACGGCCCCCGGCGGCGGGCGCAATCGAGGAC

GAGCCCTACAACATCATCCCCGTCAACAACCTCCTCGCCGACCACCCCTC

CCTCCGCTACCCCGAGGTCCGCGCCGCCGCCGCCGCCCTCAAAACCGTCG

GCGACCTCCGCCGCCCCACCTACGTCCAATGGCGCCCCCACTACGACCTC

CTCGACTGGCTCGCCCTCTTCTTCGGCTTCCAGAAGGACAACGTCCGCAA

CCAGCGCGAGCACCTCGTCCTCCACCTCGCCAACGCCCAGATGCGCCTCA

CCCCGCCGCCGGACAACATCGATTCCCTCGATCCCGCCGTCGTCCGCCGC

-continued

TTCCGCCGCAAGCTCCTCGGTAACTACTCCAGCTGGTGCTCCTACCTCGG

GAGGAAGTCCAACATCTGGATCTCGGATCGGACCCCCGATTCGCGGCGGG

AGCTTCTCTACGTCGGCCTCTACCTCCTCGTGTGGGGCGAGGCGGCGAAT

CTTAGGTTTATGCCTGAGTGTATCTGTTACATCTTCCACAATATGGCCTC

GGAGCTTAACAAGATCCTCGAGGATTGCCTCGACGAGAGCACGGGGCAGC

CGTATTCTCCTAAGATCACGGGGGAGAATAGTTTCCTAAACGGCGTCGTT

AAGCCTATCTACGAGACTATTAAAGCTGAGATTAACGAGAGCAAGAACGG

GACGGAGCCGCATTGTAAGTGGAGGAACTATGATGATATTAATGAGTACT

TTTGGACGGATAGGTGTTTTAGTAAATTGAAATGGCCGATTGATTTGGGG

AGCAGTTTCTTCAAGAACAGCAGAGGTAGCGGCGTTGGGAAGACTGGTTT

TGTGGAGAGGAGGACGTTTTTTTACCTCTACAGGAGCTTTGATAGGCTTT

GGGTGATGCTTGCTTTGTTTCTTCAAGCTGCTATTATAGTTGCTTGGGAG

GAGAAGCCGGGTGGAGGGTCGGTGACGAGTCAGCTCTGGAATGCGTTGAA

GTCGACGGATGTTCAGGTGAGGCTTTTGACTGTGTTCTTGACGTGGAGTG

GGATGAGGTTGTTGCAGGCTGTGTTGGACGCTGGCTCGCAACGGTCGCTT

ATTTCTAGAGAGACCAAACGGCTGTTTTTTCAGAATGTTGATGAAGGTTGT

GGCTGCTACGGTTTGGATAGTAGCGTTTATTGTTCTCTACACGAACATCT

GGAAGCAGAGGAAGCAAGATAGGCAGTGGTCCAGAGCCGCGAATGATAAG

ATTTATCAGTTCCTTTACGCTGTGGTGGCTTTCTTGGTCCCTGAGATCCT

GGCTTTGGCTCTGTTTATAGTCCCGTGGATAAGGAACTTTCTGGAAGAGA

CGAATTGGAAGATATTCTTTGCTTTGACTTGGTGGTTCCAGGGGAAAAGC

TTTGTGGGTCGAGGTTTGAGAGAGGGGTTGGTGGACAACATCAAGTACTC

GACTTTCTGGATCTTTGTCCTTGCAACGAAGTTTACGTTCAGCTACTTCC

TGCAGGTTAAGCCAATGATTAAACCCTCGAAGCTGCTATGGAATTTGAAG

GAGGTGGATTATGAGTGGCATCAGTTCTTTGGCGAGAGCAATAGGTTTTC

TGTCTTGTTATTGTGGCTGCCAATGGTGTTGATATACCTGATGGATATCC

AAATTTGGTACGCGATCTATTCTTCGATTGTTGGTGCTGTTGTTGGGCTG

TTTGATCATCTGGGGGAGATCAGGGACATGGGACAGCTTAGGCTGAGGTT

TCAGTTCTTTGCTAGCGCTATTCAGTTCAACCTAATGCCTGAGGAACAAC

TCCTGAATGCTAGAGGATTTGGTAACAAGCTTAAGGACGCCATTCATAGG

TAAGTCTATTGAAGCATGTTACTGATATTTCTATATAATTTACTATATAG

TTTGTCTTTACAGTACAAGCTATGGGATTTTAGTTTTGTTAAAGCAGATT

TCTCCGCAATGAACTCGACTTTTCACATTGTAATAACATTGAGTTTGTGT

ACTTTATGCAGATTGAAGCTGAGGTATGGATTGGGGCGGCCGTTTAAGAA

ACTCGAGTCCAATCAGGTTGAGGCTAACAAGTTTGCGCTGATCTGGAATG

AGATAATCCTAGCTTTCAGAGAGGAGGATATAGTCTCTGATCGAGAAGTA

GAGCTGCTGGAGCTGCCAAAAAATTCCTGGAATGTGACAGTTATCCGCTG

GCCGTGTTTTCTGTTGTGCAACGAGCTTTTGCTTGCACTGAGCCAGGCGA

AAGAGCTGGTTGACGCACCTGATAAATGGCTGTGGCACAAGATATGCAAG

AATGAGTACAGGCGGTGTGCTGTGGTTGAGGCATATGAAAGCATCAAACA

-continued

TCTGTTGCTCTCAATCATCAAAATTGACACCGAAGAACATAAAATTGTTA

CAATTTTCTTTCAGATGATTGAGGTGTCTATTCAGGGTGAGCAGTTCACC

AAGACCTTCAAAGTGGACCTTTTTGCCAAAGATTTATGAGACACTACAGAA

GTTGGTTGGGCTGTTGAATGATGAGAAAGTGGATGTTGGGCGAGTGGTGA

ATGGTCTGCAGTCTATTTATGAGATTGCAACACGACAGTTCTTCCTAGAA

AAGAAGACGACTGAACAGCTATCTACTGAGGGGTTAACTCCTCATGATCC

AGCCTCAAAGTTACTGTTTCAGAATGCTGTTAGGCTTCCCGATGCAAGCA

ATGAAGACTTCTTCCGGCAGGTTAGGCGGTTACACACAATTCTCACTTCT

AGGGACTCTATGCACAGCGTCCCTGTGAATCTAGAGGCGAGACGGCGGAT

TGCCTTCTTCAGCAATTCGCTCTTCATGAACTTGCCTCATGCACCTCAGG

TGGAGAAAATGTTGGCGTTCAGTGTTATGACTCCATACTACAGCGAGGAA

GTTGTATACAGCAAAGAACAGCTCCGAAATGAGACTGAGGATGGGATTTC

AACCTTGTATTACCTGCAGACGATTTATGCCGACGAATGGAAAAATTTTA

AGGAACGGATGCGGAGGGAAGGTATAAAGACAGATGTTGAGTTGTGGACA

ACCAAGCTGAGAGAGCTCAGGCTTTGGGCTTCCTACAGAGGTCAGACTTT

GGCACGTACAGTTCGAGGAATGATGTACTATTACAGGGCTCTTAAGATGC

TTGCTTTTCTTGACTCTGCGTCTGAAATGGACATTCGGGAGGATGCTCAG

GAGCTTGGTTCAATGAGGAGTTCGCAGGGAAATCGATTGGATGGGGTGGA

CGATGTAAATGACGGATCTTCTCTAAGCAGAGCAACTAGCTCTGTGAGCA

TGCTGTATAAAGGCCATGAGCATGGGACTGCATTGATGAAATTCACATAT

GTCGTGGCGTGCCAGATCTATGGGTCTCAAAAAGCGAAGAAGGAGCCTCA

GGCCGAGGAAATTCTGTATCTTATGAAGCAAAACGAAGCCCTCCGTATTG

CATATGTGGATGAGGTGCATGCGGGCAGGGAAGAGACTGAGTATTACTCC

GTTCTGGTGAAATACGATCACACGTTGGAGAAGGAAGTGGAGATATTCCG

TGTGAAGCTACCTGGTCCGGTGAAGCTGGGTGAGGGAAAGCCAGAGAACC

AGAATCATGCAATGATCTTTACCCGCGGTGATGCTGTTCAGACCATAGAT

ATGAACCAGGATAATTATTTTGAGGAGGCTCTCAAGATGAGAAATTTGCT

CCAGGAGTTTAGGCATTACCATGGGATCAGAAAGCCAACTATTCTTGGTG

TCCGGGAGCACATCTTCACGGGATCTGTCTCGTCTCTGGCTTGGTTCATG

TCTGCTCAGGAGACAAGTTTCGTCACTCTTGGTCAGCGTGTTCTAGCCAA

CCCGCTGAAGGTCAGAATGCATTATGGTCACCCTGATGTATTTGACAGAT

TCTGGTTCTTGAGTCGAGGTGGCATCAGCAAAGCTTCTAGAGTTATAAAT

ATCAGTGAGGACATCTTCGCCGGGTTTAATTGCACATTGCGGGGCGGTAA

CGTCACCCACCACGAGTATATTCAGGTAGGGAAATGTTCATCATTTGGAT

ATTCTAACTAATTTATACATCGACAACAATACTATAATTCCACTTTTTTT

TTGTTATAACCTTTTTGTGTGTGCATATATGTATTCAGGTTGGGAAGGGT

CGAGATGTTGGATTGAATCAAATATCAATGTTTGAGGCTAAGGTAGCCAG

TGGGAATGGAGAGCAGGTTCTTAGCCGAGATGTGTACAGGCTGGGTCATA

GGCTCGATTTCTTCAGAATGTTATCATTTTTCTACACAACGGTGGGGTTT

TTCTTCAACACGATGATGGTCATTCTCACTGTCTACGCTTTCCTCTGGGG

CCGGGTTTATCTTGCTCTGAGCGGTGTTGAGAAGTCCGCTCTAGCAGACA

GCACAGACACCAACGCAGCGCTTGCTGTGATATTGAACCAGCAGTTCATC

ATTCAGCTTGGTCTCTTCACAGCTCTGCCAATGATTGTGGAATGGTCTCT

CGAGGAAGGTTTCCTTCTCGCGATATGGAACTTCATTCGGATGCAGATTC

AGCTTTCCTCTGTCTTCTACACATTCTCAATGGGGACCAGAGCTCACTAT

TTTGGCCGAACCATTCTCCACGGTGGAGCAAAGTACAGAGCCACTGGACG

TGGATTTGTTGTCGAGCACAAGAGTTTCACTGAAAACTACCGTCTATACG

CACGCAGTCACTTTGTGAAGGCCATCGAGCTTGGGCTGATCCTCATAGTC

TACGCTACGCACAGTCCCATCGCCAAAGACTCATTGATCTACATAGCCAT

GACTCTCACCAGCTGGTTCCTCGTGATTTCATGGATACTGGCCCCTTTTG

TGTTCAACCCGTCAGGATTCGACTGGCTTAAGACGGTCTATGACTTCGAA

GGCTTCATGAACTGGATCTGGTATCAAGGCAGAATCTCAACGAAGTCCGA

ACAGAGCTGGGAGATATGGTGGTATGAGGAACAGGACCACCTGAGAACCA

CCGGTATACCAGGAAGAATCATGGAGATAATCTTGGACCTTCGGTTTTTC

TTCTTCCAGTACGGGATTGTATACCAGCTCAAAATCGCAAACGGATCAAC

CAGCATTCTCGTCTACTTACTCTCATGGATATACATCTTTGCAGTGTTTG

TGTTCTTCCTAGTGATCCAATACGCCCGTGACAAGTACTCTGCGAGAAAC

CACATACGGTACAGGCTCGTCCAGTTCCTCCTGATCGTGTTTGGTACACT

GGTGATTGTTGCTCTCCTCGAGTTCACGCATTTCAGCTTCGTGGATATCT

TCACGAGTCTTCTTGCGTTCGTCCCAACCGGCTGGGGGATCTTGCTGATC

GCACAGGCTTTGAGGCCCGCGCTGCAGAAGATCGGGCTTATCTGGAACGC

GGTTATCTCCCTTGCTCGGTTGTATGACATACTGTTCGGGATAATCATCA

TGGTTCCCGTAGCGTTCATGTCGTGGATGCCTGGGTTTCAATCGATGCAA

ACGAGGATCTTATTCAATGAAGCTTTTAGCAGAGGGCTTCGTATCATGCA

GATTGTCACTGGGAAGAAATCAAAAGGCGATGTCGAAGTTGAAAAAAGAA

GGTAAAGCTTCTTATTTACCCAAACATATTTTATGTTCTGTTTGTTTGGA

ATCTTAAATTACAACAACACTAATGCAAAGCTTTTATAACTTGTGTAGGT

CTTGAGGTATATGGTAATTTAAAAGTTGCTGGTTTGCGGCGATGAGGTTA

GTTTTGTATTCTTATAAGTTATGCTTCTTGTCTGAATAAGAACTCAGACA

CCCGTGTTTTGTCTTCTTCTTATTTTAAACCAGGTTTTTGGAGAGCTTTG

GTTGAGGAAGCTATTTGATTAGTTCATCGGTTAGTGGGAGAAACATATAT

ATATACATTTGTCAGTACTTTGTTAGAGTGTGTGGAGGTGGGGACGACTC

TGATTCTGATTCCTTATGTGGTTATTGTCTGAAACGTTACAGCATTTTGT

GAAGTAGGCTTTTGTGCAAGATTTGATATCTTTCTCTCATTGTAGAGCTT

TAGAGCATTTTTTAGTATATGTTTAATCTTTGATTTTCTAATGTCATTTG

CATTCATATTCACATCTTCTCTGCTTCTTCGTTGTCTGAAACCAGTTTTC

AGATGCTTATCCATTGTCCA

SEQ ID NO. 7

TATCATTGTCGCAGTCTCTCTCACAGCTAAAAGGAAAACAGATCGCAACG

CTTCAATATCTCTCTCTCTCCATTGTTTTGAATTGAATCAGTCTCCTCAC

CCTTCTCCAAGATCCACCACCACCACATGCCACTATGAGCCTCCGCCACCG

CACCGTCCCATCTCAAACCGGACGGCCGTCGGCGGCGGGAATCGAGGAGG

AGCCCTACAACATCATCCCCGTCAACAACCTCCTCGCCGACCATCCTTCT

CTCCGTTACCCCGAGGTCCGCGCCGCCGCCGCCGCTCTCAAAACCGTCGG

CGACCTCCGCCGTCCTCCCTACGTCCAATGGCGTCCTCACTACGATCTCC

TCGACTGGCTCGCCCTCTTCTTCGGCTTCCAGAAGGATAACGTCCGCAAC

CAGCGCGAGCACATGGTGCTCCACCTCGCCAACGCTCAGATGCGTCTCAC

GCCGCCGCCGGATAACATCGATTCCCTCGATTCGACGGTTGTCCGTCGCT

TTCGCCGGAAACTCCTCGGAAACTACTCGAGCTGGTGCTCTTATTTAGGG

AAGAAATCGAACATCTGGATCTCGGATCGGAACCCTGATTCGAGGCGGGA

GCTTCTCTACGTTGGCCTCTACCTCCTCGTGTGGGGCGAGGCGGCGAATC

TTAGGTTTATGCCTGAGTGCATCTGTTACATCTTCCATAACATGGCCTCG

GAGCTTAATAAGATTCTGGAAGATTGCCTCGATGAGAACACGGGGCAACC

CTATCTGCCTACTCTCTCGGGGGAAAACGCTTTCCTAAACGGCGTCGTTA

AACCTATTTACGAAACTATCAAAGCTGAGATTGATGAGAGCAAGAACGGG

ACGGAGCCGCATTGTAAGTGGAGGAACTATGATGATATTAATGAGTATTT

CTGGACGGATAGGTGTTTCAGTAAATTGAAGTGGCCGCTTGATCTGGGAA

GCAGTTTCTTCAAGAGTAGTAGAGGGAAAAGCGTTGGGAAAACCGGTTTT

GTGGAGCGCAGGACCTTCTTTTACCTCTACAGGAGCTTTGATAGGCTTTG

GGTGATGCTTGCGTTGTTCCTTCAGGCCGCCATTATAATTGCTTGGGAGG

AAAAGCCGGATAGAGGGTCGGTGACAGGGCAGCTGTGGAATGCCTTGAAG

TCCAGAGATGTCCAGGTGAGGCTTTTGACAGTTTTCTTGACGTGGAGTGG

GATGAGACTACTGCAGGCTGTGCTGGACGCTGGTTCGCAACGGTCTCTTA

TTTCTAGAGAGACCAAACGGCTCTTTTTCAGAATGTTGATGAAGGTTGTA

GCTGCCACAGTTTGGATAATAGCTTTTATTGTACTCTACACGAACATCTG

GAAGCAGAGGAAGCAAGACAGACAGTGGTCCAGAGCCGCGAATGACAAGA

TCTACCAGTTCCTTTACGCTGTGGTGGCCTTCTTGATCCCTGAGATCCTG

GCTCTGGCCCTGTTTATAATCCCGTGGATTAGGAACTTTCTGGAAGAGAG

CAATTGGAAAATATTCTTTGCTTTAACTTGGTGGTTCCAGGGTAAAAGCT

TTGTGGGTCGAGGTTTGAGAGAGGGTTTGGTGGACAACATCAAGTACTCG

ACGTTCTGGATCTTCGTCCTAGCAACAAAGTTCACATTCAGCTACTTCCT

ACAGGTTAAGCCAATGATTAAACCCTCGAAGCTGCTGTGGAACTTAAAGG

AGGTAGATTATGAGTGGCATCAGTTCTTTGGCGAGAGCAATAGGTTTTCT

GTCTTATTATTGTGGCTGCCAGTGGTGTTGATATACCTGATGGATATCCA

AATTTGGTACGCAATCTATTCTTCGATTGTTGGTGCTGTTGTTGGGCTGT

TTGATCATCTGGGGGAGATCAGGGACATGGGACAGCTTAGGCTGAGGTTT

CAGTTCTTTGCTAGCGCTATTCAGTTCAACCTGATGCCTGAGGAACAACT

CCTGAATGCTAGAGGCTTTGGTAACAAGCTTAAGGACGCCATCCATAGGT

AAGTCTGTGGAAGCATGTTACTGATTTCCTTTAGAGTTTAATGTACAGAG

TTTGTCTTTACGGTACAAGCTATATAATTTTAGTTTTGTTATAGCAGATT

CTCGTAACTTGACTTTTTAACATTGTTATAACCTTGAGTTTGTGTACTTT

ATGCAGATTGAAGCTGAGGTATGGATTTGGGCGGCCGTTTAAGAAACTCG

```
AGTCTAATCAGGTTGAGGCCAACAAGTTTGCTTTGATCTGGAATGAGATA

ATCTTAGCTTTTAGAGAAGAGGATATTGTCTCTGATCGAGAAGTAGAGCT

ACTGGAGCTGCCAAAGAATTCCTGGAATGTGACAGTTATCCGCTGGCCGT

GTTTCCTGCTGTGTAACGAGCTTTTGCTTGCACTGAGCCAGGCGAAAGAG

CTGGTTGATGCTCCTGATAAATGGCTGTGGCACAAGATATGCAAGAATGA

GTACAGGCGTTGTGCTGTGGTTGAGGCATACGACAGCATCAAACATCTGT

TGCTCTCGATCATCAAAATCGACACTGAAGAACATAAAATCATCACGGTT

TTCTTTCAGATGATTAAGGTTTCTATTCAGGGAGAGCAGTTCACCAAGAC

CTTCAAAGTGGATCTTCTGCCAAAGATTTACGAGACACTACAGAAGTTGG

TTGGGCTGTTGAATGGTGAGGAACCGGATATCGGGAGAGTGGTGAATGTT

CTGCAGTCTATATATGAGATTGCAACACGACAGTTCTTTATAGAAAAGAA

GACAACTGAACAGCTATCTACTGAAGGATTAACTCCTCATGATCCAGCCT

CAAAGTTACTGTTTCAGAACGCTGTTAGGCTTCCCGATGCAAGCAATGAA

GACTTCTTCCGGCAGGTGAGGCGGTTACACACAATTCTCACTTCTAGGGA

CTCTATGCACAGCGTCCCTGTGAATCTAGAGGCGAGACGTCGGATTGCCT

TCTTCAGCAATTCGCTCTTCATGAACTTGCCTCATGCACCTCAGGTGGAA

AAAATGTTGGCGTTCAGTGTTATGACTCCATACTACAGCGAGGAAGTTGT

ATACAGCAAAGAACAGCTCAAAAATGAGACTGAGGACGGGATTTCAACCT

TGTATTACCTGCAGACGATTTATGCTGACGAATGGAAAAATTTTAAGGAA

CGGATGCGTAGGGAAGGTATAAAGACAGATGATGAGCTGTATACAACCAA

GCTGAGAGAGCTCAGGCTTTGGGCTTCCTACAGAGGTCAGACTTTGGCAC

GTACAGTTCGAGGGATGATGTACTATTACAGGGCTCTTAAGATGCTTGCT

TTTCTTGACTCTGCGTCTGAAATGGACATTCGGGAGGATGCTCAGGAGCT

TGGTTCAATGAGGAGTTCGCAGGGAAATCTGGGCGGTCGATCGAATGGGG

TTGACGATGTAAATGACCGATCTTCTCTAAGCAGAGCTACTAGCTCCGTG

AGCATGCTGTATAAAGGCCATGAGCATGGGACTGCATTGATGAAATTCAC

ATATGTCGTGGCGTGCCAGATCTATGGGTCTCAAAAAGCGAAGAAGGAGC

CTCAGGCAGAGGAAATTCTCTATCTTATGAAGCAAAATGAAGCCCTCCGT

ATTGCGTATGTTGATGAGGTGCATGCAGGCAGGGGAGAGACCGAATATTA

CTCAGTTCTGGTGAAATACGATCACACTTTGGAGAAGGAAGTGGAGATAT

TCCGTGTGAAGCTACCTGGTCCCGTGAAGCTGGGTGAGGGAAAGCCAGAG

AACCAGAATCATGCAATGATCTTTACCCGTGGTGATGCTGTTCAGACCAT

AGATATGAACCAGGATAATTATTTTGAGGAGGCTCTCAAGATGAGAAATT

TGCTCCAGGAGTTTAGACATTATCATGGGATCAGAAAACCAACTATTCTT

GGTGTCCGAGAGCACATCTTCACTGGCTCTGTCTCGTCTCTGGCTTGGTT

CATGTCCGCTCAGGAGACTAGTTTCGTCACTCTTGGTCAGCGTGTTCTTG

CTAACCCGCTGAAGGTCAGAATGCATTATGGCCACCCCGATGTATTTGAC

AGATTCTGGTTCTTGAGTCGAGGTGGCATCAGCAAAGCGTCCAGAGTCAT

AAAATATCAGTGAGGACATCTTCGCTGGGTTTAACTGCACATTGCGGGGCG

GTAACGTCACACACCACGAGTATATTCAGGTTGGTAACTATTCATTATTT

GGTTATTTCTAACTAATTTATACTGCGACAGCAATCCTATATTTCCATAT
```

```
TTCTTTTGTTATAACCATGCAACTTAACGTTCATTGTATCTGAGTGTCAA

TGTAAATTTCATAACCCCTGTTTTTGTGCATATATTCAGGTTGGGAAGGG

TCGAGATGTTGGATTGAATCAAATATCAATGTTTGAGGCGAAGGTAGCCA

GTGGGAACGGAGAGCAGGTTCTTAGCCGAGATGTGTACAGGCTGGGTCAT

AGACTCGATTTCTTCAGAATGTTATCATTTTTCTACACAACGGTCGGGTT

TTTCTTCAACACGATGATGGTCATTCTTACCGTTTACGCTTTCCTATGGG

GCCGGATTTATCTTGCTCTGAGCGGTGTTGAGAAGTCCGCTCTAGCAGAC

AGTACAGACACCAACGCAGCGCTTGCGGTTATATTGAACCAGCAGTTCAT

CATTCAGCTCGGTCTCTTCACAGCACTGCCAATGATTGTGGAATGGTCTC

TCGAGGAAGGTTTCCTTCTTGCGATATGGAATTTCATCCGGATGCAGATT

CAGCTTTCTTCTGTCTTCTACACATTCTCAATGGGGACCAGAGCTCACTA

TTTTGGCCGAACCATCCTCCACGGTGGAGCAAAGTACAGAGCCACTGGAC

GTGGATTTGTTGTCGAGCACAAGAGTTTCACTGAGAACTACAGACTGTAT

GCACGCAGTCACTTTGTGAAGGCCATCGAGCTTGGGCTGATCCTCATAGT

CTACGCTACGCACAGTCCCATCGCCAAAGACTCATTGATCTATATAGCCA

TGACTCTCACCAGCTGGTTCCTCGTGATATCATGGATACTGGCTCCATTT

GTGTTCAACCCGTCAGGTTTCGACTGGCTTAAGACGGTCTATGACTTCGA

AGGTTTCATGAACTGGATCTGGTATCAAGGCAGAATCTCAACGAAATCCG

AACAGAGCTGGGAGATATGGTGGTACGAGGAACAGGACCACCTGAGAACC

ACCGGTATACCAGGAAGAATAATGGAGATAATCTTGGACCTTCGGTTTTT

CTTCTTCCAGTACGGGATTGTATACCAGCTCAAAATCGCAAACGGATCAA

CCAGCATTCTCGTCTACTTGTTGTCGTGGATATACATCTTTGCTGTGTTT

GTGTTCTTCCTGGTAATCCAATACGCCCGTGACAAGTACTCTGCGAAAAA

CCACATACGGTACAGGCTTGTCCAGTTCCTCCTGATCGTGTTTGGTATTC

TGGTGATCGTTGCTCTGCTGGAGTTCACGCATTTCAGCTTCGTGGATATC

TTCACGAGTCTTCTTGCGTTCGTCCCAACCGGCTGGGGAATCTTGCTGAT

CGCACAGGCTTTAAGGCCTATGCTGCAGAAGTTCAGGCTTATCTGGAACG

CTGTTGTCTCCCTTGCTCGGTTATATGACATACTGTTGGGGGATACTCATC

ATGGTTCCCGTAGCATTCATGTCATGGATGCCTGGGTTTCAGTCAATGCA

AACGAGGATCTTATTCAATGAAGCTTTTAGCAGAGGGCTTCGTATCATGC

AGATTGTCACTGGGAAGAAATCAAAAGGCGATGTCTAAGTTGAAAATGAA

AGAAGGTAAAGCTCTTTATTTACTCAAACATCTTTTATGTTCTGTTTGTT

TGGAATCCTAAGATTACAACAAAACCAATGCAAAGCTTTATAACTTGCGT

AGGTCATAATAAGGTACATGGTAATTTAAAGTTGTTGGTTTGCGGCGTTG

AGATCAGTTGGAGGTTAGTTTTCTCGAGACATGGTATTCTATAAGTTATT

GCTTCTTGTCTGAATAAGAACTCAAAAGAAAAACCATGTGTTGTTGTTGT

TGTCTTCTTCTTAAAGCAGGTGTTTGGAGAGCTTTTGTTGAGGAATCTGG

AAGTTGGGTTAGATCATGGGTTAGCGGGTGAAATATATATTGTCAGTACT

TTGTTAGTGTGTGGAAATGGGACTCTGATTCTTGTTGTCTGAAACGATAC

AGCATTTTGTGAAGTAGGGCTTTTGTGAAAGATTTGTTTCTCTTTCTCTC
```

-continued

TCAGTGTAGAGCTTTAGAGCATTTTTTTAGTATATGTTTAATCTTTTTATT

TTCTAATGTCATTTGCATTCATATCTCACGTCTTCCTCGTTGGTCTGAAA

CCGGTTTTGAGATGCTTATCCATTGTCCACTTCTCTATG

SEQ ID NO. 8

CAAACGATCATAGAAATGTACCTGTAATTAGTCAACTGTTCAAAGAGCTT

AATGCATTGCTCCTTATCAATCTGCCCGGTTTTCTGTCATAAACATGAAA

TAGAATACAACGTAAACACATATGTTTAGCTATGTGGTAACTAACAGGGA

GCTTCCCTGTATATATCTGTAGGAGGTAAAAATCATTTTGAATGGAGTAA

CTTACGTCTTTGTCTATAAGACCAAAGGCTTTCTCCAGCATTCTTCTCTT

CATTTGATCCATTCCAGATACTTGCTTTGCGAGCTACAAAAATAACAAAT

ATGATACCACGCTAGTGCGGTCGTTTTTAGTTTTAACATACAAAAGATCA

AGTTTTGCAATAAACCTGTTCTTTGAAACTGTCATAAACAACGGCAAGAA

TCAAGTTCGTGACAAAGTAGACGCCAATTAGTACGTAGAGCACGAAGAAC

AACGAAGACCAGCGTGAAGACCTATACAAAAAAAAAAAAGAACAAATCAG

TCGCCCAAAACACTGGATGTAACTCATTTCACCATATAAACTTACTTGTA

AGCACGAATCCAGACATCAGGATTGTTGGATGTTGTGAACAAAATAAACA

TCTGGTAAAGAGTTGCACCGTAAGACGTGAAGACCGTGAGTCCTTGTTGT

GTATCCTCAAACATAACAAAAGCAATCCAACTGGCAAAGAGAAGGAACAG

CATCCATAGAGCCTGTGGAGATATTCAAGAAGTGAAAGCATAGAAGGACA

ATCAATACGAGTTCATCACTGTTCTGAAAGTCAAACTCGATTGGGAAGAC

CACTGACCAAGATATTCAAGTATGTGCCAAGCATTCCAGAAAGAAGGACG

AGGCTGTCTCGAAGTTCCCTGTACAGAAATTTTAAGAAACACAGTTTTTA

GACAAGAAGATAATATAAAACAAAAGTGCACTTTCATCGTAAATGGCATT

TTGGATTGAGACAAGTTGATAGAAAAGAAGCATAAATATGTGTTGATACC

TTATGCTGAGGATGAATATGATAACTCTGACATATGGGGCGATTCTAAAA

GGAAGAAAATCGAAAGCCACTGGAGACAAGTATAGAATGTCAACGAGCAC

ATCAACAATCAAAACTACCACGCAAGCAACCTGGAATCAGGAAGAAGAAG

ACATTTATTGTGTTAAAAGTTATGAAATCAATATCTTAAGTTCTGTCCAA

CATTCAACAAATAGAAAAGAAAAAAAAAAGAAACAGTGAAGAAGACTTAT

GTAGGGGAGAATACCTTCACTAGGTTAAGGCGGCTTGTCCAAAAGATACG

GGACCCTTCATAGGAGATTGGGAAAAAAGTATGTACAAGTAGTATAACCA

GGGTAAGTACCTGTTTGGAGAAAGCAAAAATATAAGAATTTCAGTACAAT

GAGAAAGGATCCTGGCTAGTCCGAACGATAAGATAACGAGTATATAAATA

TTAGCATCTACTTAAACGAGATCAACTAGTTTTCACAAAAGTGTGTAATG

AATCTCAAGCCTTGAACTTTCAAGTGGATGCATATAAGAATATGTCAGTA

CAGTGAGAAAGGATCCTGGCTAGTCTAGTCCCAACAATATACACCATGGA

AGATAAGACGAGTATGTTAATAAAATTAACAACTTCTTAAACGAGATCAA

CGAGTCTTGAATCTTTCAAAAGTGGGTTAATATGAATCTGGTGTGCCTAA

TTGCACTAAAATCTATTTGCATCTACAGCGAAATGAAAGGCCAGCTACT

TGCCTCAAAGATAATGGATTCTGCATTGGTCAAGTAGGGTAACTCCCCAA

GGTAATAGTAATCTCTGTCTTTGCAAGACGGCGTAGGCTTATTTTCACAC

-continued

CACAATGGTTGCTGCAAAAAGACAGGACAAGAAAGACTGTCACACTTTTT

TCTATTTTCTTTTAAAAGTATTTTCTTTTGGGGGGGTTGGGGGGGGGGCA

AAAGGTTGCTGACCTCAAAGAAGTTAATCAAAATGAGAGCGAAATAGTTG

AGAGACCAGATGAGATCTAATCGTGTGTAGATAAAGTAGTACTTGGCAGA

CTCTCCGAAGCTGGACTGGTCAAGTATTTGCTCAGGTAGACCTATACCAT

CTTCAGCCTACATACATACAGCAAAATAAATAAATAAATAAATAAAAAGG

TTCTCAAAATCAGCAAAAAAGACAAAGAAACCGAACATTTTCTATTGCTA

TATTCGTAACTTATTATCAGGTTAAAGAAACAAATCATTTTGAACAAAAA

AAAAAAAAAAAGAAACAAATCATATTCTGAGCAATTATTCAGAATAAACG

ATTTGGACTTGTCAGACTGATTCTATTCACTGATAAATTGAGAAATCTCC

CTCAAGGGAGTTATGCCATCATGTCACAGTCAGTCGGACAAAGATCCATG

AATTTTATCAGAACAAGAAGAAGACAAATATAGTTAGGGAGTTGAGAGAT

AGAAAGAGAACCAGATCGACGAGAGCAGCAGCTTTCTGAAAGGTGGTACC

ATGAGCGATAGCTTCTGATCTACGAACAATCCGATCCGTACCACCACCAC

GACTCTCTCTACCTATCAAAGGATCTTCCATTTTTTTTTTCTTCAAAAGG

ATCGAAATGGAAAGCAGAAGACCAAGGACCTTATGTAGTACCTTTCTTTC

TTTCTTTCTGTCAGTTTATTGTTGGCTACGAATTTTAATATAATGATACA

GATCACAAGAAGAAGATAGTGATGATGGCCCAGAAGTAGTTGAATTTTTA

AAATAAATTAAATTTTCCAAGTGATATTAGATCTTGCCGACAAACACGTT

GGGGTCCCTTTCTCAATTTGTAACTTTGTGGATCAGGATCTAAGTAGATT

GGTCAAAACTGAGAGAGTGGTGTTGTGGTCCGAATAAAACTGATTAAAGA

ATAAGACTGCAGAGACTAACAAACAGAAGAAACAGATACATAGAGAAGTG

GACAATGGAGAAGCATCTCAAAACTGGTTTAACAAGCAGAGAAGAAGATG

TGAAATATGAATGCAAAATGACATTAGAAAATCAAAGATTAAACATATAC

TAAAAGAAAGTACTCTAAAGCTCTACAATGAGAGAGAAAGAGAAGAAAT

CTGAACACAAAAGCCCTACTTCACACAAAATGCTGTAACGTTTCAGACAA

TAACACCATACAAGAATCAGAATCAGAGTCTTCCCCCCCTTCCCCCACACT

CTAACAAAGTACTGACAAATGTATATATATATGTTTCCCCCACTAACCGA

TGCTCTAACCAGATAACCAACTTCCAAATTCGTCCACAAAAGCTCTCCAA

AAACCTGTTTCAAGCACAAGACAGAACAAAAGATGGGTTTATTTGAGTTC

TTCTTCGCACACCAAGGATAACTTAAAAAAAATTCCATCTCTCGAGAAAA

CTAACTAACCTCCAAATGATCACCATCGCCGCAAACCAACAGCTTTTTCA

AGTTACCATTTACCATACGACCTACACAAGTTATAAAGCTTCGCATTGGT

CTTGTTGTAAATCTTAGGATTCCAAAACAAACAGGATATTAAAGATGTTT

CAGTAAATAAAAGAGCTTTACCTTCTTCTTTCTTCAACTTAGACATCGCC

TTTTGATTTCTTCCCAGTGACAATCTGCATGATACGAAGCCCTCTGCTAA

AGGCTTCATTGAATAAGATCCTTGTTTGCATTGATTGAAACCCAGGCATC

CACGACATGAACGCTACGGGAACCATGATGAGTATCCCGAACAGTATGTC

ATATACCCTAGCAAGGGAGACAACCGCGTTCCAGATAAGCCTAAACTTCG

TCAGCGCTGGCCTTAAAGCCTGTGCGATCAGCAAGATTCCCCATCCGGTT

GGGACGAACGCAAGAAGACTCGTGAAGATATCCACGAAGCTGAAATGCGT

-continued

GAACTCTAGCAGAGCAACAATCACCAGAATACCAAACACGATCAGGAGGA

ACTGAACGAGCCTGTACCGTATGTGGTTTCTCGCAGAGTACTTGTCACGG

GCGTACTGGATTATCAGGAAGAACACAAACACTGCAAAGATGTATATCCA

TGACAACAAGTAGACGAGAATGCTGGTTGATCCGCTTGCGATTTTGAGCT

GGTAAACAATCCCGTACTGGAAGAAGAAAAACCGAAGGTCCAAGATTATC

TCCACAACTCTTCCTGGTATACCGGTGGTTCTCAGGTGGTCCTGTTCCTC

ATACCACCATATCTCCCAGCTCTGTTCCGATTTCGTTGAGATTCTGCCTT

GATACCAGATCCAGTTCATGAAGCCTTCGAAGTCATAGACCGTCTTAAGC

CAGTCGAATCCTGACGGGTTGAACACAAATGGGGCCAGTATCCATGATAT

CACGAGGAACCAACTGGTGAGAGTCATGGCTATGTAGATCAATGAGTCTT

TGGCGATGGGACTGTGCGTAGCATAGACTATGAGGATCAGCCCGAGCTCG

ATGGCCTTCACAAAGTGACTGCGTGCATAGAGTCGGTAGTTCTCGGTGAA

ACTCTTGTGCTCGACAACAAATCCACGTCCAGTGGCTCTGTACTTTGCTC

CACCATGGAGAATGGTTCGACCAAAATAGTGAGCTCTGGTCCCCATTGAG

AATGTGTAGAAGACAGAGGAAAGCTGAATCTGCATCCGAATGAAATTCCA

TATAGCTAGAAGGAAACCCTCCTCGAGAGACCATTCCACAATCATTGGCA

GGGCAGTGAACAGACCAAGCTGAACGATGAACTGCTGGTTCAGTATCACA

GCAAGCGCTGCGTTGGTGTCTGTACTGTCTGCTAGAGCGGACTTCTCAAC

ACCGCTCAGCGCGAGATAAACCCGGCCCCAGAGGAAAGCGTAAACCGTAA

GAATGACCATCATCGTGTTGAAGAAAAACCCGACCGTTGTGTAGAAAAAT

GATAACATTCTGAAGAAATCGAGCCTATGACCCAGCCTGTACACATCTCG

GCTAAGAACCTGCTCTCCATTCCCACTGGCTACCTTAGCCTCAAACATTG

ATATTTGATTCAATCCAACATCCCGGCCCTTCCCAACCTGAATATATGTA

CAAAAAACAAGGGTTATGCAATTTACATTGAAGAAACAAGGAACGTTAAG

TTGCATGGTTATAACAAAAAAAAAAATTGAACTATAGGATTTCTGTCGCA

GTATAAATTAGTTAGAAATATCAAAATAATGAACATTACCAACCTGAATA

TACTCGTGGTGGGTGACGTTACCGCCTCGCAATGTGCAATTAAACCCGGC

GAAGATGTCTTCACTGATATTTATGACTCTGGAAGCTTTGCTGATACCAC

CTCGACTCAAGAACCAGAATCTGTCAAAAACATCGGGGTGACCATAATGC

ATTCTGACCTTAAGCGGGTTGGCAAGAACACGCTGACCAAGAGTGACAAA

ACTAGTCTCCTGAGCAGACATGAACCACGCCAGAGACGAGACAGAGCCCG

TGAAGATGTGCTCCCGGACACCGAGAATAGTTGGCTTTCTGATCCCATGA

GATTTTCTAAACTCCTGGAGCAAATTTCTCATCTTGAGAGCCTCCTCAAA

ATAATTATCCTGGTTCATATCTATGGTCTGAACAGCATCACCACGGGTAA

AGATCATTGCATGATTCTGGTTCTCTGGCTTTCCCTCACCCAGCTTCAAC

GGACCAGGCAGCTTCACACGGAATATCTCCACTTCCTTCTCCAACGTGTG

ATCGTATTTCACCAGAACTGAGTAATACTCTGTCTCTCCCCTGCCCGCAT

GCACCTCATCCACATACGCAATACGGAGGGCTTCATTTTGCTTCATAAGA

TACAGAATTTCCTCTGCCTGAGGCTCCTTCTTTGCTTTTTGAGACCCATA

GATCTGGCACGCCACGACATATGTGAATTTCATCAATGCAGTCCCATGCT

CATGGCCTTTATACAGCATGCTCACGGAGCTAGTTGCTCTGCTTAGAGAA

GATCCACCATTTACATCGTCAACCCCATCCAGTCGACCATTTCCCTGCGA

ACTCCTCATTGAACCAAGCTCCTGAGCATCCTCCCGAATGTCCATTTCAG

ACGCAGAGTCAAGAAAAGCAAGCATCTTAAGGAGCCCTGTAATAGTACATC

ATTCCTCGAACTGTACGTGCCAAAGTCTGACCTCTGTAGGAAGCCCAAAG

CCTGAGCTCTCTCAGCTTGGTTGTCCACAACTCAACATCGTCTTTATAC

CTTCCCTACGCATCCGTTCCTTAAAATTTTTCCATTCGTCAGCATAAATC

GTCTGCAGGTAATACAAGGTTGAAATCCCATCCTCAGTCTCGTTTTTGAG

CTGTTCTTTGCTGTATACAACTTCCTCGCTGTAGTATGGAGTCAGAACAC

TGAACGCCAACATTTTCTCCACCTGAGGTGCATGAGGCAAGTTCATGAAG

AGCGAATTGCTGAAGAAGGCAATCCGCCGTCTCGCCTCTAGATTCACAGG

GACGCTGTGCATAGAGTCCCTAGAAGTGAGAATTGTGTGTAACCGCCTAA

CCTGCCGAAAGAAGTCTTCATTGCTTGCATCGGGAAGCCTAACAGCGTTC

TGAAACAGTAACTTGGAGGCTGGATCATGAGGAGTCAACCCCTCATTAGA

TAGCTGTTCAGTTGTCTTCTTCTCTATGAAGAACTGTCGTGTTGCAATCT

CATAAATCGACTGCAAAACATTCACCACTCGCTCAATATCTGGCTTCTCA

GCATTCAGTAGCCCAACCAACTTCTGAAGTGTCTCGTACATCTTTGGCAG

AAGGTCCACTTTAAAGGTCTTGGTGAACTGCTCACCCTGAATAGAGACCT

CAATCATCTGGAAGAAGATCGTAATGATTTTATGTTCTTCGGTGTCAATC

TTGATGATTGAGAGCAGCAGATGTTTGATGCTGTCATATGCCTCAACAAC

AGCACAACGCCTGTACTCATTCTTGCATATCTTGTGCCACAGCCATTTAT

CAGGAGCATCAACCAGCTCTTTCGCCTGGCTCAGTGCAAGTAAAAGCTCG

TTGCACAGCAGGAAACACGGCCAGCGGATAACTGACACATTCCACGAATT

CTTTGGCAGCTCCAGTAGCTCTACTTCTCGATCAGAGACTATATCCTCTT

CTCTGAAAGCTAAGATTATCTCATTCCAGATCAACGCAAACTTGTTGGCT

TCAACCTGATTAGACTCGAGTTTCTTAAACGGCCGCCCAAATCCATACCT

CAGCTTCAATCTGCATAAAGTACACAAACTCAAGGTTATTATTATGTTGA

AAACTCGAATTCCAAGCTTGTACCGTAAAGACAAACTCTGTATAGTAAAC

TATAAATATAGGAATATGCTTGCACAGACTTACCTATGAATGGCGTCCTT

AAGCTTGTTACCAAAGCCTCTAGCATTCAGGAGTTGTTCCTCAGGCATTA

GGTTGAACTGAATAGCGCTAGCAAAGAACTGAAACCTCAGCCTAAGCTGT

CCCATGTCCCTGATCTCCCCCAGATGATCAAACAACCCAACAATAGCACC

AACAATCGACGAATAGATTGCGTACCAAATTTGGATATCCATCAGGTATA

TCAACACCACTGGCAGCCATAATAACAAGACAGAAAACCTATTGCTCTCG

CCAAAGAACTGATGCCACTCATAATCTACCTCCTTTAAGTTCCATAGCAG

CTTCGAGGGTTTAATCATTGGTTTAACCTGCAGGAAGTAGCTGAAAATGA

ACTTCGTTGCTAGGACAAAGATCCAGAACGCCGAGTACTTGATGTTGTCC

ACCAAACCCTCTCTCAAACCTCGACCCACAAAGCTTTTACCCTGGAACCA

CCAAGTTAAAGCAAAGAATATTTTCCAATTGCTCTCTTCCAGAAAGTTCC

TTATCCACGGGATTATAAACAGAGCCAAAGCCAGGATCTCAGGGACCAAG

AATGCCACCACGGCGTAAAGGAATTGGTAGATCTTGTCATTCGCGGCTCT

-continued

GGACCACTGTCTATCTTGCTTCCTCTGCTTCCAGATGTTCGTGTAGAGAA

CAATAAAGGCTATAATCCAAACCGTGGCAGCTACAACCTTCATCAACATT

CTGAAAAACAGCCGTTTGGTCTCTCTAGAAATGAGGGGCCGTTGCGAACC

AGCGTCCAGCACAGCCTGCAGTAGTCTCATCCCACTCCACGTCAAGAAAA

CTGTCAAAAGCCTCACCTGAACATCTCTCGACTTCAAGGCATTCCACATC

TGCTTTGCCACCGACCCTCTATCCGGCTTCTCCTCCCAAGCAACTATAAT

GGCGGCTTGAAGGAACAAAGCAAGCATCACCCAAAGCCTATCAAAGCTCC

TGTAGAGATAAAAAAACGTCCTCCGCTCCACAAAACCGGTCTTCCCAACG

CTCTTCCCTCTACTATTCTTGAAGAAACTGCTCCCCAAATCAAGCGGCCA

TTTCAACTTACTGAAACACCTATCCGTCCAGAAATACTCATTAATATCAT

CATAGTTCCTCCACTTACAATGCGGCTCCGTCCCGTTCTTGCTCTCATTA

ATCTCAGCTCGGATCGTCTCGTAAATAGGTTTAACGACGCCGTTTAGGAA

AGCGTTCTCCCCAGAGAGAGTAGGCGTATAAGGCTGCCCCGTGTTCTCGT

CGAGGCAATCCTCCAACACCTTGTTAAGCTCCGAGGCCATATTGTGGAAG

-continued

ATGTAACAGACGCACTCGGGCATGAACCTAAGATTCGCGGCCTCGCCCCA

CACGAGGAGGTAGAGACCGACGTAGAGAAGCTCCCGCCTCGAATCGGGGC

TCCGATCCGAGATCCAGATGTTCGATTTCCTCCCGAGGTAGGAGCACCAG

CTGGAGTAGTTCCCGAGGAGCTTGCGGCGGAAGCGGCGGACGACGGCGGG

ATCGAGGGAGTCGATGTTGTCGGGGGGAGGGGAGAGGCGCATCTGGGCGT

TGGCGAGGTGGAGGACGACGTGCTCGCGCTGGTTGCGGACGTTGTCCTTC

TGGAAGCCGAAGAAGAGGGCGAGCCAGTCGAGGAGGTCGTAGTGAGGGCG

CCATTGGACGAAGGGAGGACGGCGGAGGTCTCCGACGGTTTTGAGAGCGG

CGGCGGCGGCGCGGACCTCGGGGTAGCGGAGGGAAGGGTGGTCGGCGAGG

AGGTTGTTGACGGGGATGATGTTGTAGGGCTCCTCCTCGGTTCCCCCCGC

CGACGGCCGTCCGGTTTGAGATGGGACGGTGCGGTGGCGGAGGCTCATAG

TAGCATGTGGTGGATCTTGGAGATGGTGTGAAGGAGGAGGAGACTGATTC

AAAGGATGTGGAGAGAGAGAGAGAGAGAGAGAGAGAGAGAGAGAGAGAGA

GAGATTGAATTGAAGCGTTGCGATATGTTTTTCTCTTTTAGCT

---

What is claimed is:

1. A method for obtaining a *Brassica napus* plant resistant to clubroot disease, comprising the step of knocking out the GSL5 gene in the plant, wherein the knocking out results in the loss of function of the gene, wherein the GSL5 gene is located in subgenome A of the *Brassica napus* and has the nucleotide sequence set forth in SEQ ID NO: 2.

2. A method for obtaining a *Brassica napus* plant resistant to clubroot disease, comprising the step of knocking out the GSL5 gene in the plant, wherein the knocking out results in the loss of function of the gene, wherein the GSL5 gene is located in subgenome C of the *Brassica napus* and has the nucleotide sequence set forth in SEQ ID NO: 3.

3. A method for obtaining a *Brassica rapa* plant resistant to clubroot disease, comprising the step of knocking out the GSL5 gene in the plant, wherein the knocking out results in the loss of function of the gene and wherein the GSL5 gene in the *Brassica rapa* has the nucleotide sequence set forth in SEQ ID NO: 4.

4. A method for obtaining a *Brassica oleracea* plant resistant to clubroot disease, comprising the step of knocking out the GSL5 gene in the plant, wherein the knocking out results in the loss of function of the gene and wherein the GSL5 gene in the *Brassica oleracea* has the nucleotide sequence set forth in SEQ ID NO: 5.

* * * * *

SEQUENCE LISTING

Sequence total quantity: 40
SEQ ID NO: 1          moltype = DNA  length = 8083
FEATURE              Location/Qualifiers
source               1..8083
                     mol_type = genomic DNA
                     organism = Arabidopsis thaliana
SEQUENCE: 1
ctgtcttaaa tggacatttg tagtaacaaa accgaccatc agcaaattaa cgttaacgtt   60
gctctaatcg tgtgtatttt tctaatgctt ggtgaagcac atgcgaccat ttgttgtgtc  120
agaacaaaag gaagattcca catttagaat ttagattata atcccacatg cctattattt  180
aaacatatgt atactgtaat aaaattagtcc cagaagagca tttcatcata ctgtataatt  240
aatcaaattt aaaaaacatt tgtgttgaag agaagatgac tagattcact tgattttttt  300
taatactgat tggtcgtttg accagtcagg atccagactg aaatattctc aaaaggtatg  360
aactatttta atgaaatatt tgagctgaga atttgcttat gggacattct atccttctaa  420
agaaatcatt agaaaatgga gaaaaagtta ctagaaaaag agaggggaaat ggggcgagag  480
tatgaagaaa gggtcccatg tgaatctaat aattgaaaag caaatatgag atttatttta  540
gggttcttgt tttagcgtcc aaagcggtcg cagttgccgt tcagcgactt ttctctgttt  600
atgaaataaa aacgctccac ttgttctttt cttctttcaa cccactttgt tataactatt  660
aacaaatatt gcttggtcca aatttttatta tactgaatta ttttagtttt tttgtatcat  720
catcctcaat gttagttttg aaatcctagg tcagtaagtc aataacgaaa atgacaagtt  780
taattttgta attggaactt acatgtcacg gtctttgttt acgatcattg ccacgaattg  840
tttagatacg ggctttttttt ttctttccgt gttgatgatt atcgtttctt cttacatatc  900
ttgatcaatc actaacattt acataaccta caattttgta atataattgc aatactcgag  960
atcttcaaat ggtgatactg ttaataaaat tacgaacttt taatcatcat caaaatctat 1020
agaaaaagat acataggacc aaaacaagcc taaaacaaag agttataatt tacaaataaa 1080
tgcatgtatt ttgttacttt tgttaaggat tttcatatca atgcatgcat aatgcattct 1140
cttttatttt tatttataat gcattctttt ataatattcg gatccaaaat tatgaattaa 1200
ttccagattg ccataaatgt ctttcttttgt ttatgctgac tttttttcttt tcttaactta 1260
tatagtaagt aaaccagaaa ggtggaagat acaaagcaat ttcattgcat taataaactt 1320
caaatgtatt atccaataat caaaatttat ctagtaattc acaaaaaaaa aaaaatctgt 1380
ctatcattca aaatttcacc aatttggata aatattcaaa aaatttaaa atacaattca 1440
ataacactat taacatatca atcaatatat aacattgcaa aagtttactt gatcattagt 1500
atattcattt taaggttaaa agatctttaa gaaaaggaaa ttcaaattat attgttggaa 1560
aaaaatacaa atcaaagaca gcaaaaaaag taacaaaaaa aaaggtaga agaaactgaa 1620
acgcggaaag gaggcaaaat cttctcgtcg tcgttgtcgc cgtcttcaga gctacaaacg 1680
aaaaaactcg cttccgtttc gatttctcca ttgttattgt ttcttcagtg aagctttttt 1740
cttcgagaaa tttctaagat ctaccacatg ctactatgag cctccgccac cgcaccgtcc 1800
cgccgcaaac cggacggccg ttggcggcgg aagcgtcgg aatcgaagag gagccgtaca 1860
atatcattcc cgttaacaat ctcctcgccg accatccttc actccgtttt cccgaggttc 1920
gtgccgccgc tgctgctctt aaaaccgttg gagaccttcg tcgtccgccg tatgttcaat 1980
ggcgttctca ctacgatctc ctcgactggc tcgccttgtt cttcggtttc cagaaagata 2040
acgttcgtaa ccagcgtgag catatggtgc ttcatctcgc aaatgctcag atgcgtctct 2100
ctccgccgcc ggataatatt gattctctcg attccgcggt tgttcgtcgg tttcgtcgga 2160
aacttctcgc taactactct agctggtgtt cgtatttggg gaaaaaatca aatatctgga 2220
tctcagatcg gaaccctgat tcgagacgag agcttctcta tgttggactc tatcttctca 2280
tttggggaga ggctgcgaat cttcggttca tgcctgaatg tatctgttac atcttccata 2340

-continued

```
acatggcctc tgagctcaac aaaatcttag aggattgcct cgatgagaac accggccaac   2400
cttacttgcc ttctctctca ggcgaaaacg ctttcttaac cggcgtcgtt aaacctattt   2460
acgatactat ccaagctgag attgatgaga gcaagaacgg tacagttgcg cattgtaagt   2520
ggaggaacta cgacgatatc aatgagtact tctggactga tcggtgtttc agcaaattga   2580
aatggccgct tgatttggga agcaatttct ttaagagtag aggcaaaagt gtagggaaaa   2640
ctggtttcgt ggagcgcagg acgttcttct acctttacag gagtttttgat cgactttggg   2700
tgatgctagc tttgttcctt caagccgcca ttatagtagc cttgggaggaa aagccagata   2760
cctcgtcggt aacaaggcag ctgtggaatg ctctgaaggc aagagatgtt caggtgagac   2820
tattgaccgt gttcttgaca tggagtggta tgcgactctt gcaggctgtg ctggacgcgg   2880
cttcacaata tcccctcgtt tccagagaga ccaaaaggca ttttttcaga atgctgatga   2940
aggttatagc tgccgcagtt tggattgtag ctttcactgt cctctacact aacatctgga   3000
agcagaagag gcaagacagg cagtggtcca atgccgcgac gactaagata taccaattcc   3060
tttacgctgt gggggccttc ttggtgcccg aaatcctggc tttggctttg tttattatcc   3120
catggatgag aaacttcctg gaagagacca attggaaaat attctttgct ctaacttggt   3180
ggtttcaagg caaaagcttt gtgggtcgag gtttgagaga gggtttagtg gacaacatca   3240
agtactcgac tttctggatc tttgtcctag ctacaaagtt tacatttagt tacttcctgc   3300
aggttaagcc aatgattaaa ccctcaaagc tgctatggaa cttaaaggat gtcgattatg   3360
agtggcatca gttttatgga gacagcaata ggttttctgt cgcattgtta tggttgccag   3420
ttgtgttgat atatctgatg gatatccaaa tttggtacgc aatctattct tcgattgttg   3480
gtgctgttgt tgggctgttt gatcatctgg gggagatcag ggacatggga cagctgaggc   3540
taaggtttca attctttgct agtgctattc aattcaacct aatgcctgag gaacaactcc   3600
tgaatgctag aggctttggt aacaagttca aggacggcat tcataggtag tccgtggaag   3660
catgctacta atattcctaa ataattttct gtacaacgct tgacttgact gtacaagctg   3720
tgaaatttta cttttgttaa cgcagatgct gcatataatt aaattttttca atattgtaat   3780
aacttgaggt tgtgtactgt atgcagattg aagctaaggt atggatttgg gaggccgttt   3840
aagaaacttg agtcgaatca ggtcgaggcc aacaagtttg cgttgatctg gaacgaaatc   3900
atcttagctt tcagagaaga ggatatagtt tctgatcgtg aagtagagct actggagctg   3960
ccaaagaatt cctgggatgt gacggttatt cgctggccgt gtttcttgtt gtgcaatgag   4020
ctttttgcttg cactgagcca ggccagagag ctgatagacg cacctgataa atggctgtgg   4080
cacaaaatat gcaagaatga atacagcgt tgtgctgtag ttgaggcata tgacagcatc   4140
aaacatctat tgctctcaat catcaaagtt gacactgaag aacattcgat aattacggtc   4200
ttctttcaga taattaatca gtccattcag tcagagcagt tcaccaagac ctttagagtg   4260
gacctgctgc caaaaattta tgaaacactg cagaaattgg ttgggctggt aaatgatgag   4320
gaaacagata gtgggcgggt ggtgaatgtt ctgcagtctc tttatgagat tgcaactcga   4380
cagttcttta tagagaagaa gacaactgaa cagctatcta atgaaggttt aactcctcga   4440
gacccagcct caaagttgct gtttcaaaat gctattaggc ttcctgatgc aagcaatgaa   4500
gacttctacc ggcaggttag gcgtttacac acgattctca cctctaggga ctctatgcac   4560
agcgtccctg tgaatctaga ggcgagacg cggattgctt tcttcagtaa ttcgctttttc   4620
atgaacatgc ctcatgcccc tcaggtgag aaaatgatgg cgttcagtgt tctgactcca   4680
tattacagtg aggaagttgt atacagcaaa gaacagctcc gaaatgagac tgaggatgag   4740
atttccaccc tatactacct gcagacaatt tatgctgatg aatggaaaaa tttcaaggaa   4800
cggatgcata gggaaggaat caagacagat agtgagttgt ggacaaccaa gctgagagac   4860
ctcaggcttt gggcttccta cagaggtcag acattggcac gtacagttcg tgggatgatg   4920
tactactacc gggctcttaa gatgctcgct tttcttgact ctgcgtctga aatggacatt   4980
cgggagggtg ctcaggagct tggttcagtg aggaatttgc agggagaact gggtggtcaa   5040
tctgatgggt ttgtctctga aaacgaccga tcttccttaa gcagagcaag tagttccgtg   5100
agtacgctgt ataaaggcca tgagtatggg actgcattga tgaaattcac atatgttgtg   5160
gcgtgtcaga tctacgggtc tcaaaaagca aagaaagagc ctcaggcaga ggaaattctg   5220
tatctgatga agcagaacga agctctccgt attgcatatg tggatgaggt gcctgcggga   5280
agaggagaga ctgattatta ctccgttctg gtgaaatacg atcaccagtt ggagaaggaa   5340
gtggaaatat tccgtgtgaa gctacctggt ccagtgaagc tgggcgaggg aaagccagga   5400
aaccagaatc atgcaatgat ctttacccgt ggtgatgctg ttcagaccat tgatatgaac   5460
caagacagtt attttgagga agctctcaag atgagaaatt tgctccagga gtacaaccat   5520
tatcatggta tcagaaaacc aactattctt ggtgtcaggg agcatatctt cacgggatca   5580
gtctcgtcac tggcgtggtt catgtctgct caggagacaa gttttgtcac tcttggtcag   5640
cgtgttcttg caaacccact gaaggtcaga atgcattatg gccaccctga tgtatttgac   5700
agattctggt tcttgagtcg aggcggcatc agtaaggctt ccagagttat aaatatcagt   5760
gaggacatct ttgccgggtt taactgcacg ttaagggggg gaaacgtcac ccaccacgag   5820
tacattcagg ttgggaaggg tccacaattt ggattatttc taactaacta tactgctaca   5880
acgtttttttt aacgttttta acgtttatta attatgcaat ctacttttgt tataattatg   5940
taatttaacg ttttttaatc ttctaaattc aaaaaaattg agtaacctt gtctttatgc   6000
attttttcagg tcgggaaggg acgggatgtt ggattgaatc agatatcaat gtttgaggct   6060
aaggtagcca gtgggaacgg agagcaggtt ctcagccgag atgtgtaccg gctcgggcac   6120
aggcttgatt tcttcagaat gttatcattt ttctacacaa ctgtagggtt tttcttcaac   6180
acaatgatgg tcattcttac tgtttacgct ttcctctggg gacgggttta tctggctctc   6240
agcggggttg agaagtccgc tctagcgac agtacggaca ccaacgccgc gcttggggtg   6300
atcctgaacc agcagttcat cattcagctc ggtctgttca ctgccctgcc aatgattgtt   6360
gaatggtctc tcgaggaggg tttccttcta gcgatatgga atttcattcg aatgcagatt   6420
cagctttcag ctgtcttcta cacattctca atggggacca gagctcacta tttcggtcga   6480
actattctcc atggtggggc caagtataga gccactggac gtggatttgt tgtcgagcac   6540
aagggattca ctgagaacta ccgactgtat gcacgcagtc actttgtgaa ggccatcgag   6600
cttgggctga tcctcatagt ctacgcttcg cacagtccga ttgccaaaga ctcgttgatt   6660
tacatagcca tgactatcac cagctggttt cttgtgattt catggataat ggcccccattt   6720
gtgtttaacc catcaggatt cgactggctt aagacagtct atgactttga agacttcatg   6780
aactggatct ggtaccaagg cagaatctca acgaaatctg aacaaagctg ggaaaaatgg   6840
tggtacgagg aacaggacca cctgagaaac accgggaagg caggattatt tgtggagatc   6900
atcttggtcc tccggttttt cttcttccag tatgggattg tataccagct taaaattgca   6960
aacgatccca ccagccttttt tgtctacttg ttctcatgga tatacatctt tgctatattt   7020
gtgctcttcc tagtcatcca atacgcccgt gacaagtact cggcaaaagc tcacatacgg   7080
```

-continued

```
tacaggcttg tccaattcct cctgatcgtg cttgctatac tggtgattgt tgctttgctc   7140
gagttcacgc atttcagctt catcgatatc ttcacaagcc ttcttgcatt catcccaact   7200
ggctggggaa ttctgctgat cgcacagact caaaggaagt ggctgaagaa ttacactatt   7260
ttctggaatg ctgttgtctc tgttgctcgc atgtatgaca tattgtttgg gatactcata   7320
atggttccag tagcgttctt gtcatggatg cctggattcc agtcaatgca aacgaggata   7380
ttattcaatg aagctttag cagaggactt cgcatcatgc agattgtcac tgggaagaaa   7440
tcaaaaggcg atgtctaagt ttaaaaaacg gtaaagctcc ttgttctcaa caccttatgt   7500
tatgatcgtt taaatcctgg atttcacacc aatgcgggct ttaaatttgt gtaggtctta   7560
agaagtaaat ggtagttcaa atcctattgg tatgtggcga aggaatcagt tggaggttag   7620
ttttcccgaa acaaccgaat tcgaagtttt gtttcgtcta aagaaaaact cagatgctga   7680
tgatttatct ttgtatttta aacaggtttt tggagagttt ggttggatga ggaatcggga   7740
agttggtttg attcggttag atgggtttag ggagatattt gattgtcagt gtgtgtggag   7800
ggaactctga ttcttgtatg gttttgttc taaaggtaca gcaatttgtg tagtgaggct   7860
ttgtgtattt gttctccttc tctcattata gagctttaga gcattttag tttatattca   7920
gattgttatc taatgtcatc tcgcagagct tttgttcaca tttcacatct tttcttctcc   7980
ttcttagtag agatcagttt cagattagat acttgtccat attccactac tctcgtctat   8040
tatcggtttc tgcttgtcaa tttctgggtc caaaattgaa ata                     8083
```

```
SEQ ID NO: 2              moltype = DNA  length = 10394
FEATURE                   Location/Qualifiers
source                    1..10394
                          mol_type = genomic DNA
                          organism = Brassica napus
SEQUENCE: 2
cttccttctt tgccgtctct cttgaagcta agtacaccga tatggccgcc tttaagtatg   60
ttaaatgcaa acacaaatcg attatgttca tctcataagt tatgtgaata tttttagcta   120
gtaattgggt ataacatgtt ttgtaggtat tttgtgatcg caaacgctgt cgtgagtgtt   180
tacagctttc tagttctgtt tcttcctaag gagagtttac tgtggaagtt cgtcgtcgtc   240
ttggatttgg taataattgt tatttggttt agtacttctc ttcgttcatt aattcatttg   300
cattctatct ctaagcatag tttttttcta aaggtaatat tatgttgat atctagtagt   360
ttgatgtgtt cagaggaata aaagcatttt tattggtgaa atactgaaaa ataataaaat   420
gttgattatt atagttcaaa taaacaattg ttttctagaa gaacataaag taatcacaat   480
attatatttt gcatgagagt ttttcacga aattctcata tttcctctta ttatcattta   540
tcgttgagat actttctaag aactctttaa tggagatgt ctagtaaatt aatctttgaa   600
cgaaaagtta aaacatacac tttcaaaaaa aaaaagttaa aacaaataaa cttgaatgta   660
atgtgtctta gtcacacgct tattataggt tgttaggtga cgactatatc agcatacata   720
cgaattgtca ttaacttttg acattttgg tgaatgtatt ggaggtgatg acaatgctac   780
taacgtcaag catatcagcg gcgttagcgg tggcgcaagt gggaaagaaa ggaaacgcaa   840
acgcaggttg gcttccaatt tgcggccaag ttccaaagtt ttgcgatcag gtcaccggag   900
ctctcattgc cggcttcgtc gcactcgtcc tctacgtctt gttactctta tactctcttc   960
actccgtcgt cgatcctttt cttctccaga aatcttgaat ctaacttctt tttcacttt   1020
cagtatcggt taatatacgt tttaatatct atactataac gtcgtttgtg tattgtattt   1080
atatgttttc tgtttttaggt gtcgagattg tcatagtatt tcatttttat ggactaatta   1140
acattataga ctgaaccacc tctcataaac tcttactcat aattaaaaaa aaaaatcaat   1200
gcttcatata tacatctctg tcaatcattg gattcgtatt tattatagta tcaacaaatt   1260
tgtgatacaa acctaaacat gtgcaatatc tttagctaac gaaatggata tagatacatc   1320
ttccctagct atggaaatga gtatttgatc aaaacgtaat tgcacttgtt agttagtcat   1380
ttctctcagt gtaacaaaac accatttatg aaaaaacact gagcatgggc aagtttcgtc   1440
ttcacctccg ttaatctttt gcatcgtaaa aacaatcgat gttacaaaac atgtttttgtt   1500
ttaacgttgt aaaaatatca ggcttgattt gaatgtcatg ttatgccgac tttactagtt   1560
tgtgtaacca actaagctat taaaatatgc gtaattacaa aactgtcaga tttagtttca   1620
caaaatcttt gtaacttcgc ggttttttgat atggaagttg ctacaaaaac tgacttgtga   1680
tattataatc tttcggcaag aaaaaatatat aatactaatt tcagaaagta ttctgttgaa   1740
ttgttgatca ccaaatacac ataaaccggc agatgttgac atgtttacgt gggatcactg   1800
ggataagagt tttgcttctg tattagtatc gcgaaccggt ttgtagtagc gaaaataaca   1860
ttattatttt cagatttcat catcgtcaaa ttcaacgtta catttgaaca ggcttgtaaa   1920
aagtggacat gtggcatgag taaaagataa agaaaattgt gagccttttt gttaatacga   1980
aaaagccgaa aacgttatta tttctatcat cggcaaattt aatgttaaat ttgctccaca   2040
tcattcagag ggtatatgta tattttttcta atgcttcggt gaagcacatg cgaccatttg   2100
ttgcgtcaga agtcagaaca aaaggaagat tccatctaat ggattataat cccacatgcc   2160
cattttaaa actagacaaa ataacttata atagtcccat aagagcatta agacaaactg   2220
aaccaaaaag aatcttaaat gctggtgaat ctagtctcga atgctgctga acactcctga   2280
tattagaatt tggcagaaaa tattcatact aataacagta aatacatttc aaaacaagaa   2340
aatagtagta gtaaataaaa acaattaata tgttattatt gtttctctta gctgttacca   2400
ttacattaac aatttacatt caatccttt aatgaaaat attataaaat attaaaagaa   2460
gttattagaa aaggagaggg atatggggggg ggggggggga gagcatggag gggtcccatg   2520
tgtgtttcga aaagcagcaa acatgacttt gtaaagtctt gttttagcta gagttccaaa   2580
aaaaaaagag ttcaaaaaaa aagaaaaaaa aaagtcttgt tttagcgtcc aaagcggtct   2640
cactcgccgt tcagctgtta aattttcttg aaataaatcg ctccacttgt tttttattt   2700
tgtttctttc aacccacttg tattaataac aataatgata ttgctaatct tgaacaaatc   2760
gtggattgtc ttttcttcca gtgatatcat ccttagtcaa aacatctcaa attaaataaa   2820
tatatagttg tgaattaaaa aaaaaggtat agagtttata aaattagcat ttgcgaatgt   2880
ttttaaaagt ttggcgtttg tatagatcac tgtcagtgtc atgaatcatt cggtgacagc   2940
aaatttgtat atgccaaaaa agagagttga tacttgccat tctcgatatt ttgaattttt   3000
tttcgtcgac atacaaactc aacatttcg aaatcttaga ttaaaaacaa aatggacaaa   3060
acgatactta ttaatgaatt atgtactagc gtctaaacat tagtaacata gatataatta   3120
taagaacaag aaacatatat gcacaaagcc tcaaaccaaa tttaaatagt gttacgaaac   3180
aagggatgta cttgttatga aaaattaatg tataaccatt cttagcattt tttacctaac   3240
ccttaaactt tataaagaaa aatatgtaac atttcggtgt gtggtatata aaagtatttt   3300
```

```
gaaaatcgat ttgattattt ctattattaa aatgtactta cttttttttat cacacattta   3360
tttacaattt cagagttaaa catgattaag acaaagtagt gaaaatatag atgatctacc   3420
agaaaatcat ttgctttctg agtgagatca aaataaaggc aaaaataatg tgatgattgt   3480
atattaaaca attattttga atttgaaaag aataactcat cgaatgaagc ctatgaaccg   3540
agtaagcggt gaagcggttg gaccgtcaca aaaattatga ccaacaagaa aataaaattg   3600
atattagtga atgatatatt ttggaaagta ataaattggt tccagatttc aatacatcaa   3660
tgttttttcta atgctgactt gcttttcctc tttttcttac atgataagga aacgagagag   3720
gtcgaagaaa caaagaaact tcctaagcat ttagcaacgc atcttcaaaa aatctagtat   3780
ttaccaagta aaatcataca aaataaggaa aaaaagaaga atatatttcc caatttggtt   3840
ttcacccgaa aaaaaaactg tcttaacaaa atcttaatgc accaaatcat ataagaactt   3900
tatttgacca ttgtcattag tttttttcctt atggtaatgg atcttcaaat aattttaaatt   3960
aaattaaaaa aaaaagaaaa gagaaacaaa aacgcggaaa ggagagccca aatcgtctcc   4020
gtctgtcatt gtcgcagtct ctaaaagaga aaaacaaatc gcaacgcttc tctctctctc   4080
cctatcgttt gaatcagtct ctcaagatcc accaccacca cacatgctac tatgagcctc   4140
cgccaccgca ccgtcccctc tcaacccgga cggcccccgg cggcgggcgc aatcgaggac   4200
gagccctaca acatcatccc cgtcaacaac ctcctcgccg accacccctc cctccgctac   4260
cccgaggtcc gcgccgccgc cgccgccctc aaaaccgtcg gcgacctccg ccgccccacc   4320
tacgtccaat ggcgccccca ctacgacctc ctcgactggc tcgccctctt cttcggcttc   4380
cagaaggaca acgtccgcaa ccagcgcgag cacctcgtcc tccacctcgc caacgcccag   4440
atgcgcctca ccccgcgcc ggacaacatc gattccctcg atcccgccgt cgtccgccgc   4500
ttccgccgca agctcctcgg taactactcc agctggtgct cctacctcgg gaggaagtcc   4560
aacatctgga tctcggatcg gagcccccgat tcgcggcggg agcttctcta cgtcggcctc   4620
tacctcctcg tctggggcga ggcggccaat cttaggttta tgcctgagtg tatctgttac   4680
atcttccaca atatggcctc ggagcttaac aagatcttag aggattgcct cgacgagagc   4740
acggggcagc cgtattctcc taagatcacg ggggagaata gtttcctaaa cggcgtcgtt   4800
aagcctatct acgacacgat caagagctgag attaatgaga gcaagaaccgg gacggagccg   4860
cattgtaagt ggaggaacta cgatgatatt aatgagtact tctggacgga taggtgtttt   4920
agtaaattga aatggccgat tgatttgggg agcagtttct tcaagaacag cagaggtagc   4980
ggagttggga agacaggttt tgtggagagg aggacgtttt tctacctcta caggagcttt   5040
gataggcttt gggtgatgct tgctttgttt cttcaagctg ctattatagt tgcttgggag   5100
gagaagccgg gtggagggtc ggtgacgagt cagctctgga atgcgttgaa gtcgacggat   5160
gttcaggtga ggcttttgac tgtgttcttg acgtggagtg ggatgaggtt gttgcaggct   5220
gtgttggacg ctggctcgca acggtctctt atttctagag agaccaaacg gctgttttc    5280
agaatgttga tgaaggttgt ggctgctacg gtttggatag tagcgtttat tgttctctac   5340
acgaacatct ggaagcagag gaagcaagat aggcagtggt ccagagccgc gaatgataag   5400
atctatcagt tcctttacgc tgtggtggct ttcttggttc ctgagatcct ggctttggct   5460
ctgtttatg tcccgtggat aaggaacttt ctggaagaga cgaattggaa gatattcttt   5520
gctttgactt ggtggttcca ggggaaaagc tttgtgggtc gaggtttgag agaggggttg   5580
gtggacaaca tcaagtactc gacttctgg atcttttgtcc ttgcaacgaa gttcacgttc   5640
agctacttcc tgcaggttaa gccaatgatt aaaccctcga agctgctatg gaatttgaag   5700
gaggtggatt atgagtggca tcagttcttt ggcgagagca ataggttttc tgtcttgtta   5760
ttgtggctgc cagtggtgtt gatatacctg atggatatcc aaatttggta cgcgatctat   5820
tcttcgattg ttggtgctgt tgttgggctg tttgatcatc tgggggagat caggggacatg   5880
ggacagctta ggctgaggtt tcagttcttt gctagcgcta ttcagttcaa cctaatgcct   5940
gaggaacaac tcctgaatgc tagaggattt ggtaacaagc ttaaggacgc cattcatagg   6000
taagtctatt gaagcatgtt actgatattt ctatataatt tactatatag agtttgtctt   6060
taaagtacaa gctatagtat tttagttttg ttaaagcaga ttctccgcaa tgaactcgac   6120
tttttcacat tgtaataaca ttgagtttgt gtacttatg cagattgaag ctgaggtatg    6180
gattggggcg gccgtttaag aaaactcgagt ccaatcaggt tgaggctaac aagtttgcgc   6240
tgatctggaa tgagataatc ttagctttca gagaggagga tatagtctct gatcgagaag   6300
tagagctgct ggagctgcca aagaattcct ggaatgtgac agttatccgc tggccgtgtt   6360
tcctgttgtg caacgaactt ttgcttgcac tgagccaggc gaaagagctg gttgacgcac   6420
ctgataaatg gctgtggcac aagatatgca agaatgagta caggcggtgt gctgtggttg   6480
aggcatatga aagcatcaaa catctgttgc tctcaatcat caaaattgac actgaagaac   6540
ataaaattgt tacaattttc tttcagatga ttgaggtgtc tattcaggt gagcagttca    6600
ccaagacctt caaagtggac cttttgccaa agatttatga gacactgcag aagttggttg   6660
ggctgttgaa tgatgagaaa gtggatgttg ggcgagtggt gaatggtctg cagtctattt   6720
atgagattgc aacacgacag ttcttcctag aaaagaagac gactaacag ctatctactg    6780
aggggttaac tcctcatgat ccagcctcaa agttactgtt tcagaatgct gttaggcttc   6840
ccgatgcaag caatgaagac ttcttccggc aggttaggcg gttacacaca attctcactt   6900
ctagggactc tatgcacagc gtccctgtga atctcagaggc gagacggcgg attgccttct   6960
tcagcaattc gctcttcatg aacttgcctc atgcacctca ggtggagaaa atgttggcgt   7020
tcagtgttat gactccatac tacagcgagg aagttgtata cagcaaagaa cagctccgaa   7080
atgagactga ggatgggatt tcaaccttgt attacctgca gacgatttat gccgacgaat   7140
ggaaaaattt taaggaacgg atgcgtaggg aaggtataaa gacagatgtt gagttgtgga   7200
caaccaagct gagagagctc aggcttgggg cttcctacag aggtcagact ttggcacgta   7260
caattcgagg aatgatgtac tattacaggg ctcttaagat gcttgctttt cttgactctg   7320
cgtctgaaat ggacattcgg gaggatgctc aggagcttg ttcaatgagg agttcgcagg     7380
gaaatcgatt ggatggggtg gacgatgtaa atgacgaata ttctctaagc agagcaacta   7440
gctctgtgag catgctgtat aaaggccatg agcatgggac tgcattgatg aaattcacat   7500
atgtcgtggc gtgccagatc tatgggtctc aaaaagcgaa gaaggagcct caggcagagg   7560
aaattctgta tcttatgaag caaaacgaag ccctccgtat tgcatatgtg gatgaggtgc   7620
atgcgggcag ggaagagact gagtattact ccgttctggt gaaatacgat cacacgttgg   7680
agaaggaagt ggagatattc cgtgtgaagc tacctggtcc ggtgaagctg ggtgagggaa   7740
agccagagaa ccagaatcat gcaatgatct ttacccgcgg tgatgctgtt cagaccatag   7800
atatgaacca ggataattat tttgaggagg ctctcaaaat gagaaattta ctccaggagt   7860
ttaggcatta tcatgggatc agaaaaccaa ctattcttgg tgtcagagag cacatcttca   7920
cgggttctgt ctcgtctctg gcttggttca tgtctgctca ggaaacaagt ttcgtcactc   7980
tgggtcagcg tgttctagcc aacccgctga aggtcagaat gcattatggt caccctgatg   8040
```

-continued

```
tatttgacag attctggttc ttgagtcgag gtggcatcag caaagcttct agagttataa    8100
atatcagtga ggacatcttc gccgggttta attgcacatt gcggggcggt aacgtcaccc    8160
accacgagta tattcaggta gggaaatgtt catcatttgg atattctaac taattttata    8220
catcgacaac aatactataa ttccactttt tttgttataa cctttttgtg tgtgcatatg    8280
tattcaggtt gggaagggtc gagatgttgg attgaatcaa atatcaatgt ttgaggctaa    8340
ggtagccagt gggaatggag agcaggttct tagccgagat gtgtacaggt tgggtcatag    8400
gctcgatttc ttcagaatgt tatcattttt ctacacaacg gtgggggttt tcttcaacac    8460
gatgatggtc attctcactg tctacgcttt cctctggggc cgggtttatc ttgctctgag    8520
cggtgttgag aagtccgctc tagcagacag cacagacacc aacgcagcgc ttgctgtgat    8580
attgaaccag caattcatca ttcagcttgg tctcttcaca gctctgccaa tgattgtgga    8640
atggtctctc gaggagggtt tccttctcgc gatatggaac ttcattcgga tgcagattca    8700
gctttcctct gtcttctaca cattctcaat ggggaccaga gctcactatt ttggccgaac    8760
cattctccat ggtggagcaa agtacagagc cactgggcgt ggatttgttg tcgagcacaa    8820
gagcttcact gagaattacc gtctatacgc acgcagtcac tttgtgaagg ccatcgagct    8880
tgggctgatc ctcatagtct acgctacgca cagtcccatc gccaaagact cattgatcta    8940
tatagctatg actctcacca gctggttcct cgtgtatca tggatactgg ccccttttgt    9000
gttcaacccg tcaggattcg actggcttaa gacggtctac gacttcgaag gcttcatgaa    9060
ctggatctgg tatcaaggca ggatctcaac gaagtccgaa cagagctggg agatatggtg    9120
gtatgaggaa caggaccacc tgagaaccac cggtatacca ggaagaatcg tggagataat    9180
cttggacctt cggttttct tcttccagta cgggattgta taccagctca aaatcgcaaa    9240
cggatcaacc agcattctcg tctacttact ctcatggata tacatcttcg cagtgtttgt    9300
gttcttccta gtaatccaat acgcccgtga caagtactct gcgagaaacc acatacggta    9360
caggctcgtt cagttcctcc tgatcgtgtt tggtacactg gtgattgttg ctctcctcga    9420
gttcacgcat ttcagcttcg tggatatctt cacgagtctt cttgcgttcg tcccaaccgg    9480
ctgggggatc ttgctgatcg cacaggcgtt gaggcctgcg ctgcagaaga tcgggcttat    9540
ctggaacgcg gttatctccc ttgctcggtt atatgacata ctgttcggga tagtcatcat    9600
ggttcccgta gcgttcatgt cgtggatgcc tgggtttcag tcgatgcaaa cgaggatctt    9660
attcaatgaa gcttttagca gagggcttcg tatcatgcag attgtcactg ggaagaaatc    9720
aaaaggcgat gtcgaagttg aaaaaagaag gtaaagcttc ttatttaccc aaacatcttt    9780
ttatgttctg tttgtttgga atcttaaatt acaacaacac taatgcaaag cttttacaac    9840
ttgtgtaggt cttgaggtat atggtaattt aaaagttgct ggtttgcggc gatgtgacct    9900
gttggaggtt agttttgtat tcttacaagt tatgcttctt gtctgaatag gaactcgac    9960
acccgtgttt tgtcttcttc ttattaaacc aggttttgg agagctttgg ttgaggaagc   10020
tattcgatta gataaatctt ttagtggggg agacatatat atatacattt gtcagtactt   10080
tgttagtgtg tggaagtggg gacgactctg attctgattc cttatgtggt tattgtctga   10140
aacgttacag cattttgtga agtaggcttt tgtgcaagat ttgatctctt tctctcattg   10200
tagagcttta gagcattttt tagtatatgt ttaatctttg attttctaat gtcatttgca   10260
ttcatattca catcttcttc gttggtctta aaccagtttt cagatgctta tccattgtcc   10320
acttctctat gtatctgttt cttctgtttg ttttcagtat tgtcttttat tctttaatca   10380
gttttatttg gacc                                                    10394
```

```
SEQ ID NO: 3          moltype = DNA  length = 10431
FEATURE               Location/Qualifiers
source                1..10431
                      mol_type = genomic DNA
                      organism = Brassica napus
SEQUENCE: 3
agtgagtttg ttctccagcg agccggagaa ggcatcaacg caaacctgga ggaacagatt      60
gaccggtatg ttcattaacg ctgcaagcca gctttgatgt tagctgcgta aagatccctg     120
cgtttacatc aaaacattac attgtttgct gtgactaagg taacagagta aacgtgtaaa     180
atactctggt gtttttggaga aaacaaactt acatggagcc cttaattgca tctatggcag     240
cttgtgctga gaggaaacct tcaacgtcca ctttttccttg taggttacta atatatgcat     300
attttatttta aatcaatcca aatatatggg taaaaaactt tatttgagga tgtactatat     360
atatgaatgc ctaagagtat aatgtacaaa ggtgaaactt gccttgacat tgaaggagta     420
gaggactgtt tgctccatgg tagtcatgta agtgtgaaga atagagagat gaagatcctc     480
caaaaaagca atagtcttaa taagttgtcc tggtcttctt cttgaaagtt tcttgatcat     540
ggcatcaaac tctagcagct tcacctccac atcagccaag cacgactcgt tctcagctgt     600
ttcttcccgg agccctcctc ctcctcctat acgactcatg tgactctagg cattgtagaa     660
gttgctcaag ctctcttaca aactctattc cacctatgat cgacgcttga tctctctgtt     720
atatacatgc atattaaaaa atattttaaa ataatgaata caatcacgaa atgaagatgt     780
atatgtgtta tcatgatacc cattgaacgt aggatccaga caaaagagac ttgaggttac     840
gaagatgctc gttcatttgc ttcctattcc tagcgaccgc aatatgtctc attcgttagt     900
tttctacttc ttcgcttgtc ttgcttgttt ttgctcttca cctcctttgt catatcattc     960
ttgttctcac tatctccttc ttctcctcca gtaaaccgac ttgttattgt cgttaacgtc    1020
taaggattca cctaaaaaat ttggtgcctg aaagaaaata aaggtgaaga aataattatt    1080
aagataatat aggtcaattg acttggaatc aaaattttca ccctgcaagt tgacatggtt    1140
tcatactaat gtgatacatt aagacatagt ttatggtttt aatgattgtt acctgatcca    1200
tcaggcatta taccaaaagg acaggcacgg aggaactatt cagttagccc atgctcctgc    1260
acaaatttat caatcaactc atatctagaa ggatatatga gaaaagaagt ttctggtgtt    1320
attaggagtt gtgaggatga tgtttattaa gaaataaact atataagcct ttacatataa    1380
attacaaaat accttgattc tcatccaaga ttccggtgtg gatcgattta tcaatgacat    1440
atttgcaaaa aaaaataata gggttacctg gaagatgggt gttggtgttt gctagaccaa    1500
gcaactcatc tttgcagaac ctgaaacgtt cttgaggaat tggtgaacct gggtcagtta    1560
agtcttttcaa acccgtctca atattgaacc ggatcgacac aggagagtcg gacagcttga    1620
agtccggaca gctcaaagcc gctaacagag tacacttaac caacagtgaa aagatgtctg    1680
aatgtgttta agcggtagac gttcacggtg gcttaggtga gagtggcctg caaagcatga    1740
aaaattggaa acataaacaa atgaaataaa tattgcaatc attaaaaata aactaaagcg    1800
cttgttaact ttttcataat caaaagacat aagcatatgg atgtctctac acggactatt    1860
tgaattttag gtatgaataa aatatacgaa aaaagtaaaa aagaatcaac aatcacaaca    1920
```

-continued

```
atgatcatat cccaaatatt tgaagataac aaaaacttat ggagaataac gaagacatga   1980
atgtattgat ctccggtgaa gaactattag gtttgaaagt ttcataacca aaacacaaca   2040
acgcgagaaa ggattaaaaa acaaaacaaa actacatagt caagccggat ttaccttggc   2100
gtccatgaag agaatgttga ccctctctgt cgcgcttaac attcctatct tcccagaacc   2160
taagcaaacg gacctgggcg gtggaggtgc agcggctagc tttcaaatcg gcgagaaaga   2220
cggaggaatt agccattatc gactttgatt tcttagaaaa cagtttatgg gaatgtagta   2280
ggattgtgag aatgatgttt ctgggaagag cacatacctt tttgtaggag gagcttcacc   2340
gcttgtaaga gagatgagag tattgagtga gaaatcgttg agcttcatcg tggaggatgg   2400
atttaaaaag ggctttaaga gtaagaatct gtaacaggta gattgctgga tccgtaggaa   2460
gaagatgaag catctcgatc aaaaccctag ggtatgatat tgcaacggcg gagaagagaa   2520
tgagatgaaa ccatagaatt aaaaactctg cgtttcaggc atacgtctta ctctgctttt   2580
taaagattgg gctttataaa ccaaaacaat aacaaagaat gtagcccaaa cggaaacaga   2640
ataaatgaaa cgcggtaaag tgaacagatg tcacataatg attggctgat ttaattgtcc   2700
tacgtggaca gcttctctga tgctcatata accctttag tataggttag atgatatcat   2760
ccttagtcaa aagtcaaaac atctcaaatt aaataagtaa agagttgtga attttaaaa   2820
aagtatagag tatataaaat tagcatttgc gaatgttttt aaaagtttgg cgtttgtatg   2880
gatcactgtc agtgtcatga atcattcggt gactgcaaaa ttttatatga caaaaaaaaa   2940
agagagttga tacttaccat tctcgatatt ttgaaatttt tttcgtcgtt aatacaaact   3000
caacattttc gaaatcttgg attaaaaaaa aaaaatatgg acaaaacggt acttattaat   3060
taattatgta ctagcgtctt gacattatta atatagatat aattataaga acaagaaacg   3120
tatatgcaca aaccctcaaa ccaaatttaa atagtgttaa aaaacaaggg atgtacttgt   3180
tatgaaaaat taatatataa ccattcttaa catttttaac taaccccttaa actttataaa   3240
taaaaatacg taatatcccg atagaaatat tttaaaattt tgatttgatt atttatgtta   3300
tcaaagtgca tttatttttt tttgtcacgt atatatttaa aatttcaaca ttaaaagtgt   3360
gtaagatgga gtagtgaaaa tatagacgac ttaccataaa attatttgtg atatcatttg   3420
aataagacta aaacacggac aaaaataata tagtgattgc attgttatta aacaattatt   3480
tggatttgaa aagaaataac tcattgaatg aagcctatga gccgagtaaa cggacgtgga   3540
tagcttaagc ggttggaccg tacaaaattt atgaccaaca agaaaatgaa attgattttt   3600
tttttgacga aaaaatgaaa ttgatttttag aaagtaacaa aatggttcca gatttcaata   3660
cttcaacgtt tttttatgcc gactttcttt tcctctttta cttacatgat aaggaaacga   3720
gagaggttga agaaacaaag aaacttccta agcatttaga aatgtatctt caaaaaatct   3780
agtatttacc aagtaaaatc attcaaaata aggaaaaaaa gaagaatcta tttcccaatt   3840
tggttttcac cgaaaaaaaa attgtcttaa taaaatctta atgcaccaaa tcatataaga   3900
actttatatg accattgtca ttagtttttt ctttatggta atggatcttc aaataattta   3960
aattaaatta aaaaaaaaaa agagaaacaa aaacgcggaa aggagagccc aaatcgtctc   4020
cgtctgtcat tgtcgcagtc tctcacagct aaataaaaga gaaaaacaaa tcgcaacgct   4080
tcaatatctc tctcccaatc gtttgaatca gtcttcctca tcacaatccc ccaaagatcc   4140
accacacatg ctactatgag cctccgccac cgcaccgtcc cctctcaacc cggacggccc   4200
ccggcggcgg gcgcaatcga cgacgagccc tacaacatca tccccgtcaa caacctcctc   4260
gccgaccacc cctccctccg ctaccccgag gtccgcgccg ccgccgccgc cctcaaaacc   4320
gtcggagacc tccgccgccc cacctacgtc caatggcgcc cccactacga cctcctcgac   4380
tggctcgccc tcttcttcgg cttccagaag gacaacgtcc gcaaccagcg cgagcacctc   4440
gtcctccacc tcgccaacgc ccagatgcgc ctcacgccgc cgccggataa catcgattcc   4500
ctcgatcccg ccgtcgtccg ccgtttccgc cgcaagctcc tcggtaacta ctcgagctgg   4560
tgctcgtacc tcgggaggaa gtcgaacatc tggatctcgg atcggaaccc cgattcgagg   4620
cgggagcttc tctacgtcgg cctctacctc ctcgtgtggg gggaggcggc gaatcttagg   4680
tttatgccga agtgtgtctg ttacatcttc cacaatatgg cctcggagct taacaagatc   4740
ctcgaggatt gcctcgacga gagcacgggg cagccgtact ctcctagaat cacgggggag   4800
aatagtttcc taaacggcgt cgttaaacct atttacgaga cgatcaaagc tgagattaac   4860
gagagcaaga acgggacgga gccgcattgt aagtggagga actatgatga tattaatgaa   4920
tactttggga cggataggtg ttttagtaaa ttgaaatggc cgattgattt ggggagcagt   4980
ttcttcaaga gtagtagagg gagaggcgtt gggaagacag gttttgtgga gaggaggacg   5040
ttctttttacc tctacaggag ctttgatagg ctttgggtga tgcttgcttt gtttcttcaa   5100
gctgctatta tagtcgcttg ggaggagaag ccgggtggag ggtcggtgag gagtcagctc   5160
tggaatgcgt tgaagtcgag ggatgttcgg gtgaggcttt tgactgtgtt cttgacgtgg   5220
agtgggatga gattactgca ggctgtgctg gacgctgcct cgcaacggcc gcttatttct   5280
agagagacca agcggctgtt tttcagaatg ttgatgaagg ttgtagctgc tacggtttgg   5340
ataattgctt ttattgttct ctacacgaac atctggaagc agaggaagca agacaggcag   5400
tggtccagag ccgcgaatga caagatctat cagttccttt acgctgtggt ggctttcttg   5460
gtccctgaga tcctggcttt ggctctgttt atagtcccgt ggataaggaa ctttctggaa   5520
gagaccaatt ggaagatatt ctttgctttg acttggtggt tccagggtaa aagctttgtg   5580
ggtcgaggtt tgagagaggg gttggtggac aacatcaagt actcgacttt ctggatcttt   5640
gtcctagcaa cgaagttcac gttcagctac ttccttcagg ttaagccaat gattaaaccc   5700
tcgaagctgc tatggaattt gaaggaggtg gattatgaat ggcatcagtt ctttggcaag   5760
agcaataggt tttctgtctt gttattgtgg ctgccagtgg tgttgatata cctgatggat   5820
atccaaattt ggtacgcgat ctattcttcg attgttggtg ctgttgttgg gctgtttgat   5880
catctggggg agatcaggga catggacag cttaggctga ggtttcagtt ctttgctagc   5940
gctattcagt tcaacctaat gcctgaggaa caactcctga atgctagagg atttggtaac   6000
aagcttaagg acgccattca taggtaagtc tattgaagca tgttactgat attcctttat   6060
aatttactgt acagagtttg tctttacggt acaagttatg gaattttagt tttgttaaag   6120
cagattctct taactcggct tttcaacatt gtaataacct tgagtttgtg tactttatgc   6180
agattgaagc tgaggtatgg acttgggcgg ccatttaaga aactcgagtc taatcaggtt   6240
gaggctaaca agtttgcgct gatctggaat gagataatct tagctttcag agaagaggat   6300
atagtctctg atcgagaagt agagctactg gagctgccaa aaaattcctg gaatgtgaca   6360
gttatccgct ggccgtgttt cctgttgtgc aacgagcttt tgcttgcact gagccaggcg   6420
aaaagagctg ttgacgcacc tgataaatgg ctgtggcaca agatatgcaa gaacgagtac   6480
aggcggtgtg ctgtggttga ggcatatgaa agcatcaaac atctgttgct ctcaatcatc   6540
aaaattgaca ccgaagaaca taaaattatt acaattttct ttcagatgat tgaggtgtct   6600
attcagggtg agcagttcac caagaccttc aaagtggacc tattgccaaa gatttatgag   6660
```

-continued

```
acgctacaga agttggttgg gctgttgaat gatgagaaag tggatgttgg gcgagtggtg    6720
aatggtctgc agtctattta tgagattgca acacgacagt tcttcataga aaagaagacg    6780
actgaacagc tatctaccga gggggttaact cctcatgatc cagcctcaaa gttactgttt    6840
cagaatgctg ttaggcttcc cgatgcaagc aatgaagact tcttccggca ggttaggcgg    6900
ttacacacaa ttctcacttc tagggactct atgcacagcg tccctgtgaa tctagaggcg    6960
agacggcgga ttgccttctt cagcaattcg ctcttcatga acttgcctca tgcacctcag    7020
gtggagaaaa tgttggcgtt cagtgttatg actccatact acagcgagga agttgtatac    7080
agtaaagaac agctccgaaa tgagactgag gatgggattt caaccttgta ttacctgcag    7140
acgatttatg ccgacgaatg gaaaaatttt aaggaacgga tgcgtaggga aggtataaag    7200
acagatgttg agttgtggac aaccaagctg agagagctca ggctttgggc ttcctacaga    7260
ggtcagactt tggcacgtac agttcgagga atgatgtact attacagggc tcttaagatg    7320
cttgctttttc tcgactctgc gtctgaaatg gacattcggg aggatgctca ggagcttggt    7380
tcaatgagga gttcgcaggg aaatcgattg gatggtgttg acgatgtaaa tgaccgatct    7440
tctctaagca gagcaactag ctctgtgagc atgctgtata aaggccatga gcatgggact    7500
gcattgatga aattcacata tgtcgtggcg tgccaaatct atgggtctca aaaagcgaag    7560
aaaagagcctc aggcagagga aattctgtat cttatgaagc aaaacgaagc ccttcgtatt    7620
gcatatgtgg atgaggtaca tgcgggcagg ggagagactg agtattactc cgttctggtg    7680
aaatacgatc acacgttgga gagggaagtg gagatattcc gtgtgaagct acctggtccg    7740
gtgaagctgg gtgagggaaa gccagagaac cagaatcatg caatgatctt tacccgtggt    7800
gatgctgttc agaccataga tatgaaccag gataattatt ttgaggaggc tctcaagatg    7860
agaaatttgc tccaggagtt taggcattat catgggatca gaaaaccaac tattcttggt    7920
gtcagagagc acatcttcac gggttctgtc tcgtctctgg cttggttcat gtctgctcag    7980
gagacaagtt tcgtcactct tggtcagcgt gttctagcca acccgctgaa ggtcagaatg    8040
cattatggtc accctgatgt atttgacaga ttctggttct tgagtcgagg tggcatcagc    8100
aaaagcttcta gagttataaa tatcagtgag gacatcttcg ccgggtttaa ttgcacattg    8160
cggggcggta acgtcaccca ccacgagtat attcaggtag ggaaatgttc atcgtttgga    8220
tattctaact aatttataca tcgacaacaa tactataatt ccactttttt gttataacct    8280
ttttgtgtgt gcatatgtat tcaggttggg aagggtcgag atgttggatt gaatcaaata    8340
tcaatgtttg aggctaaggt agccagtggg aatggagagc aggttcttag ccgagatgtg    8400
tacaggttgg gtcataggct cgatttcttc agaatgttat cattttttct cacaacggtg    8460
gggtttttct tcaacacgat gatggtcatt ctcactgtct acgctttcct ctggggccgg    8520
gtttatcttg ctctgagcgg tgttgagaag tccgctctag cagacagcac agacaccaac    8580
gcagcgcttg ctgtgatatt gaaccagcag ttcatcattc agcttggtct cttcacagct    8640
ctgccaatga ttgtggaatg gtctctcgag gagggtttcc ttctcgcgat atggaacttc    8700
attcggatgc agattcagct ttcttctgtc ttctacacat tctcaatggg gaccagagct    8760
cactattttg gccgaaccat tctccacggt ggagcaaagt acagagccac tggacgtgga    8820
tttgttgtcg agcacaagag tttcactgaa aactaccgtc tatacgcgcg cagtcacttt    8880
gtgaaggcca tcgagcttgg gctgatcctc atagtctacg ctacgcacag tcccatcgcc    8940
aaagactcat tgatctatat agccatgact ctcaccagct ggttcctcgt gatttcatgg    9000
atactagccc cttttgtgtt caacccgtca ggtttcgact ggcttaagac ggtctacgac    9060
ttcgaaggct tcatgaactg gatctggtat caaggcagaa tctcaacgaa gtccgaacag    9120
agctgggaga tatggtggta tgaggaacag gaccacctga gaaccaccgg tctaccagga    9180
agaatcatgg agataatctt ggaccttcgg ttttttcttct tccagtacgg gattgtatac    9240
cagctcaaaa tcgcaaacgg atcaaccagc attctcgtct acttactctc atggatatac    9300
atcttcgcag tgtttgtgtt cttcctggta atccaatacg cccgtgacaa gtactcagcg    9360
agaaaccaca tacggtacag gctcgttcaa ttcctcctga tcgtgtttgg tacactggtg    9420
attgttgctc tcctggagtt cacgcatttc agcttcgtgg atatcttcac gagtcttctt    9480
gcgttcgtcc caaccggctg gggaatcttg ctgatcgcac aggctttgag gcctgcgctg    9540
cagaagatcg ggcttatctg gaacgcggtt atctcccttg ctcggttata tgacatactg    9600
ttcgggatag tcatcatggt ccccgtagcg ttcatgtcgt ggatgcctgg gtttcagtcg    9660
atgcaaacga ggatcttatt caatgaagct tttagcagag ggcttcgtat catgcagatt    9720
gtcactggga agaaatctaa aggcgatgtc gaagttgaaa aaagaaggta aagctttttat    9780
aacttgtgtt ctgtttatgt ttgtttggaa tcttaaatta caacaacacc aatgcaaagc    9840
ttttataact tgtttaggtc ttaaggtata tggtaactta aaagtcgttg gttttgcggc    9900
gatgtgatca gttggaggtt agttttctca agacatggaa gtttataag ttattgcttc    9960
ttgtgtgaag aagaagtcat atacatccat gttttgtttt gtcttcttct taaagcaggt   10020
ttttggagag ctttggttga ggaatccgga agttagataa tctttttagtg ggggagacat   10080
atatatacac atttgtcagt actttgttag agtgtgtgga agtggggacg actctgattc   10140
tggttcctta tgtggttatt gtctgaaacg ttacagcatt ttgtgaagta ggcttttgtg   10200
caagatttga tctctttctc tcattgtaga gctttagagc attttttagt atatgtttaa   10260
tctttttgatt ttctaatgtc atttgcattc atatttcaca tcttcttcgt tggtcttaaa   10320
ccagtttttca gatgcttatc cattgtccac ttttctatgt atctgtttct tctgtttgtt   10380
ttcagtattg tcttttattc tttaatcagt tttatttgga ccacaacacc a             10431
```

```
SEQ ID NO: 4         moltype = DNA  length = 9344
FEATURE              Location/Qualifiers
source               1..9344
                     mol_type = genomic DNA
                     organism = Brassica rapa
SEQUENCE: 4
aaagtaataa aatggttcca aatttcaata catcaatggt tttctaatgc tgacttgctt     60
ttcctctttt acttaaacga taaggaaacg agagaggttg aagaaacaaa gaaacttcct    120
aagcatttac aaatatatct tcaaaaaatc tagtatttac caagtaaaat catacaaaat    180
aagaaaaaaa aagaagaatc tatttcccaa tttggtttttc accggaaaaa aaaaactgtc    240
ttaacaaaat cttaatgcac caaatcatat aagaacttta tttgaccatt gtcattagtt    300
tttttcctta tggtaatgga tcttcaaata atttaaatta aattaaaaaa aaagaaaaaa    360
gaaacaaaaa cgcggaaagg agagcccaaa tcgtctccgt ctgtcattgt cgcagtctct    420
aaaagagaaa aacaaatcgc aacgcttcaa tatctctctc tctctcccta tcgtttgaat    480
cagtctccca agatccacca ccacacatgc tactatgagc ctccgccacc gcaccgtccc    540
```

```
ctcacaaccc ggacggcccc cggcggcggg cgcaatcgac gaggagccct acaacatcat   600
ccccgtcaac aacctcctcg ccgaccaccc ctccctccgc taccccgagg tccgcgccgc   660
cgccgccgcc ctcaaaaccg tcggcgacct ccgccgcccc acctacgtcc aatggcgccc   720
ccactacgac ctcctcgact ggctcgccct cttcttcggc ttccagaagg acaacgtccg   780
caaccagcgc gagcacctcg tcctccacct cgccaacgac cagatgcgcc tctccccgcg   840
gccggacaac atcgattccc tcgatcccgc cgtcgtccgc cgcttccgcc gcaagctcct   900
cggtaactac tccagctggt gctcctacct cgggaggaag tccaacatct ggatctcgga   960
tcggacccc gattcgcggc gggagcttct ctacgtcggc ctctacctcc tcgtgtgggg  1020
cgaggcggcg aatcttaggt ttatgcctga gtgtatctgt tacatcttcc acaatatggc  1080
ctcggagctt aacaagatct tagaggattg cctcgacgag agcacggggc agccgtattc  1140
tcctaagatc acgggggaga atagtttcct aaacggcgtc gttaagtcag aacaaaagga  1200
agattccatc taatggatta taatcccaca tgcccatttt taaaactaga caaaataact  1260
tataatagtc ccataagagc attaagacaa actgaaccaa aaagaatctt aaatgctggt  1320
gaatctagtc tcgaatgctg ctgaacactc ctgatattag aatttggcag aaaatattca  1380
tactaataac agtaaataca tttcaaaaca agaaaatagt agtagtaaat aaaaacaatt  1440
aatatgttat tattgtttct cttagctgtt accattacat taacaattta cattcaatcc  1500
ttttaatgaa aaatattata aaatattaaa agaagtatt agaaaaggag agggatatgg  1560
ggggggggag agcatggagg ggtcccatgt gtgtttcgaa aagcagcaaa catgactttg  1620
taaagtcttg ttttagctag agttccaaaa aaaaaagagt tcaaaaaaaa agaaaaaaaa  1680
aagtcttgtt ttagcgtcca aagcggtctc actcgccgtt cagctgttaa attttcttga  1740
aataaatcgc tccacttgtt ttttattttt gtttctttca acccacttgt attaataaca  1800
ataatgatat tgctaatctt gaacaaatcg tggattgtct tttcttccag tgatatcatc  1860
cttagtcaaa acatctcaaa ttaaataaat atatagttgt gaattaaaaa aaaaggtata  1920
gagtttataa aattagcatt tgcgaatgtt tttaaaagtt tggcgtttgt atagatcact  1980
gtcagtgtca tgaatcattc ggtgacagca aatttgtata tgccaaaaaa gagagttgat  2040
acttgccatt ctcgatattt tgaatttttt ttcgtcgaca tacaaactca acattttcga  2100
aatcttagat taaaaacaaa atggacaaaa cgatacttat taatgaatta tgtactagcg  2160
tctaaacatt agtaacatag atataattat aagaacaaga aacatatatg cacaaagcct  2220
caaaccaaat ttaaatagtg ttacgaaaca agggatgtac ttgttatgaa aaattaatgt  2280
ataaccattc ttagcatttt ttacctaacc cttaaacttt ataaagaaaa atatgtaaca  2340
tttcggtgtg tggtatataa aagtattttg aaaatcgatt tgattatttc tattattaaa  2400
atgtacttac ttttttttatc acacatttat ttacaatttc agagttaaac atgattaaga  2460
caaagtagtg aaaatataga tgatctacca gaaaatcatt tgctttctga gtgagatcaa  2520
aataaaggca aaaataatgt gatgattgta tattaaacaa ttattttgaa tttgaaaaga  2580
ataactcatc gaatgaagcc tatgaaccga gtaagcggtg aagcggttgg accgtcacaa  2640
aaattatgac caacaagaaa ataaaattga tattagtgaa tgatatattt tggaaagtaa  2700
taaattggtt ccagatttca atacatcaat gtttttctaa tgctgacttg cttttcctct  2760
ttttcttaca tgataaggaa acgagagagg tcgaagaaac aaagaaactt cctaagcatt  2820
tagcaacgca tcttcaaaaa atctagtatt taccaagtaa aatcatacaa aataaggaaa  2880
aaaagaagaa tatatttccc aatttggttt tcaccggaaa aaaaaaactg tcttaacaaa  2940
atcttaatgc accaaatcat ataagaactt tatttgacca ttgtcattag ttttttcctt  3000
atggtaatgg atcttcaaac aatttaaatt aaattaaaaa aaaaaagaaa agagaaacaa  3060
aaacgcggaa aggagagccc aaatcgtctc cgtctgtcat tgtcgcagtc tctaaaagag  3120
aaaaacaaat cgcaacgctt caatatctct ctctctctct ctccctatcg tttgaatcag  3180
tctctcaaga tccaccacca cacatgctac tatgagcctc cgccaccgca ccgtcccctc  3240
tcaacccgga cggccccgg cggcgggcgc aatcgaggac gagccctaca acatcatccc  3300
cgtcaacaac ctcctcgccg accacccctc cctccgcacc tacgtccaat ggcgcccca  3360
cgccgccctc aaaaccgtcg gcgacctccg ccgccccacc tacgtccaat ggcgccccca  3420
ctacgacctc ctcgactggc tcgccctctt cttcggcttc cagaaggaca cgtccgcaa  3480
ccagcgcgag cacctcgtcc tccacctcgc caacgcccag atgcgcctct cccgccgcc  3540
ggacaacatc gattccctcg atcccgcgcc cgtccgccga ttccgccgca agctcctccg  3600
taactactcc agctggtgct cctacctcgg gaggaagtcc aacatctgga tctcggatcg  3660
gacccccgat tcgcggcggg agcttctcta cgtcggcctc tacctcctcg tgtgggggcga  3720
ggcggcgaat cttaggttta tgcctgagtg tatctgttac atcttccaca atatggcctc  3780
ggagcttaac aagatcttag aggattgcct cgacgagagc acggggcagc cgtattctcc  3840
taagatcacg ggggagaata gtttcctaaa cggcgtcgtt aagcctatct acgacacgat  3900
cagagctgag attaatgaga gcaagaacg gacggagccg cattgtaagt ggaggaacta  3960
cgatgatatt aatgagtact tctggacgga taggtgtttt agtaaattga aatggccgat  4020
tgatttgggg agcagtttct tcaagaacag cagaggtagc ggagttggga agacaggttt  4080
tgtggagagg aggacgtttt tctacctcta caggagcttt gatagctttt gggtgatgct  4140
tgctttgttt cttcaagctg ctattatagt tgcttgggag gagaagccgg gtggagggtc  4200
ggtgacgagt cagctctgga atgcgttgaa gtcgacggat gttcaggtga ggcttttgac  4260
tgttttcttg acgtggagtg ggatgaggtt gttgcaggct gtgctggacg ctggctcgca  4320
acggtcgctt atttctagag agaccaaacg gctgtttttc agaatgttga tgaaggttga  4380
ggctgctacg gtttggataa tagcgtttat tgttctctac acgaacatct ggaagcagag  4440
gaagcaagat aggcagtggt ccagagccgc gaatgataag atctatcagt ccttttacgc  4500
tgtggtggct ttcttggtcc ctgagatcct ggctttggct ctgtttatag tcccgtggat  4560
aaggaacttt ctggaagaga ccaattggaa gatattcttt gctttgactt ggtggttcca  4620
ggggaaaagc tttgtgggtc gaggtttgag agaggggttg gtggacaaca tcaagtactc  4680
gactttctgg atctttgtcc tcgcaacgaa gttcacgttc agctacttcc ttcaggttaa  4740
gccaatgatt aaaccctcga agctgctatg gaatttgaag gaggtggatt atgagtggca  4800
tcagttcttt ggcgagagca ataggttttc tgtcttgtta ttgtggctgc cagtggtgtt  4860
gatatacctg atggatatcc aaatttggta cgcgatctat tcttcgattg tcggtgctgt  4920
tgttgggcgt gtttgatcatc tggggggagat cagggacatg ggacagctta ggctgaggtt  4980
ccagttcttt gctagcgcta ttcagttcaa cctaatgcct gaggaacaac tcctgaatgc  5040
tagaggattt ggtaacaagc ttaaggacgc cattcatagg taagtctatt gaagcatgtt  5100
actgatattc ctcctatata atttactata cagagtttgt ctttacagta caagctatag  5160
gattttagtt ttgttaaagc agattctccg caatgaacta gactttttca cattgtaata  5220
acattgagtt tgtgtacttt atgcagattg aagctgaggt atggattggg gcggccgttt  5280
```

-continued

```
aagaaactcg agtccaatca ggttgaggct aacaagtttg cgctgatctg gaatgagata   5340
atcttagctt tcagagagga ggatatagtc tctgatcgag aagtagagct gctggagctg   5400
ccaaagaatt cctggaatgt aacagttatc cgctggccgt gtttcctgtt gtgcaatgag   5460
cttttgcttg cactgagcca ggcgaaagag ctggttgacg cacctgataa atggctgtgg   5520
cacaagatat gcaagaatga gtacaggcgg tgtgctgtgg ttgaggcata tgaaagcatc   5580
aaacatctgt tgctttcaat catcaaaatt gacactgaag aacataaaat tgttacaatt   5640
ttctttcaga tgattgaggt ctctattcag ggtgagcagt tcaccaagac cttcaaagtg   5700
gacctttttgc caaagattta tgagacacta cagaagttgg ttggtctgtt gaatgatgag   5760
aaagtggatg ttgggcgagt ggtgaatggt ctgcaatcta tttatgagat tgcaacacga   5820
cagttcttca tagaaaagaa gacgactgaa cagctatcta ctgagggtt aactcctcat   5880
gatccagcct caaagttact gtttcagaat gctgttaggc ttcccgatgc aagcaatgaa   5940
gacttcttcc ggcaggttag gcggttacac acaattctca cttctaggga ctctatgcac   6000
agcgtccctg tgaatctaga ggcgagacgg cggattgcct tcttcagcaa ttcgctcttc   6060
atgaacttgc ctcatgcacc tcaggtggag aaaatgttgg cgttcagtgt tatgactcca   6120
tactacagcg aggaagttgt atacagcaaa gaacagctcc gaaatgtgac tgaggatgga   6180
atttcaacct tgtattacct gcagacgatt tatgccgacg aatggaaaaa ttttaaggaa   6240
cggatgcgta gggaaggtat aaagacagat gttgagttgc ggacaaccaa gctgagagag   6300
ctcaggcttt gggcttccta cagaggtcag actttggcac gtacagttcg aggaatgatg   6360
tactattaca gggctcttaa gatgcttgct tttcttgact ctgcgtctga aatggacatt   6420
cgggaggatg ctcaggagct tggttcaatg aggagttcgc agggaaatcg attggatggg   6480
gttgacgatg taaatgacgg atcttctcta agcagagcaa ctagctctgt gagcatgctg   6540
tataaaggcc atgagcatgg gactgcattg atgaaattca catatgtcgt ggcgtgccag   6600
atctatgggt ctcaaaaagc gaagaaggag cctcaggcag aggaaattct gtatcttatg   6660
aagcaaaacg aagccctccg tattgcatat gtggatgagg tacatgcggg caggggagag   6720
actgagtatt actccgttct ggtgaaatac gatcatacgt tggagaggga agtggagata   6780
ttccgtgtga agctacctgg tccggtgaag ctgggtgagg gaaagccaga gaaccagaat   6840
catgcaatga tctttacccg tggtgatgct gttcagacca tagatatgaa ccaggataat   6900
tatttttgagg aggctctcaa gatgagaaat ttgctccagg agtttaggca ttatcatggg   6960
atcagaaaac caactattct tggtgtccgg gagcacatct tcacgggatc tgtctcgtct   7020
ctggcatggt tcatgtctgc tcaggagact agtttcgtca ctcttggtca gcgtgttctc   7080
gccaatccgc tgaaggtcag aatgcattat ggtcatcctg atgttttga cagattctgc   7140
ttcttgagtc gaggtggcat cagcaaagct tctagagtta taaatatcag tgaggacatc   7200
ttcgccgggt ttaattgcac attgcggggc ggtaacgtca cccaccacga gtatattcag   7260
gtagggaaat gttcatcatt tggatattct aactaattta tacatcgaca acaatactat   7320
aattccactt tttttgttat aaccttcgtg tgtgtgcata tgtattcagg ttgggaaggg   7380
tcgagatgtt ggattgaatc aaatatcaat gtttgaggct aaggtagcca gtgggaatgg   7440
agagcaggtt cttagccgag atgtgtacag gctgggtcat aggctcgatt tcttcagaat   7500
gttatcattt ttctacacaa cggtggggtt tttcttcaac acgatgatgg tcattctcac   7560
tgtctacgct ttcctctggg gtcgggttta tcttgctctg agcggtgttg agaagtccgc   7620
tctagcagac agcacagaca ccaacgcagc gcttgctgtg atattgaacc agcaattcat   7680
cattcagctt ggtctcttca cagctctgcc aatgattgtg gaatggctc tcgaggaggg   7740
tttccttcta gcgatatgga atttcattcg gatgcagatt cagctttcat ctgtcttcta   7800
cacattctca atggggacca gagctcacta ttttggccga accattctcc atggtgagac   7860
aaagtacaga gccactgggc gtggatttgt tgtcgagcac aagagcttca ctgagaatta   7920
ccgtctatac gcacgcagtc actttgtgaa ggccatcgag cttgggctga tcctcatagt   7980
ctacgctacg cacagtccca tcgccaaaga ctcattgatc tatatagcta tgactctcac   8040
cagctggttc ctcgtgattt catggatact ggccccttt gtgttcaacc cgtcaggatt   8100
cgactggctt aagacggtct atgacttcga aggcttcatg aactggatct ggtatcaagg   8160
cagaatctca acgaagtccg aacagagctg ggagatatgg tggtatgagg aacaggacca   8220
cctgagaacc accggtatac caggaagaat cgtggagata atcttggacc ttcggttttt   8280
cttcttccag tacgggattg tataccagct caaaatcgca aacggatcaa ccagcattct   8340
cgtctactta ctctcatgga tatacatctt cgcagtgttt gtgttcttcc tagtaatcca   8400
atacgcccgt gacaagtact cagcgagaaa ccacatacgg tacaggctcg tccagttcct   8460
cctgatcgtg tttggtacac tggtgattgt tgctctcctc gagttcacgc atttcagctt   8520
cgtggatatc ttcacgagtc ttcttgcgtt cgtcccaacc ggctgggggaa tcttgctgat   8580
cgcacaggct ttgaggcctg cgctgcagaa gatcgggctt atctggaacg cggttgtctc   8640
ccttgctcgg ttgtatgaca tactgttcgg gatagtcatc atggtccccg tagcgttcat   8700
gtcgtggatg cctgggtttc aatcgatgca aacgaggatc ttattcaatg aagcttttag   8760
cagagggctt cgtatcatgc agattgtcac tgggaagaaa tcaaaaggcg atgtcgaagt   8820
tgaaaaaaga aggtaaagct tcttatttac ccaaacatct tttatgttct gtttgtttgg   8880
aatcttaaat tacaacaaca ctaatgcaaa gcttttataa cttgtgtagg tcttgaggta   8940
tatggtaatt taaaagttgc tggtttgcgg cgatgaggt agtttgtat tcttataagt   9000
tatgcttctt gtctgaataa gaactcagac acccgtgttt tgtcttcttc ttattttaaa   9060
ccaggtttt ggagagcttt ggttgaggaa gctatttgat tagttcatcg gttagtggga   9120
gaaacatata tatacatttg tcagtacttt gttagagtgt gtggaaatgg ggacgactctc   9180
gattctgatt cctatgtgg ttattgtctg aaacgttaca gcatttttgtg aagtaggctt   9240
ttgtgcaaga tttgatatct ttctctcatt gtagagcttc agagcatttt ttagtatatg   9300
tttaatcttt gattttctta atgtcatttg cattcatatt tcac              9344
```

```
SEQ ID NO: 5           moltype = DNA   length = 8624
FEATURE                Location/Qualifiers
source                 1..8624
                       mol_type = genomic DNA
                       organism = Brassica oleracea
SEQUENCE: 5
gtttctttt ttttttggtc gaaattatat tattgtttct ctgagctgtt accattacat   60
taacaattta cattctatcc ttttgatgaa aaatattata aaatgtttaaa agaagttatt   120
agaaaaggag aggaaaacag ggggagagca tggaggggtc ccatgtgtgt ttcggaaagc   180
agcaaacatg actttgtaaa gtcttgtttt agcgtccaaa gcggtctcac tcgccgttca   240
```

-continued

```
gcgagcttta gctgttaaat tttcttgaaa taaatcgctc cacttgttaa aaaaaaaaat    300
gataactgtg tccatttcga ctaatatcta ttttgtgtca tttttgcata taatattttt    360
taatatttt  gaaataaat  ttaataaata gtttttataa caaaaaaaat tgaaaaatag    420
taactattga taaaatacct atatgaactt agtagtattt tttttcagtt ctaaaaatgt    480
ttaaatcata attttcagat tatgttataa ataaagcaga aatgacattc tacgaagtag    540
aaaacgaaat ccatttttt  tcattgaatc tacaatgttt agaatacgaa atcttcgtaa    600
ataagagtat tctaaaaata tttagaatac acattccgcg cttaacctac cgatctaaaa    660
tctttagaaa tcaaaatcta cagattaata taaatctaaa acacgttgaa accgacttct    720
acagatttac tgtaaatcta aaacatgtag aaatcaaaat tctacacatt actataattc    780
taaaaaccta tagaaaccga tttctacata ttatctgtat tctacggata agaaatcagt    840
tcttaaaaat atggaaacaa aatatttgag aatattcact ttcatatttt gaaaaaaatc    900
gatttaaaaa aaacaaaaaa aacaaaaaac cttcttttca cgccgtcttc tatattccat    960
tgattgttca caaattttc  acattatttc caccatatca gtgtgaaatt gagtgagtta   1020
gggtttatga acttgagact ttgattttct ccctttttgt tcgtgaagga gatgagaaat   1080
tatgagtttc atctcaaaga aatcgagttt aaagagttga aatcgtgttt ggtcggttca   1140
aatcaagtgg gaattaaacc ggatataacc gaagaaaacc aggaaatcga tttggaatac   1200
ttacctaggc acaagatcga tcggtctata attagagatc ggttgatctg tatgaaatcg   1260
actttgccg  atcgagtgaa atggaccagg tcgatcagcc gcgttttttt gttctgcata   1320
atgatcagaa tcggtcaatc cgtccgacct tgtaatttcg gatcgatcga tcccgcttga   1380
tcgaacctat tatttattat atttaagaat tacaattta  aggattttat tgccattttg   1440
aaaataatta gtctaattga acataaaata tataagatta gtctaaaatg acatagttat   1500
cattttttgt tctaaaaaaa caatttccct tttttatttt tgtttctttc aacacacttg   1560
tattaataac aataatgata ttgctaatct tgaacaaatc gtggattgtc ttttcttccg   1620
gtgatatcat cctagtcaa  aacatctcaa attaaataag tatagagttg tgaatgtttt   1680
taaaagtttg gcgtttgtat agatcactgt cagtgtcatg aatcattagg tgactgcaaa   1740
tttttatatg acaaaaaaga gagttgatac ttgccatttc cgagattttg aagttttttt   1800
cgtcgtcaac atacaaactc aacatttcg  aaatcttgga ttaaaaataa aaatatggac   1860
aaaacgatac ttattaatta attatgtact agcgtcttaa cattattaat atagatataa   1920
ttataagaac aagaaacata aacatatatg cacaaagcct caaagcaaat ttaaataatg   1980
ttacaaaaca agggatgtac ttgttatgaa aaattaatat ataaccattc ttaacatatt   2040
tttacgtaaa ccttaaactt tataaagaaa aatatgtaac attccggtgc gtggtatata   2100
gaaatatttt taaaaattga tttgactatt tccattagca aaatgcattt atttttttcga   2160
tcatacattt atttaaaatt tcagggttaa acgtgattaa aatggagtaa taagaatatg   2220
gatgatctac cagaaaatca ttacgtttt  aagtgagacc aaaatacgga taaaaatcat   2280
gtgatgattg tatggttatt aaacaattat tttgaatttg aaaataatta actcatcaaa   2340
ttaaacctaa ggaccgagta agcggacgca gatagccgta agcggttggg ccgtcacaaa   2400
atttatgacc aacaagaaaa tgaaactgat tttagtggat gatatatttt agaaagtaat   2460
aaaatggttc cagatttcaa tacttcaatg gttttttttat gctgactttc ttttcctctt   2520
ttacttacat gataaggaaa cgagagaggt tgaagaaaca aagaaaattc ctaaggattt   2580
agaaatgtat cttcaaaaaa tctaagtatt taccaagtaa aatcatacaa aataaggaaa   2640
aaaaaagaat ttatttccca atttggtttt taccggaaaa aaaattgttt taataaaaatc   2700
ttatgcacca aatcatataa gaacgaacca taacaaactt tatttgacca ttgtcattag   2760
tttatttat  ttatggtaat ggatcttcaa ataatttgaa ttaaattaaa aaaaagaata   2820
aaaaaagaga aacaaaaacg cggaaaggag agcccaaatc gtctccgtct gtcattgtcg   2880
cagtctctca cagctaaata aaagagaaaa acaaatcgca acgcttcaat atctctctcc   2940
caatcgtttg aattagtctt cctcatcaca ataccctaa  gatccacctc acatgctact   3000
atgagcctcc gccaccgcac caccgtcccc tctcaaccgg gacggcccc  ggcggcgggc   3060
gcaatcgacg aggagcccta caacatcatc cccgtcaaca acctcctcgc cgaccacccc   3120
tccctccgct acccgaggt  ccgcgccgcc gccgccgccc tcaaaaccgt cggagacctc   3180
cgccgcccca cctacgtcca atggcgcccc cactacgacc tcctcgactg gctcgccctc   3240
ttcttcggct tccagaagga caacgtccgc aaccagcgcg agcacctcgt cctacacctc   3300
gccaacgccc agatgcgcct cacgccgccg ccggataaca tcgattccct cgatcccgcc   3360
gtcgtccgcc gtttccgccg caagctcctc ggtaactact cgagctggtg ctcgtacctc   3420
gggaggaagt cgaacatctg gatctcggat cggaaccccg attcgaggcg ggagcttctc   3480
tacgtcggcc tctacctcct cgtgtggggg gaggcggcga tcttaggtt  tatgccggag   3540
tgtatctgtt acatcttcca caatatggcc tcggagctta acaagatcct cgaggattgc   3600
ctcgacgaga gcacggggca gccgtattct cctagaatca cggggggagaa tagtttccta   3660
aacggcgtcg ttaaacctat ttacgagacg atcaaagctg agattaacga gagcaagaac   3720
gggacggagc cgcattgtaa gtggaggaac tatgatgata ttaacgagta cttttggacg   3780
gataggtgtt tcagtaaatt gaaatggccg attgatttgg ggagcagttt cttcaagagt   3840
agtagaggga gcggcgttgg gaagacaggt tttgtggagc ggaggacgtt tttttacctc   3900
tacaggagct ttgataggct ttgggtgatg cttgctttgt ttcttcaagc tgctattata   3960
gttgcttggg aggagaagcc gggtggaggg tcggtgagga gtcagctctg gaatgcgttg   4020
aagtcgacgg atgttcaggt gaggcttttg actgtgtttt actgtgggag tgggatgaga   4080
ttactgcagg ctgtgctgga cgctggctcg caacggccgc ttatttctag agagaccaaa   4140
cggctgtttt tcagaatgct gatgaaggtt gtagctgcta cggtttggat cattgctttt   4200
attgttctct acacgaacat ctggaagcag aggaagcaag acaggcagtg gtccagagcc   4260
gcgaatgaca agatctacca gttcctttac gctgtggtgg ctttcttggt ccctgagatc   4320
ctggcttttg gctctgtttat agtcccgtgg ataaggaact ttctggaaga gaccaattgg   4380
aagatattct ttgctttgac ttggtggttc caggtaaaa  gctttgtggg tcgaggtttg   4440
agagaggggt tggtggacaa catcaagtac tcgactttct ggatctttgt cctagcaacg   4500
aagttcacgt tcagctactt cctgcaggtt aagccaatga ttaaaccctc gaagctgcta   4560
tggaatttga aggaggtgga ttatgagtgg catcagttct tttggcaagag caataggttt   4620
tctgtcttgt tattgtggct gccagtggtg ttgatatacc tgatggatat ccaaattttg   4680
tacgcgatct attcttcgat tgttggtgct gttgttgggc tgtttgatca tctggggggag   4740
atcagggaca tgggacagct taggctgagg tttcagttcc ttgctagcgc tattcagttc   4800
aacctaatgc ctgaggaaca actcctgaat gctagaggat ttggtaacaa gcttaaggac   4860
gccattcata ggtaagtcta ttgaagcatg ttactgatat ttctatataa tttattatac   4920
agagtttgtc tttacagtac aagctatagg atttttagttt tgttaaagaa gatttctccg   4980
```

```
caatgaactc gacttttcac attgtaataa cattgagttt gtgtacttta tgcagattga   5040
agctgaggta tggattgggg cggccgttta agaaactcga gtccaatcag gttgaggcta   5100
acaagtttgc gctgatctgg aatgagataa tcttagcttt cagagaggag gatatagtct   5160
ctgatcgaga agtagagctg ctggagctgc caaagaattc ctggaatgtg acagttatcc   5220
gctggccgtg tttcctgttg tgcaacgagc ttttgcttgc actgagccag gcgaaagagc   5280
tggttgacgc acctgataaa tggctgtggc acaagatatg caagaatgag tacaggcggt   5340
gtgctgtggt tgaggcatat gaaagcatca aacatctgtt gctctcaatc atcaaaattg   5400
acaccgaaga acataaaatt gttacaattt tctttcagat gattgaggtg tctattcagg   5460
gtgacagtt caccaagacc ttcaaagtgg acctattgcc aaagatttat gagacgctac   5520
agaagttggt tgggctgttg aatgatgaga aagtggatgt tgggcgagtg gtgaatggtc   5580
tgcagtctat ttatgagatt gcaacacgac agttcttcat agaaaagaag acgactgaac   5640
agctatctac cgaggggtta actcctcatg atccagcctc aaagttactg tttcagaatg   5700
ctgttaggct tcccgatgca agcaatgaag acttcttccg gcaggttagg cggttacaca   5760
caattctcac ttctagggac tctatgcaca gcgtccctgt gaatctagag gcgagacggc   5820
ggattgcctt cttcagcaat tcgctcttca tgaacttgcc tcatgcacct caggtgggaga  5880
aaatgttggc gttcagtgtt atgactccat actacagcga ggaagttgta tacagtaaag   5940
aacagctccg aaatgagact gaggatggga tttcaacctt gtattacctg cagacgattt   6000
atgccgacga atggaaaaat tttaaggaac ggatgcgtag ggaaggtata aagacagatg   6060
ttgagttgtg gacaaccaag ctgagagagc tcaggctttg ggcttcctac agaggtcaga   6120
ctttggcacg tacagttcga ggaatgatgt actattacag ggctcttaag atgcttgctt   6180
ttctcgactc tgcgtctgaa atggacattc gggaggatgc tcaggagctt ggttcaatga   6240
ggagttcgca gggaaatcga ttggatggtg ttgacgatgt aaatgaccga tcttctctaa   6300
gcagagcaac tagctctgtg agcatgctgt ataaaggcca tgagtatggg actgcattga   6360
tgaaattcac atatgtcgtg gcgtgccaaa tctatgggtc tcaaaaagcg aagaaagagc   6420
ctcaggcaga ggaaattctg tatcttatga agcaaaacga agcccttcgt attgcatatg   6480
tggatgaggt acatgcgggc aggggagaga ctgagtatta ctccgttctg gtgaaatacg   6540
atcacacgtt ggagagggaa gtggagatat tccgtgtgaa gctacctggt ccggtgaagc   6600
tgggtgaggg aaagccagag aaccagaatc atgcaatgat ctttacccgt ggtgatgctg   6660
ttcagaccat agatatgaac caggataatt attttgagga ggctctcaag atgagaaatt   6720
tgctccagga gtttaggcat tatcatggga tcagaaaacc aactattctt ggtgtcagag   6780
agcacatctt cacgggttct gtctcgtctc tggcttggtt catgtctgct caggagacaa   6840
gtttcgtcac tcttggtcag cgtgttctag ccaacccgct gaaggtcaga atgcattatg   6900
gtcaccctga tgtatttgac agattctggt tcttgagtcg aggtggcatc agcaaagctt   6960
ctagagttat aaatatcagt gaggacatct tcgccgggtt taattgcaca ttgcggggcg   7020
gtaacgtcac ccaccacgag tatattcagg tagggaaatg ttcatcattt ggatattcta   7080
actaatttat acatcgacaa caatactata attccacttt tttgttataa ccttttttgtg   7140
tgtgcatatg tattcaggtt gggaagggtc gagatgttgg attgaatcaa atatcaatgt   7200
ttgaggctaa ggtagccagt gggaatggag agcaggttct tagccgagat gtgtacaggt   7260
tgggtcatag gctcgatttc ttcagaatgt tatcatttt ctacacaacg gtggggtttt    7320
tcttcaacac gatgatggtc attctcactg tctacgcttt cctctggggc cgggtttatc   7380
ttgctctgag cggtgttgag aagtccgctc tagcagacag cacagacacc aacgcagcgc   7440
ttgctgtgat attgaaccag cagttcatca ttcagcttgg tctcttcaca gctctgccaa   7500
tgattgga atggtctctc gaggaggggtt tccttctcgc gatatggaac ttcattcgga   7560
tgcagattca gctttcttct gtcttctaca cattctcaat ggggaccaga gctcactatt   7620
ttggccgaac cattctccac ggtggagcaa agtacagagc cactggacgt ggatttgttg   7680
tcgagcacaa gagtttcact gaaaactacc gtctatacgc gcgcagtcac tttgtgaagg   7740
ccatcgagct tgggctgatc ctcatagtct acgctacgca cagtcccatc gccaaagact   7800
cattgatcta tatagccatg actctcacca gctggttcct cgtgatttca tggatactag   7860
ccccttttgt gttcaacccg tcaggtttcg actggcttaa gacggtctac gacttcgaag   7920
gcttcatgaa ctggatctgg tatcaaggca gaatctcaac gaagtccgaa cagagctggg   7980
agatatggtg gtatgaggaa caggaccacc tgagaaccac cggtctacca ggaagaatca   8040
tggagataat cttggacctt cggttttttct tcttccagta cgggattgta taccagctca   8100
aaatcgcaaa cggatcaacc agcgttctcg tctacttact ctcatggata tacatcttcg   8160
cagtgtttgt gttcttcctg gtaatccaat acgcccgtga caagtactca gcgagaaacc   8220
acatacggta caggctcgtt cagttcctcc tgatcgtgtt tggtacactg gtgattgttg   8280
ctctcctgga gttcacgcat ttcagcttcg tggatatctt cacgagtctt cttgcgttcg   8340
tcccaaccgg ctgggaatc ttgctgatcg cacaggcttt gaggcctgcg ctgcagaaga   8400
tcgggcttat ctgaacgcg gttatctccc ttgctcggtt atatgacata ctgttcggga   8460
tagtcatcat ggtccccgta gcgttcatgt cgtggatgcc tgggtttcag tcgatgcaaa   8520
cgaggatctt attcaatgaa gcttttagca gagggcttcg tatcatgcag attgtcactg   8580
ggaagaaatc aaaaggcgat gtcgaagttg gtaa                               8624
```

```
SEQ ID NO: 6           moltype = DNA   length = 9270
FEATURE                Location/Qualifiers
source                 1..9270
                       mol_type = genomic DNA
                       organism = Brassica juncea
SEQUENCE: 6
ctgtcagatt tagtttcaca aaatctttgt aacttcgcgg tttttgatat ggaagttgct   60
acaaaaactg acttgtgata ttataatctt tcggcaagaa aaatatataa tactaatttc   120
agaaagtatt ctgttgaatt gttgatcacc aaatacacat aaaccggcag atgttgacat   180
gtttacgtgg gatcactggg atagaagttt tgcttctgta ttagtatcgc gaaccggttt   240
gtagtagcga aaataacatt attattttca gatttcatca tcgtcaaatt caacgttaca   300
tttgaacagg cttgtaaaaa gtggacatgt ggcatgagta aagataaag aaaattgtga   360
gccttttgt taatacgaaa aagccgaaaa cgttattatt tctatcatcg gcaaatttaa   420
tgttaaattt gctccacatc attcagaggg tatatgtata tttttctaat gcttcggtga   480
agcacatgcg accatttgtt gcgtcagaag tcagaacaaa aggaagattc catctaatgg   540
attataatcc cacatgccca ttttaaaac tagacaaaat aacttataat agtcccataa   600
gagcattaag acaaactgaa ccaaaaagaa tcttaaatgc tggtgaatct agtctcgaat   660
```

```
gctgctgaac actcctgata ttagaatttg gcagaaaata ttcatactaa taacagtaaa    720
tacatttcaa aacaagaaaa tagtagtagt aaataaaaac aattaatatg ttattattgt    780
ttctcttagc tgttaccatt acattaacaa tttacattca atcctttaa tgaaaaatat     840
tataaaatat taaaagaagt tattagaaaa ggagagggat atggggggg gagagcatgg     900
aggggtccca tgtgtgtttc gaaaagcagc aaacatgact ttgtaaagtc ttgttttagc    960
tagagttcca aaaaaaaaag agttcaaaaa aaaagaaaaa aaaaagtctt gtttttagcgt   1020
ccaaagcggt ctcactcgcc gttcagctgt taaattttct tgaaataaat cgctccactt   1080
gtttttattt tttgtttctt tcaacccact tgtattaata acaataatga tattgctaat   1140
cttgaacaaa tcgtggattg tcttttcttc cagtgtatc atccttagtc aaaacatctc    1200
aaattaaata aatatatagt tgtgaattaa aaaaaaggta tagagtttat aaaattagca    1260
tttgcgaatg tttttaaaag tttggcgttt gtatagatca ctgtcagtgt catgaatcat    1320
tcggtgacag caaatttgta tatgccaaaa aagagagttg atacttgcca ttctcgatat    1380
tttgaatttt ttttcgtcga catacaaact caacattttc gaaatcttag attaaaaaca   1440
aaatggacaa aacgatactt attaatgaat tatgtactag cgtctgaaca ttagtaacat    1500
agatataatt ataagaacaa gaaacatata tgcacaaagc ctcaaaccaa atttaaatag    1560
tgttacgaaa caagggatgt acttgttatg aaaaattaat gtataaccat tcttagcatt    1620
ttttacctaa cccttaaact ttataaagaa aaatatgtaa catttcggtg tgtggtatat    1680
aaaagtattt tgaaaatcga tttgattatt tctattatta aaatgtactt actttttta    1740
tcacacattt atttacaatt tcagagttaa acatgattaa gacaaagtag tgaaaatata    1800
gatgatctac cagaaaatca tttgctttct gagtgagatc aaaataaagg caaaaataat   1860
gtgatgattg tatattaaac aattattttg aatttgaaaa gaataactca tcgaatgaag    1920
cctatgaacc gagtaagcgg tgaagcggtt ggaccgtcac aaaaattatg accaacaaga   1980
aaataaaatt gatattagtg aagggcaatt gtcaataata gcacctttg aagtttatgt    2040
ctcaaaaata gcactagaag gagaaagtca caaaatgac attcattaaa gggtaaaata    2100
tctataatac ccttggttta aaattaaata aacaaactaa aataaataaa aataaaaaaa   2160
taaaaaaaat aaaaataaaa aaaataaatt tttttttaa gtttcagatt atatgttttc    2220
agattcgaaa tttttataat ttttttttaa aaaaaaattt taaatctttt ttttatttt    2280
ttttcagatt ttattttat aatttaaaaa tacttttttga aactgttttt aaaatttta    2340
ttttttattt tattatttat tatttataaa attttaaatc ctaattccaa aaccccaccc   2400
cttaactcta aaccctaatg tttggattaa ttaaccctag gggtataagt gtacattacc   2460
tctttaatga aacctatttt tgtgactttg aaccttgagt gctactttgg gaacaaaaac   2520
ttggtttggt gctattctag tattttctc attagtgaat gatatatttt agaaagtaat   2580
aaattggttc cagatttcaa tacatcaatg ttttttctaat gctgacttgc ttttcctctt   2640
tttcttacat gataaggaaa cgagagaggt cgaagaaaca aagaaacttc ctaagcattt   2700
agcaacgcat cttcaaaaaa tctagtattt accaagtaaa atcatacaaa ataaggaaaa   2760
aaagaagaat atatttccca atttggtttt caccggaaaa aaaaaactgt cttaacaaaa   2820
tcttaatgca ccaaatcata taagaacttt atttgaccat tgtcattagt ttttttcctta  2880
tggtaatgga tcttcaaata atttaaatta aattaaaaaa aaaaagaaaa gagaaacaaa   2940
aacgcggaaa ggagagccca aatcgtctcc gtctgtcatt gtcgcagtct ctaaaagaga   3000
aaaacaaatc gcaacgcttc tctctctctc cctatcgttt gaatcagtct ctcaagatcc   3060
accaccacca cacatgctac tatgagcctc cgccaccgca ccgtcccctc tcaacccgga   3120
cggcccccgg cggcgggcgc aatcgaggac gagccctaca acatcatccc cgtcaacaac   3180
ctcctcgccg accacccctc cctccgctac cccgaggtcc cgccgccgc cgccgccctc    3240
aaaaccgtcg gcgacctccg ccgcccacc tacgtccaat ggcgcccca ctacgacctc     3300
ctcgactggc tcgccctctt cttcggcttc cagaaggaca acgtccgcaa ccagcgcgag   3360
cacctcgtcc tccacctcgc caacgcccag atgcgcctca ccccgccgcc ggacaacatc   3420
gattccctcg atcccgccgt cgtccgccgc ttccgccgca agctcctcgg taactactcc   3480
agctggtgct cctacctcgg gaggaagtcc aacatctgga tctcggatcg gacccccgat   3540
tcgcggcggg agcttctcta cgtcggcctc tacctcctcg tgtggggcga ggcggcgaat   3600
cttaggttta tgcctgagtg tatctgttac atcttccaca atatggcctc ggagcttaac   3660
aagatcctcg aggattgcct cgacgagagc acggggcagc cgtattctcc taagatcacg   3720
ggggagaata gtttcctaaa cggcgtcgtt aagcctatct acgagactat taaagctgag   3780
attaacgaga gcaagaacgg gacggagccg cattgtaagt ggaggaacta tgatgatatt   3840
aatgagtact tttggacgga taggtgtttt agtaaattga aatggccgat tgatttgggg   3900
agcagtttct tcaagaacag cagaggtagc ggcgttggga agactggttt tgtggagagg   3960
aggacgtttt tttacctcta caggagcttt gataggcttt gggtgatgct tgctttgttt   4020
cttcaagctg ctattatagt tgcttgggag gagaagccgg gtggagggtc ggtgacgagt   4080
cagtctgga atgcgttgaa gtcgacggat gttcaggtga ggcttttgac tgtgttcttg   4140
acgtggagtg ggatgaggtt gttgcaggct gtgttgacg ctggctcgca acggtcgctt    4200
atttctagag agaccaaacg gctgtttttc agaatgttag tgaaggttgt ggctgctacg   4260
gtttggatag tagcgtttat tgttctctac acgaacatct ggaagcagag gaagcaagat   4320
aggcagtggt ccagagccgc gaatgataag atttatcagt tcctttacgc tgtggtggct   4380
ttcttggtcc ctgagatcct ggctttggct ctgtttatag tcccgtggat aaggaacttc   4440
ctggaagaga cgaattggaa gatattcttt gctttgactt ggtggttcca ggggaaaagc   4500
tttgtgggtc gaggtttgag agaggggttg gtggacaaca tcaagtactc gactttctgg   4560
atctttgtcc ttgcaacgaa gtttacgttc agctacttcc tgcaggttaa gccaatgatt   4620
aaaccctcga agctgctatg gaatttgaag gaggtggatt atgagtggca tcagttcttt   4680
ggcgagagca ataggttttc tgtcttgtta ttgtggctgc caatggtgtt gatatacctg   4740
atggatatcc aaatttggta cgcgatctat tcttcgatta ttggtgctgt tgttgggctg   4800
tttgatcatc tggggggagat cagggacatg ggacagctta ggctgaggtt tcagttcttt   4860
gctagcgcta ttcagttcaa cctaatgcct gaggaacaac tcctgaatgc tagaggatit   4920
ggtaacaagc ttaaggacgc cattcatagg taagtctatt gaagcatgtt actgatattt   4980
ctatataatt tactatatag tttgtcttta cagtacaagc tatgggattt tagttttgtt   5040
aaagcagatt tctccgcaat gaactcgact tttcacattg taataacatt gagtttgtgt   5100
actttatgca gattgaagct gaggtatgga ttggggcggc cgtttaagaa actcgagtcc   5160
aatcaggttg aggctaacaa gtttcgcgctg atctggaatg agataatcct agctttcaga   5220
gaggaggata tagtctctga tcgagaagta gagctgctgg agctgccaaa aaattcctgg   5280
aatgtgacag ttatccgctg gccgtgtttt ctgttgtgca acgagctttt gcttgcactg   5340
agccaggcga aagagctggt tgacgcacct gataaatggc tgtggcacaa gatatgcaag   5400
```

```
aatgagtaca ggcggtgtgc tgtggttgag gcatatgaaa gcatcaaaca tctgttgctc   5460
tcaatcatca aaattgacac cgaagaacat aaaattgtta caattttctt tcagatgatt   5520
gaggtgtcta ttcagggtga gcagttcacc aagaccttca aagtggacct tttgccaaag   5580
atttatgaga cactacagaa gttggttggg ctgttgaatg atgagaaagt ggatgttggg   5640
cgagtggtga atggtctgca gtctatttat gagattgcaa cacgacagtt cttcctagaa   5700
aagaagacga ctgaacagct atctactgag gggttaactc ctcatgatcc agcctcaaag   5760
ttactgtttc agaatgctgt taggcttccc gatgcaagca atgaagactt cttccggcag   5820
gttaggcggt tacacacaat tctcacttct agggactcta tgcacagcgt ccctgtgaat   5880
ctagaggcga gacggcggat tgccttcttc agcaattcgc tcttcatgaa cttgcctcat   5940
gcacctcagg tggagaaaat gttggcgttc agtgttatga ctccatacta cagcgaggaa   6000
gttgtataca gcaaagaaca gctccgaaat gagactgagg atgggatttc aaccttgtat   6060
tacctgcaga cgatttatgc cgacgaatgg aaaaatttta aggaacggat gcggagggaa   6120
ggtataaaga cagatgttga gttgtggaca accaagctga gagagctcag gctttgggct   6180
tcctacagag gtcagacttt ggcacgtaca gttcgaggaa tgatgtacta ttacagggct   6240
cttaagatgc ttgcttttct tgactctgcg tctgaaatgg acattcggga ggatgctcag   6300
gagcttggtt caatgaggag ttcgcaggga aatcgattgg atggggtgga cgatgtaaat   6360
gacggatctt ctctaagcag agcaactagc tctgtgagca tgctgtataa aggccatgag   6420
catgggactg cattgatgaa attcacatat gtcgtggcgt gccagatcta tgggtctcaa   6480
aaagcgaaga aggagcctca ggccgaggaa attctgtatc ttatgaagca aaacgaagcc   6540
ctccgtattg catatgtgga tgaggtgcat gcgggcaggg aagagactga gtattactcc   6600
gttctggtga aatacgatca cacgttggag aaggaagtgg agatattccg tgtgaagcta   6660
cctggtccgg tgaagctggg tgagggaaag ccagagaacc agaatcatgc aatgatcttt   6720
acccgcggtg atgctgttca gaccatagat atgaaccagg ataattattt tgaggaggct   6780
ctcaagatga gaaatttgct ccaggagttt aggcattacc atgggatcag aaagccaact   6840
attcttggtg tccgggagca catcttcacg ggatctgtct cgtctctggc ttggttcatg   6900
tctgctcagg agacaagttt cgtcactctt ggtcagcgtg ttctagccaa cccgctgaag   6960
gtcagaatgc attatggtca ccctgatgta tttgacagat tctggttctt gagtcgaggt   7020
ggcatcagca aagcttctag agttataaat atcagtgagg acatcttcgc cgggtttaat   7080
tgcacattgc ggggcggtaa cgtcacccac cacgagtata ttcaggtagg gaaatgttca   7140
tcatttggat attctaacta atttatacat cgacaacaat actataattc cactttttt    7200
ttgttataac cttttttgtgt gtgcatatat gtattcaggt tgggaagggt cgagatgttg   7260
gattgaatca aatatcaatg tttgaggcta aggtagccag tgggaatgga gagcaggttc   7320
ttagccgaga tgtgtacagg ctgggtcata ggctcgattt cttcagaatg ttatcatttt   7380
tctacacaac ggtggggttt ttcttcaaca cgatgatggt cattctcact gtctacgctt   7440
tcctctgggg ccgggtttat cttgctctga gcggtgttga gaagtccgct ctagcagaca   7500
gcacagacac caacgcagcg cttgctgtga tattgaacca gcagttcatc attcagcttg   7560
gtctcttcac agctctgcca atgattgtgg aatggtctct cgaggaaggt ttccttctcg   7620
cgatatggaa cttcattcgg atgcagattc agctttcctc tgtcttctac acattctcaa   7680
tggggaccag agctcactat tttggccgaa ccattctcca cggtggagca aagtacagag   7740
ccactggacg tggatttgtt gtcgagcaca agagtttcac tgaaaactac cgtctatacg   7800
cacgcagtca ctttgtgaag gccatcgagc ttgggctgat cctcatagtc tacgctacgc   7860
acagtcccat cgccaaagac tcattgatct acatagccat gactctcacc agctggttcc   7920
tcgtgatttc atggatactg gccccttttg tgttcaaccc gtcaggattc gactggctta   7980
agacggtcta tgacttcgaa ggcttcatga actggatctg gtatcaaggc agaatctcaa   8040
cgaagtccga acagagctgg gagatatggt ggtatgagga acaggaccac ctgagaacca   8100
ccggtatacc aggaagaatc atggagataa tcttggacct tcggttttc ttcttccagt    8160
acgggattgt ataccagctc aaaatcgcaa acggatcaac cagcattctc gtctacttac   8220
tctcatggat atacatcttt gcagtgtttg tgttcttcct agtgatccaa tacgcccgtg   8280
acaagtactc tgcgagaaac cacatacggt acaggctcgt ccagttcctc ctgatcgtgt   8340
ttggtacact ggtgattgtt gctctcctcg agttcacgca tttcagcttc gtggatatct   8400
tcacgagtct tcttgcgttc gtcccaaccg gctgggggat cttgctgatc gcacaggctt   8460
tgaggcccgc gctgcagaag atcgggctta tctggaacgc ggttatctcc cttgctcggt   8520
tgtatgacat actgttcggg ataatcatca tggttcccgt agcgttcatg tcgtggatgc   8580
ctgggtttca atcgatgcaa acgaggatct tattcaatga agctttagc agagggcttc    8640
gtatcatgca gattgtcact gggaagaaat caaaaggcga tgtcgaagtt gaaaaaagaa   8700
ggtaaagctt cttatttacc caaacatatt ttatgttctg tttgtttgga atcttaaatt   8760
acaacaacac taatgcaaag cttttataac ttgtgtaggt cttgaggtat atggtaattt   8820
aaaagttgct ggtttgcggc gatgaggtta gttttgtatt cttataagtt atgcttcttg   8880
tctgaataag aactcagaca cccgtgtttt gtcttcttct tattttaaac caggtttttg   8940
gagagctttg gttgaggaag ctatttgatt agttcatcgg ttagtgggag aaacatatat   9000
atatacattt gtcagtactt tgttagagtg tgtggaggtg gggacgactc tgattctgat   9060
tccttatgtg gttattgtct gaaacgttac agcattttgt gaagtaggct tttgtgcaag   9120
atttgatatc tttctctcat tgtagagctt tagagcattt tttagtatat gtttaatctt   9180
tgattttcta atgtcatttg cattcatatt cacatccttct ctgcttcttc gttgtctgaa   9240
accagttttc agatgcttat ccattgtcca                                    9270
```

```
SEQ ID NO: 7             moltype = DNA  length = 6389
FEATURE                  Location/Qualifiers
source                   1..6389
                         mol_type = genomic DNA
                         organism = Brassica juncea
SEQUENCE: 7
tatcattgtc gcagtctctc tcacagctaa aaggaaaaca gatcgcaacg cttcaatatc   60
tctctctctc cattgttttg aattgaatca gtctcctcac ccttctccaa gatccaccac   120
accacatgcc actatgagcc tccgccaccg caccgtccca tctcaaaccg gacggccgtc   180
ggcggcggga tcgaggagg agccctacaa catcatcccc gtcaacaacc tcctcgccga    240
ccatccttct ctccgttacc ccgaggtccg cgccgccgcc gccgctctca aaaccgtcgg   300
cgacctccgc cgtcctccct acgtccaatg gcgtcctcac tacgatctcc tcgactggct   360
cgccctcttc ttcggcttcc agaaggataa cgtccgcaac cagcgcgagc acatggtgct   420
```

-continued

```
ccacctcgcc aacgctcaga tgcgtctcac gccgccgccg gataacatcg attccctcga    480
ttcgacggtt gtccgtcgct ttcgccggaa actcctcgga aactactcga gctggtgctc    540
ttatttaggg aagaaatcga acatctggat ctcggatcgg aaccctgatt cgaggcggga    600
gcttctctac gttggcctct acctcctcgt gtggggcgag gcggcgaatc ttaggtttat    660
gcctgagtgc atctgttaca tcttccataa catggcctcg gagcttaata agattctgga    720
agattgcctc gatgagaaca cggggcaacc ctatctgcct actctctcgg gggaaaacgc    780
tttcctaaac ggcgtcgtta aacctattta cgaaactatc aaagctgaga ttgatgagag    840
caagaacggg acggagccgc attgtaagtg gaggaactat gatgatatta atgagtattt    900
ctggacggat aggtgtttca gtaaattgaa gtggccgctt gatctgggaa gcagtttctt    960
caagagtagt agagggaaaa gcgttgggaa aaccggtttt gtggagcgca ggaccttctt   1020
ttacctctac aggagctttg ataggctttg ggtgatgctt gcgttgttcc ttcaggccgc   1080
cattataatt gcttgggagg aaaagccgga tagagggtcg gtgacagggc agctgtggaa   1140
tgccttgaag tccagagatg tccaggtgag gcttttgaca gtttttcttga cgtgggagtgg   1200
gatgagacta ctgcaggctg tgctggacgc tggttcgcaa cggtctctta tttctagaga   1260
gaccaaacgg ctcttttca gaatgttgat gaaggttgta gctgccacag tttggataat   1320
agcttttatt gtactctaca cgaacatctg gaagcagagg aagcaagaca gacagtggtc   1380
cagagccgcg aatgacaaga tctaccagtt cctttacgct gtggtggcct tcttgatccc   1440
tgagatcctg gctctggccc tgtttataat cccgtggatt aggaacttc tggaagagag   1500
caattggaaa atattctttg ctttaacttg gtggttccag ggtaaaagct ttgtgggtcg   1560
aggttttgaga gagggtttgg tggacaacat caagtactcg acgttctgga tcttcgtcct   1620
agcaacaaag ttcacattca gctacttcct acaggttaag ccaatgatta aaccctcgaa   1680
gctgctgtgg aacttaaagg aggtagatta tgagtggcat cagttctttg gcgagagcaa   1740
taggtttttct gtcttattat tgtgggctgcc agtggtgttg atatacctga tggatatcca   1800
aatttggtac gcaatctatt cttcgattgt tggtgctgtt gttgggctgt ttgatcatct   1860
gggggagatc agggacatgg gacagcttag gctgaggtt cagttctttg ctagcgctat   1920
tcagttcaac ctgatgcctg aggaacaact cctgaacgt agaggcttg gtaacaagct   1980
taaggacgcc atccataggt aagtctgtgg aagcatgtta ctgatttcct ttagagttta   2040
atgtacagag tttgtcttta cggtacaagc tatataattt tagttttgtt atagcagatt   2100
ctcgtaactt gacttttaa cattgttata accttgagtt tgtgtacttt atgcagattg   2160
aagctgaggt atggatttgg gcggccgttt aagaaactcg agtctaatca ggttgaggcc   2220
aacaagtttg ctttgatctg gaatgagata atcttagctt ttagagaaga ggatattgtc   2280
tctgatcgag aagtagagct actggagctg ccaaagaatt cctggaatgt gacagttatc   2340
cgctggccgt gtttcctgct gtgtaacgag cttttgcttg cactgagcca ggcgaaagag   2400
ctggttgatg ctcctgataa atggctgtgg cacaagatat gcaagaatga gtacaggcgt   2460
tgtgctgtgg ttgaggcata cgacagcatc aaacatcgt tgctctcgat catcaaaatc   2520
gacactgaag aacataaaat catcacggtt ttctttcaga tgattaaggt ttctattcag   2580
ggagagcagt tcaccaagac cttcaaagtg gatcttctgc caaagattta cgagacacta   2640
cagaagttgg ttgggctgtt gaatggtgag gaaccggata tcgggagagt ggtgaatgtt   2700
ctgcagtcta tatatgagat tgcaacacga cagttcttta tagaaaagaa gacaactgaa   2760
cagctatcta ctgaaggatt aactcctcat gatccagcct caaagttact gtttcagaac   2820
gctgttaggc ttcccgatgc aagcaatgaa gacttcttcc ggcaggtgag gcggttacac   2880
acaattctca cttctaggga ctctatgcac agcgtccctg tgaatctaga ggcgagacgt   2940
cggattgcct tcttcagcaa ttcgctcttc atgaacttgc ctcatgcacc tcaggtgaaa   3000
aaaatgttgg cgttcagtgt tatgactcca tactacagcg aggaagttgt atacagcaaa   3060
gaacagctca aaaatgagac tgaggacggg atttcaacct tgtattacct gcagacgatt   3120
tatgctgacg aatggaaaaa ttttaaggaa cggatgcgta gggaaggtat aaagacagat   3180
gatgagctgt atacaaccaa gctagagagg ctcaggcttt gggcttccta cagaggtcag   3240
actttggcac gtacagttcg agggatgatg tactattaca gggctcttaa gatgcttgct   3300
tttcttgact ctgcgtctga aatggacatt cgggaggatg ctcaggagct tggttcaatg   3360
aggagttcgc agggaaatct gggcggtcga tcgaatgggg ttgacgatgt aaatgaccga   3420
tcttctctaa gcagagctac tagctccgtg agcatgctgt ataaaggcca tgagcatgga   3480
actgcattga tgaaattcac atatgtcgtg gcgtgccaga tctatgggtc tcaaaaagcg   3540
aagaaggagc ctcaggcaga ggaaattctc tatcttatga agcaaaatga agccctccgt   3600
attgcgtatg ttgatgaggt gcatgcaggc aggggagaga ccgaatatta ctcagttctg   3660
gtgaaatacg atcacacttt ggagaaggaa gtggagatat tccgtgtgaa gctacctggt   3720
cccgtgaagc tgggtgaggg aaagccagag aaccagaatc atgcaatgat ctttacccgt   3780
ggtgatgctg ttcagaccat agatatgaac caggataatt attttgagga ggctctcaag   3840
atgagaaatt tgctccagga gtttagacat tatcatggga tcagaaaacc aactattctt   3900
ggtgtccgag agcacatctt cactggctct gtctcgtctc tggcttggtt catgtccgct   3960
caggagacta gtttcgtcac tcttggtcag cgtgttcttg ctaacccgct gaaggtcaga   4020
atgcattatg gccacccccga tgtatttgac agattctggt tcttgagtcg aggtggcatc   4080
agcaaagcgt ccagagtcat aaatatcagt gaggacatct tcgctgggtt taactgcaca   4140
ttgcggggcg gtaacgtcac acaccacgag tatattcagg ttggtaacta ttcattattt   4200
ggttatttct aactaattta tactgcgaca gcaatcctat ttcttttgtt   4260
ataaccatgc aacttaacgt tcattgtatc tgagtgtcaa tgtaaatttc ataaccctg   4320
tttttgtgca tatattcagg ttgggaaggg tcgagatgtt ggattgaatc aaatatcaat   4380
gtttgaggcg aaggtagcca gtgggaacgg agagcaggtt cttagccgag atgtgtacag   4440
gctgggtcat agactcgatt tcttcagaat gttatcattt ttctacacaa cggtcgggtt   4500
tttcttcaac acgatgatgg tcattcttac cgtttacgct ttcctatggg gccggattta   4560
tcttgctctg agcggtgttg agaagtccgc tctagcagac agtacagaca ccaacgcagc   4620
gcttgcggtt atattgaacc agcagttcat cattcagctc ggtctcttca cagcactgcc   4680
aatgattgtg gaatggtctc tcgaggaagg tttccttctt gcgatatgga atttcatccg   4740
gatgcagatt cagctttctt ctgtcttcta cacattctca atggggacca gagctcacta   4800
ttttggccga accatcctcc acggtgggagc aaagtacaga gccactggac gtggatttgt   4860
tgtcgagcac aagagtttca ctgagaacta cagactgtat gcacgcagtc actttgtgaa   4920
ggccatcgag cttgggctga tcctcatagt ctacgctacg cacagtccca tcgccaaaga   4980
ctcattgatc tatatagcca tgactctcac cagctggttc ctcgtgatat catggatact   5040
ggctccattt gtgttcaacc cgtcaggttt cgactggctt aagacggtct atgacttcga   5100
aggtttcatg aactggatct ggtatcaagg cagaatctca acgaaatccg aacagagctg   5160
```

-continued

```
ggagatatgg tggtacgagg aacaggacca cctgagaacc accggtatac caggaagaat   5220
aatggagata atcttggacc ttcggttttt cttcttccag tacgggattg tataccagct   5280
caaaatcgca aacggatcaa ccagcattct cgtctacttg ttgtcgtgga tatacatctt   5340
tgctgtgttt gtgttcttcc tggtaatcca atacgcccgt gacaagtact ctgcgaaaaa   5400
ccacatacgg tacaggcttg tccagttcct cctgatcgtg tttggttattc tggtgatcgt   5460
tgctctgctg gagttcacgc atttcagctt cgtggatatc ttcacgagtc ttcttgcgtt   5520
cgtcccaacc ggctggggaa tcttgctgat cgcacaggct ttaaggccta tgctgcagaa   5580
gttcaggctt atctggaacg ctgttgtctc ccttgctcgg ttatatgaca tactgttggg   5640
gatactcatc atggttcccg tagcattcat gtcatggatg cctgggtttc agtcaatgca   5700
aacgaggatc ttattcaatg aagctttttag cagagggctt cgtatcatgc agattgtcac   5760
tgggaagaaa tcaaaaggcg atgtctaagt tgaaaatgaa agaaggtaaa gctctttatt   5820
tactcaaaca tcttttatgt tctgtttgtt tggaatccta agattacaac aaaaccaatg   5880
caaagcttta taacttgcgt aggtcataat aaggtacatg gtaatttaaa gttgttggtt   5940
tgcggcgttg agatcagttg gaggttagtt ttctcgaaac atggtattct ataagttatt   6000
gcttcttgtc tgaataagaa ctcaaaagaa aaaccatgtg ttgttgttgt tgtcttcttc   6060
ttaaagcagg tgtttggaga gcttttgttg aggaatctgg aagttgggtt agatcatggg   6120
ttagcgggtg aaatatatat tgtcagtact ttgttagtgt gtggaaatgg gactctgatt   6180
cttgttgtct gaaacgatac agcattttgt gaagtagggc ttttgtgaaa gatttgtttc   6240
tctttctctc tcagtgtaga gctttagagc atttttttagt atatgtttaa tctttttatt   6300
ttctaatgtc atttgcattc atatctcacg tcttcctcgt tggtctgaaa ccggtttga   6360
gatgcttatc cattgtccac ttctctatg                                      6389
```

```
SEQ ID NO: 8            moltype = DNA  length = 9343
FEATURE                 Location/Qualifiers
source                  1..9343
                        mol_type = genomic DNA
                        organism = Raphanus sativus
SEQUENCE: 8
caaacgatca tagaaatgta cctgtaatta gtcaactgtt caaagagctt aatgcattgc   60
tccttatcaa tctgcccggt tttctgtcat aaacatgaaa tagaatacaa cgtaaacaca   120
tatgtttagc tatgtggtaa ctaacaggga gcttccctgt atatatctgt aggaggtaaa   180
aatcattttg aatggagtaa cttacgtctt tgtctataag accaaaggct ttctccagca   240
ttcttctctt catttgatcc attccagata cttgctttgc gagctacaaa aataacaaat   300
atgataccac gctagtgcgg tcgtttttag ttttaacata caaaagatca agttttgcaa   360
taaacctgtt ctttgaaact gtcataaaca acggcaagaa tcaagttcgt gacaaagtag   420
acgccaatta gtacgtagag cacgaagaac aacgaagacc agcgtgaaga cctatacaaa   480
aaaaaaaaag aacaaatcag tcgcccaaaa cactggatgt aactcatttc accatataaa   540
cttacttgta agcacgaatc cagacatcag gattgttgga tgttgtgaac aaaataaaca   600
tctggtaaag agttgcaccg taagacgtga agaccgtgag tccttgttgt gtatcctcaa   660
acataacaaa agcaatccaa ctggcaaaga gaaggaacag catccataga gcctgtggag   720
atattcaaga agtgaaagca tagaaggaca atcaatacga gttcatcact gttctgaaag   780
tcaaactcga ttgggaagac cactgaccaa gatattcaag tatgtgccaa gcattccaga   840
aagaaggacg aggctgtctc gaagttccct gtacagaaat tttaagaaac acagtttta   900
gacaagaaga taatataaaa caaaagtgca ctttcatcgt aaatggcatt ttggattgag   960
acaagttgat agaaaagaag cataaatatg tgttgatacc ttatgctgag gatgaatatg   1020
ataactctga catatggggc gattctaaaa ggaagaaaat cgaaagccac tggagacaag   1080
tatagaatgt caacgagcac atcaacaatc aaaactaaca cgcaagcaac ctggaatcag   1140
gaagaagaag acatttattg tgttaaaagt tatgaaatca atatcttaag ttctgtccaa   1200
cattcaacaa atagaaaaga aaaaaaaaag aaacagtgaa gaagacttat gtaggggaga   1260
ataccttcac taggttaagg cggcttgtcc aaaagatacg ggacccttca taggagattg   1320
ggaaaaaagt atgtacaagt agtataacca gggtaagtac ctgtttggag aaagcaaaaa   1380
tataagaatt tcagtacaat gagaaaggat cctggctagt ccgaacgata agataacgag   1440
tatataaata ttagcatcta cttaaacgag atcaactagt tttcacaaaa gtgtgtaatg   1500
aatctcaagc cttgaacttt caagtggatg catataagaa tatgtcagta cagtgagaaa   1560
ggatcctggc tagtctagtc ccaacaatat acaccatgga agataagacg agtatgttaa   1620
taaaattaac aacttcttaa acgagatcaa cgagtcttga atctttcaaa agtgggttaa   1680
tatgaatctg gtgtgcctaa ttgcactaaa atctatttgc atctacagcg aaaatgaaag   1740
gccagctact tgcctcaaag ataatggatt ctgcattggt caagtagggt aactccccaa   1800
ggtaatagta atctctgtct ttgcaagacg gcgtaggctt attttcacac cacaatggtt   1860
gctgcaaaaa gacaggacaa gaaagactgt cacactttt tctattttct tttaaaagta   1920
ttttcttttg ggggggtgg gggggggca aaaggttgct gacctcaaag aagttaatca   1980
aaatgagagc gaaatagttg agagaccaga tgagatctaa tcgtgtgtag ataaagtagt   2040
acttggcaga ctctccgaag ctggactggt caagtatttg ctcaggtaga cctataccat   2100
cttcagccta catacataca gcaaaataaa taaataaata aataaaaagg ttctcaaaat   2160
cagcaaaaaa gacaaagaaa ccgaacattt tctattgcta tattcgtaac ttattatcag   2220
gttaaagaaa caaatcattt tgaacaaaaa aaaaaaaaaa agaaacaaat catattctga   2280
gcaattattc agaataaacg atttggactt gtcagactga ttctattcac tgataaattg   2340
agaaatctcc ctcaagggag ttatgccatc atgtcacagt cagtcggaca aagatccatg   2400
aattttatca gaacaagaag aagacaaata tagttaggga gttgagagat agaaagagaa   2460
ccagatcgac gagagcagca gctttctgaa aggtggtacc atgagcgata gcttctgatc   2520
tacgaacaat ccgatccgta ccaccaccac gactctctct acctatcaaa ggatcttcca   2580
ttttttttt cttcaaaagg atcgaaatgg aaagcagaag accaaggacc ttatgtagta   2640
cctttctttc tttctttctg tcagtttatt gttggctacg aatttaata taatgataca   2700
gatcacaaga agaagatagt gatgatggcc cagaagtagt tgaattttta aaataaatta   2760
aattttccaa gtgatattag atcttgccga caaacacgtt ggggtcccTt tctcaatttg   2820
taactttgtg gatcaggatc taagtagatt ggtcaaaact gagagagtgg tgttgtggtc   2880
cgaataaaac tgattaaaga ataagactgc agagactaac aaacagaaga aacagataca   2940
tagagaagtg gacaatggag aagcatctca aaactggttt aacaagcaga gaagaagatg   3000
tgaaatatga atgcaaaatg acattagaaa atcaaagatt aaacatatac taaaaagaaa   3060
```

-continued

```
gtactctaaa gctctacaat gagagagaaa gagaagaaat ctgaacacaa aagccctact   3120
tcacacaaaa tgctgtaacg tttcagacaa taacaccata caagaatcag aatcagagtc   3180
ttccccctt ccccacact ctaacaaagt actgacaaat gtatatatat atgtttcccc     3240
cactaaccga tgctctaacc agataaccaa cttccaaatt cgtccacaaa agctctccaa   3300
aaacctgttt caagcacaag acagaacaaa agatgggttt atttgagttc ttcttcgcac   3360
accaaggata acttaaaaaa aattccatct ctcgagaaaa ctaactaacc tccaaatgat   3420
caccatcgcc gcaaaccaac agctttttca agttaccatt taccatacga cctacacaag   3480
ttataaagct tcgcattggt cttgttgtaa atcttaggat tccaaaacaa acaggatatt   3540
aaagatgttt cagtaaataa aagagcttta ccttcttctt tcttcaactt agacatcgat   3600
ttttgatttc ttcccagtga caatctgcat gatacgaagc cctctgctaa aggcttcatt   3660
gaataagatc cttgtttgca ttgattgaaa cccaggcatc cacgacatga acgctacggg   3720
aaccatgatg agtatcccga acagtatgtc atatacccta gcaagggaga caaccgcgtt   3780
ccagataagc ctaaacttcg tcagcgctgg cctttaaagcc tgtgcgatca gcaagattcc   3840
ccatccggtt gggacgaacg caagaagact cgtgaagata tccacgaagc tgaaatgcgt   3900
gaactctagc agagcaacaa tcaccagaat accaaacacg atcaggagga actgaacgag   3960
cctgtaccgt atgtggtttc tcgcagagta cttgtcacgg gcgtactgga ttatcaggaa   4020
gaacacaaac actgcaaaga tgtatatcca tgacaacaag tagacgagaa tgctggttga   4080
tccgcttgcg attttgagct ggtaaacaat cccgtactgg aagaagaaaa accgaaggtc   4140
caagattatc tccacaactc ttcctggtat accggtggtt ctcaggtggt cctgttcctc   4200
ataccaccat atctcccagc tctgttccga tttcgttgag attctgcctt gataccagat   4260
ccagttcatg aagccttcga agtcatagac cgtcttaagc cagtcgaatc ctgacggtt    4320
gaacacaaat ggggccagta tccatgatat cacgaggaac cgtgaagata gagtcatggc   4380
tatgtagatc aatgagtctt tggcgatggg actgtgcgta gcatagacta tgaggatcag   4440
cccgagctcg atggccttca caaagtgact gcgtgcatag agtcggtagt tctcggtgaa   4500
actcttgtgtc tcgacaacaa atccacgtcc agtggctctg tactttgctc caccatggag   4560
aatggttcga ccaaaatagt gagctctggt ccccattgag aatgtgtaga agacagagga   4620
aagctgaatc tgcatccgaa tgaaattcca tatagctaga aggaaaccct cctcgagaga   4680
ccattccaca atcattggca gggcagtgaa cagaccaagc tgaacgatga actgctggtt   4740
cagtatcaca gcaagcgctg cgttggtgtc tgtactgtct gctagagcgg acttctcaac   4800
accgctcagc gcgagataaa cccggcccca gaggaaagcg taaaccgtaa gaatgaccat   4860
catcgtgttg aagaaaaacc cgaccgttgt gtagaaaaat gataacattc tgaagaaatc   4920
gagcctatga cccagcctgt acacatctcg gctaagaacc tgctctccat tcccactggc   4980
taccttagcc tcaaacattg atatttgatt caatccaaca tcccggccct tcccaacctg   5040
aatatatgta caaaaaacaa gggttatgca atttacattg aagaaacaag gaacgttaag   5100
ttgcatggtt ataacaaaaa aaaaaattga actataggat ttctgtcgca gtataaatta   5160
gttagaaata tcaaaataat gaacattacc aacctgaata tactcgtggt gggtgacgtt   5220
accgcctcgc aatgtgcaat taaacccggc gaagatgtct tcactgatat ttatgactct   5280
ggaagctttg ctgataccac ctcgactcaa gaaccagaat ctgtcaaaaa catcgggtg    5340
accataatgc attctgacct taagcgggtt ggcaagaaca cgctgaccaa gagtgacaaa   5400
actagtctcc tgagcagaca tgaaccacgc cagagacgag acagagcccg tgaagatgtg   5460
ctcccggaca ccgagaatag ttggctttct gatcccatga gattttctaa actcctggag   5520
caaatttctc atcttgagag cctcctcaaa ataattatcc tggttcatat ctatggtctg   5580
aacagcatca ccacgggtaa agatcattgc atgattctgg ttccctcacc                5640
cagcttcaac ggaccaggca gcttcacacg gaatatctcc acttccttct ccaacgtgtg   5700
atcgtatttc accagaactg agtaatactc tgtctctccc ctgcccgcat gcacctcatc   5760
cacatacgca atacggaggg cttcattttg cttcataaga tacagaattt cctctgcctg   5820
aggctccttc tttgctttt gagacccata gatctggcac gccacgacat atgtgaattt    5880
catcaatgca gtcccatgct catggccttt atacagcatg ctcacggagc tagttgctct   5940
gcttagagaa gatccaccat ttacatcgtc aaccccatcc agtcgaccat ttccctgcga   6000
actcctcatt gaaccaagct cctgagcatc ctcccgaatg tccatttcag acgcagagtc   6060
aagaaaagca agcatcttaa gagccctgta atagtacatc attcctcgaa ctgtacgtgc   6120
caaagtctga cctctgtagg aagcccaaag cctgagctct ctcagcttgg ttgtccacaa   6180
ctcaacatct gtctttatac cttccctacg catccgttcc ttaaaatttt tccattcgtc   6240
agcataaatc gtctgcaggt aatacaaggt tgaaatccca tcctcagtct cgttttgag    6300
ctgttctttg ctgtatacaa cttcctcgct gtagtatgga gtcagaacac tgaacgccaa   6360
cattttctcc acctgaggtg catgaggcaa gttcatgaag agcgaattgc tgaagaaggc   6420
aatccgccgt ctcgcctcta gattcacagg gacgctgtgc atagagtccc tagaagtgag   6480
aattgtgtgt aaccgcctaa cctgccgaaa gaagtcttca ttgcttgcat cgggaagcct   6540
aacagcgttc tgaaacagta acttggaggc tggatcatga ggagtcaacc cctcattaga   6600
tagctgttca gttgtcttct tctctatgaa gaactgtcgt gttgcaatct cataaatcga   6660
ctgcaaaaca ttcaccactc gctcaatatc tggcttctca gcattcagta gcccaaccaa   6720
cttctgaagt gtctcgtaca tctttggcag aaggtccact ttaaaggtct tggtgaactg   6780
ctcaccctga atagagacct caatcatctg gaagaagatc gtaatgattt tatgttcttc   6840
ggtgtcaatc ttgatgattg agagcagcag atgtttgatg ctgtcatatg cctcaacaag   6900
agcacaacgc ctgtactcat tcttgcatat cttgtgccac agccatttat caggagcatc   6960
aaccagctct ttcgcctggc tcagtgcaag taaaagctcg ttgcacagca ggaaacacgg   7020
ccagcggata actgacacat tccacgaatt ctttggcagc tccagtagct ctacttctcg   7080
atcagagact atatcctctt ctctgaaagc taagattatc tcattccaga tcaacgcaaa   7140
cttgttggct tcaacctgat tagactcgag tttcttaaac ggccgcccaa atccatacct   7200
cagcttcaac ctgcataaag tacacaaact caaggttatt attatgttga aaactcgaat   7260
tccaagcttg taccgtaaag acaaactctg tatagtaaac tataaatata ggaatatgct   7320
tgcacagact tacctatgaa tggcgtcctt aagcttgtta ccaaagcctc tagcattcag   7380
gagttgttcc tcaggcatta ggttgaactg aatagcgcta gcaaagaact gaaacctcag   7440
cctaagctgt cccatgtccc tgatctcccc cagatgatca aacaacccaa caatagcacc   7500
aacaatcgac gaatagattg cgtaccaaat ttggatatcc atcaggtata tcaacaccac   7560
tggcagccat aataacaaga cagaaaacct attgctctcg ccaaagaact gatgccactc   7620
ataatctacc tcctttaagt tccatagcag cttcgagggt ttaatcattg gtttaacctg   7680
caggaagtag ctgaaaatga acttcgttgc taggacaaag atccagaacg ccgagtactt   7740
gatgttgtcc accaaacccct ctctcaaacc tcgacccaca aagctttttac cctggaacca   7800
```

-continued

```
ccaagttaaa gcaaagaata ttttccaatt gctctcttcc agaaagttcc ttatccacgg   7860
gattataaac agagccaaag ccaggatctc agggaccaag aatgccacca cggcgtaaag   7920
gaattggtag atcttgtcat tcgcggctct ggaccactgt ctatcttgct tcctctgctt   7980
ccagatgttc gtgtagagaa caataaaggc tataatccaa accgtggcag ctacaacctt   8040
catcaacatt ctgaaaaaca gccgtttggt ctctctagaa atgaggggcc gttgcgaacc   8100
agcgtccagc acagcctgca gtagtctcat cccactccac gtcaagaaaa ctgtcaaaag   8160
cctcacctga acatctctcg acttcaaggc attccacatc tgctttgcca ccgaccctct   8220
atccggcttc tcctcccaag caactataat ggcggcttga aggaacaaag caagcatcac   8280
ccaaagccta tcaaagctcc tgtagagata aaaaaacggt ctccgctcca caaaaccggt   8340
cttcccaacg ctcttccctc tactattctt gaagaaactg ctccccaaat caagcggcca   8400
tttcaactta ctgaaacacc tatccgtcca gaaatactca ttaatatcat catagttcct   8460
ccacttacaa tgcggctccg tcccgttctt gctctcatta atctcagctc ggatcgtctc   8520
gtaaataggt ttaacgacgc cgtttaggaa agcgttctcc ccagagagag taggcgtata   8580
aggctgcccc gtgttctcgt cgaggcaatc ctccaacacc ttgttaagct ccgaggccat   8640
attgtggaag atgtaacaga cgcactcggg catgaaccta agattcgcgg cctcgcccca   8700
cacgaggagg tagagaccga cgtagagaag ctcccgcctc gaatcggggc tccgatccga   8760
gatccagatg ttcgatttcc tcccgaggta ggagcaccag ctggagtagt tcccgaggag   8820
cttgcgcggg aagcggcgga cgacggcggg atcgagggag tcgatgttgt cggggggagg   8880
ggagaggcgc atctgggcgt tggcgaggtg gaggacgacg tgctcgcgct ggttgcggac   8940
gttgtccttc tggaagccga agaagagggc gagccagtcg aggaggtcgt agtgagggcg   9000
ccattggacg aagggaggac ggcggaggtc tccgacggtt ttgagagcgg cggcggcggc   9060
gcggacctcg gggtagcgga gggaagggtg gtcggcgaag aggttgttga cgggatgat   9120
gttgtagggc tcctcctcgg ttcccccgc cgacggccgt ccggtttgag atggacggt    9180
gcggtggcgg aggctcatag tagcatgtgg tggatcttgg agatggtgtg aaggaggagg   9240
agactgattc aaaggatgtg gagagagaga gagagagaga gagagagaga gagagagaga   9300
gagattgaat tgaagcgttg cgatatgttt ttctctttta gct                     9343
```

```
SEQ ID NO: 9               moltype = DNA   length = 23
FEATURE                    Location/Qualifiers
source                     1..23
                           mol_type = genomic DNA
                           organism = Brassica sp.
SEQUENCE: 9
acacgaacat ctggaagcag agg                                            23

SEQ ID NO: 10              moltype = DNA   length = 22
FEATURE                    Location/Qualifiers
source                     1..22
                           mol_type = genomic DNA
                           organism = Brassica sp.
SEQUENCE: 10
gaaagccacc acagcgtaaa gg                                             22

SEQ ID NO: 11              moltype = DNA   length = 23
FEATURE                    Location/Qualifiers
source                     1..23
                           mol_type = genomic DNA
                           organism = Arabidopsis thaliana
SEQUENCE: 11
acgaaaccga cgaacaaccg cgg                                            23

SEQ ID NO: 12              moltype = DNA   length = 23
FEATURE                    Location/Qualifiers
source                     1..23
                           mol_type = genomic DNA
                           organism = Arabidopsis thaliana
SEQUENCE: 12
tattgattct ctcgattccg cgg                                            23

SEQ ID NO: 13              moltype = DNA   length = 23
FEATURE                    Location/Qualifiers
source                     1..23
                           mol_type = genomic DNA
                           organism = Arabidopsis thaliana
SEQUENCE: 13
gaacgccatt gaacatacgg cgg                                            23

SEQ ID NO: 14              moltype = DNA   length = 23
FEATURE                    Location/Qualifiers
source                     1..23
                           mol_type = genomic DNA
                           organism = Arabidopsis thaliana
SEQUENCE: 14
gattgcctcg atgagaacac cgg                                            23

SEQ ID NO: 15              moltype = DNA   length = 19
FEATURE                    Location/Qualifiers
source                     1..19
                           mol_type = other DNA
```

```
                          organism = Synthetic construct
SEQUENCE: 15
cgccgtctca gagctacaa                                                  19

SEQ ID NO: 16          moltype = DNA   length = 20
FEATURE                Location/Qualifiers
source                 1..20
                       mol_type = other DNA
                       organism = Synthetic construct
SEQUENCE: 16
ggcggcttga aggaacaaag                                                 20

SEQ ID NO: 17          moltype = DNA   length = 48
FEATURE                Location/Qualifiers
source                 1..48
                       mol_type = other DNA
                       organism = Synthetic construct
SEQUENCE: 17
gtcgacctgc aggcatgcct gtcttaaatg gacatttgta gtaacaaa                  48

SEQ ID NO: 18          moltype = DNA   length = 40
FEATURE                Location/Qualifiers
source                 1..40
                       mol_type = other DNA
                       organism = Synthetic construct
SEQUENCE: 18
aagttctctc ctttactgac atcgcctttt tgatttcttc                           40

SEQ ID NO: 19          moltype = DNA   length = 20
FEATURE                Location/Qualifiers
source                 1..20
                       mol_type = other DNA
                       organism = Synthetic construct
SEQUENCE: 19
cctgttccaa aggtcctgca                                                 20

SEQ ID NO: 20          moltype = DNA   length = 20
FEATURE                Location/Qualifiers
source                 1..20
                       mol_type = other DNA
                       organism = Synthetic construct
SEQUENCE: 20
tgtcatacca cttgtccgcc                                                 20

SEQ ID NO: 21          moltype = DNA   length = 38
FEATURE                Location/Qualifiers
source                 1..38
                       mol_type = other DNA
                       organism = Synthetic construct
SEQUENCE: 21
tatgaccatg attacgccca atttgcggcc aagttcca                             38

SEQ ID NO: 22          moltype = DNA   length = 45
FEATURE                Location/Qualifiers
source                 1..45
                       mol_type = other DNA
                       organism = Synthetic construct
SEQUENCE: 22
actagtcaga tctaccattc aagaccttct tttttcaact tcgac                     45

SEQ ID NO: 23          moltype = DNA   length = 41
FEATURE                Location/Qualifiers
source                 1..41
                       mol_type = other DNA
                       organism = Synthetic construct
SEQUENCE: 23
tatgaccatg attacgccgc ttgtcttgct tgtttttgct c                         41

SEQ ID NO: 24          moltype = DNA   length = 46
FEATURE                Location/Qualifiers
source                 1..46
                       mol_type = other DNA
                       organism = Synthetic construct
SEQUENCE: 24
actagtcaga tctaccattt aagaccttct tttttcaact tcgaca                    46

SEQ ID NO: 25          moltype = DNA   length = 41
FEATURE                Location/Qualifiers
source                 1..41
```

-continued

```
                              mol_type = other DNA
                              organism = Synthetic construct
SEQUENCE: 25
tatgaccatg attacgcccg ataaggaaac gagagaggtt g                      41

SEQ ID NO: 26          moltype = DNA   length = 42
FEATURE                Location/Qualifiers
source                 1..42
                       mol_type = other DNA
                       organism = Synthetic construct
SEQUENCE: 26
actagtcaga tctaccatgc tgtaacgttt cagacaataa cc                     42

SEQ ID NO: 27          moltype = DNA   length = 41
FEATURE                Location/Qualifiers
source                 1..41
                       mol_type = other DNA
                       organism = Synthetic construct
SEQUENCE: 27
tatgaccatg attacgccgt gtgtttcgga aagcagcaaa c                      41

SEQ ID NO: 28          moltype = DNA   length = 39
FEATURE                Location/Qualifiers
source                 1..39
                       mol_type = other DNA
                       organism = Synthetic construct
SEQUENCE: 28
actagtcaga tctaccatac tgaaacccag gcatccacg                         39

SEQ ID NO: 29          moltype = DNA   length = 42
FEATURE                Location/Qualifiers
source                 1..42
                       mol_type = other DNA
                       organism = Synthetic construct
SEQUENCE: 29
tatgaccatg attacgccgt taggtgacga ctatatcagc at                     42

SEQ ID NO: 30          moltype = DNA   length = 43
FEATURE                Location/Qualifiers
source                 1..43
                       mol_type = other DNA
                       organism = Synthetic construct
SEQUENCE: 30
actagtcaga tctaccatga gagaaagata tcaaatcttg cac                    43

SEQ ID NO: 31          moltype = DNA   length = 42
FEATURE                Location/Qualifiers
source                 1..42
                       mol_type = other DNA
                       organism = Synthetic construct
SEQUENCE: 31
tatgaccatg attacgccgc taatcttgaa caagtcctgg at                     42

SEQ ID NO: 32          moltype = DNA   length = 42
FEATURE                Location/Qualifiers
source                 1..42
                       mol_type = other DNA
                       organism = Synthetic construct
SEQUENCE: 32
actagtcaga tctaccatgg aagacgtgag atatgaatgc aa                     42

SEQ ID NO: 33          moltype = DNA   length = 42
FEATURE                Location/Qualifiers
source                 1..42
                       mol_type = other DNA
                       organism = Synthetic construct
SEQUENCE: 33
tatgaccatg attacgccgt acctgtaatt agtcaactgt tc                     42

SEQ ID NO: 34          moltype = DNA   length = 40
FEATURE                Location/Qualifiers
source                 1..40
                       mol_type = other DNA
                       organism = Synthetic construct
SEQUENCE: 34
actagtcaga tctaccatca ccatctccaa gatccaccac                        40

SEQ ID NO: 35          moltype = DNA   length = 19
FEATURE                Location/Qualifiers
```

-continued

```
source                  1..19
                        mol_type = other DNA
                        organism = Synthetic construct
SEQUENCE: 35
gacgctggct cgcaacggt                                          19

SEQ ID NO: 36           moltype = DNA  length = 20
FEATURE                 Location/Qualifiers
source                  1..20
                        mol_type = other DNA
                        organism = Synthetic construct
SEQUENCE: 36
cggccgcccc aatccatacc                                         20

SEQ ID NO: 37           moltype = DNA  length = 18
FEATURE                 Location/Qualifiers
source                  1..18
                        mol_type = other DNA
                        organism = Synthetic construct
SEQUENCE: 37
acgctgcctc gcaacggc                                           18

SEQ ID NO: 38           moltype = DNA  length = 21
FEATURE                 Location/Qualifiers
source                  1..21
                        mol_type = other DNA
                        organism = Synthetic construct
SEQUENCE: 38
tggccgccca agtccatacc t                                       21

SEQ ID NO: 39           moltype = DNA  length = 19
FEATURE                 Location/Qualifiers
source                  1..19
                        mol_type = other DNA
                        organism = Synthetic construct
SEQUENCE: 39
acgcctggct cgcaacggc                                          19

SEQ ID NO: 40           moltype = DNA  length = 20
FEATURE                 Location/Qualifiers
source                  1..20
                        mol_type = other DNA
                        organism = Synthetic construct
SEQUENCE: 40
cggccgcccc aatccatacc                                         20
```